United States Patent
Chen et al.

(10) Patent No.: US 11,466,020 B2
(45) Date of Patent: Oct. 11, 2022

(54) COMPOUNDS AND COMPOSITIONS FOR INHIBITION AND ELIMINATION OF ZIKA INFECTION AND USES FOR SAME

(71) Applicants: Cornell University, Ithaca, NY (US); The University of North Carolina at Chapel Hill, Chapel Hill, NC (US)

(72) Inventors: Shuibing Chen, Pelham, NY (US); Ting Zhou, New York, NY (US); Lei Tan, Bronx, NY (US); Qisheng Zhang, Chapel Hill, NC (US)

(73) Assignees: Cornell University, Ithaca, NY (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/494,692

(22) PCT Filed: Mar. 19, 2018

(86) PCT No.: PCT/US2018/023157
§ 371 (c)(1),
(2) Date: Sep. 16, 2019

(87) PCT Pub. No.: WO2018/170513
PCT Pub. Date: Sep. 20, 2018

(65) Prior Publication Data
US 2020/0102320 A1    Apr. 2, 2020

Related U.S. Application Data

(60) Provisional application No. 62/472,881, filed on Mar. 17, 2017.

(51) Int. Cl.
*C07D 491/052*    (2006.01)
*A61P 31/14*    (2006.01)
(Continued)

(52) U.S. Cl.
CPC .......... *C07D 491/052* (2013.01); *A61P 31/14* (2018.01); *C07D 491/153* (2013.01); *C07D 519/00* (2013.01)

(58) Field of Classification Search
CPC ............ C07D 491/044; C07D 491/152; C07D 491/153; C07D 487/04; C07D 519/00;
(Continued)

(56) References Cited

U.S. PATENT DOCUMENTS

2009/0196917 A1    8/2009    Joguparthi et al.

OTHER PUBLICATIONS

Yunusov, et. al., Doklady Akademii Nauk UzSSR (1953), No. 6, 44-7.*

(Continued)

Primary Examiner — Jeffrey H Murray
(74) Attorney, Agent, or Firm — Hodgson Russ LLP

(57) ABSTRACT

Provided are compounds and compositions for prevention and/or elimination of Zika virus infection. Also provided are methods for preventing and treating a subject in need of prevention or treatment of Zika virus. The compounds of the present disclosure have the following structure:

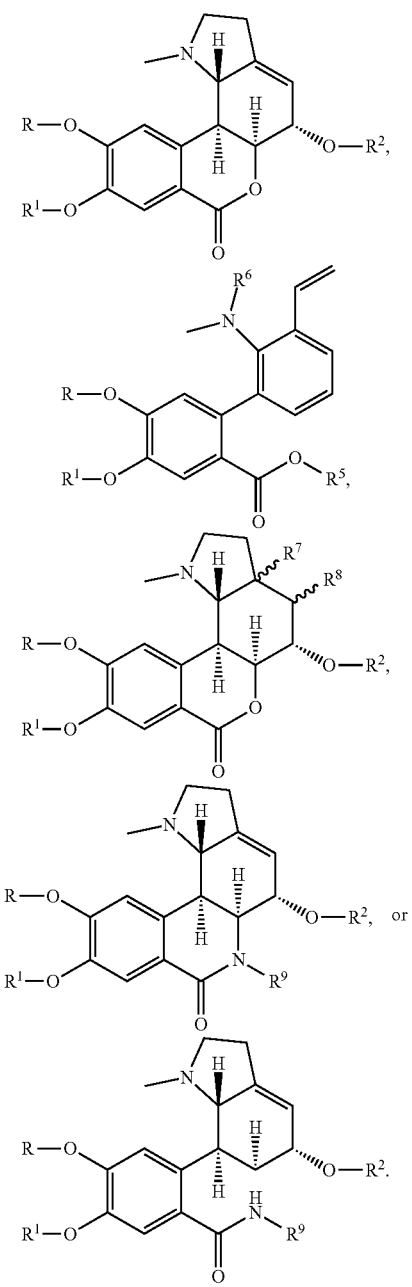

9 Claims, 45 Drawing Sheets
Specification includes a Sequence Listing.

(51) Int. Cl.
  *C07D 491/153* (2006.01)
  *C07D 519/00* (2006.01)
(58) Field of Classification Search
  CPC .. A61K 31/235; A61K 31/407; A61K 31/437; A61P 31/12
  USPC ............... 514/312, 392, 393, 254.11, 447; 548/418, 426, 303, 307
  See application file for complete search history.

(56) References Cited

OTHER PUBLICATIONS

Boit, et. al., Chemische Berichte (1956), 89, 2093-7.*
Phokas, G., Pharmaceutica Acta Helvetiae (1969), 44(4), 257-9.*
Cedron, et. al., European Journal of Medicinal Chemistry (2013), 63, 722-730.*
Pubchem CID: 72198217, create date Dec. 16, 2013, p. 4 formula, 12 pages.
Byler, K.G., et al., In-silico screening for anti-Zika virus phytochemicals, Journal of Molecular Graphics and Modeling, Aug. 28, 2016, vol. 69, pp. 78-91.
Viladomat, F., et al., Homolycorine hydrochloride dihydrate, Acta Cryst., 1999, C55, pp. 385-387.
Crouch, N.R., et al., Alkaloids from three ethnomedical Haemanthus species: *H. albiflos, H. deformis* and *H. pauculifolius* (Amaryllidaceae), South African Journal of Botany, 2005, vol. 71, No. 1, pp. 49-52.

* cited by examiner

B

Hippeastrine hydrobromide (HH)    Amodiaquine dihydrochloride dihydrate (AQ)

| | dose | ZIKV only | 50 | 25 | 10 | 5 | 2.5 | 1 | 0.5 | 0.25 | 0.1 | 0.05 | MOCK | IC50 value (uM) (calculated with Graphpad Prism) |
|---|---|---|---|---|---|---|---|---|---|---|---|---|---|---|
| HH | ave | 47.71% | 0.57% | 0.67% | 3.31% | 54.47% | 61.94% | 64.44% | 63.69% | 60.44% | 55.21% | 51.72% | 0.13% | 65.03% |
| | stdv | 10.39% | 0.43% | 0.67% | 1.31% | 7.51% | 7.77% | 6.32% | 7.08% | 9.42% | 12.74% | 12.77% | 0.21% | 72.81% |
| AL-32# | ave | 69.22% | 53.83% | 70.30% | 70.89% | 74.11% | 68.98% | 70.42% | 69.59% | 65.34% | 64.54% | 66.32% | 0.18% | 74.09% |
| | stdv | 4.20% | 11.53% | 6.18% | 5.71% | 4.05% | 5.69% | 6.60% | 6.91% | 9.18% | 9.65% | 10.17% | 0.17% | 77.79% 6.77 |
| AL-30# | ave | 47.19% | 1.75% | 29.46% | 58.12% | 70.70% | 66.79% | 66.65% | 66.61% | 60.69% | 59.35% | 57.05% | 1.21% | 73.21% UD |
| | stdv | 15.57% | 1.15% | 7.53% | 14.40% | 6.97% | 7.05% | 12.86% | 9.84% | 13.99% | 15.38% | 16.26% | 1.94% | 70.94% |
| AL-29# | ave | 69.94% | 0.68% | 35.59% | 68.23% | 69.64% | 73.39% | 62.62% | 60.37% | 58.48% | 52.22% | 55.30% | 0.26% | 70.41% 25.18 |
| | stdv | 5.51% | 0.94% | 10.38% | 6.43% | 3.85% | 5.05% | 8.61% | 10.69% | 11.11% | 10.79% | 10.81% | 0.41% | 69.55% |
| AL-28# | ave | 65.68% | 58.60% | 71.06% | 69.94% | 75.47% | 68.77% | 71.17% | 72.01% | 71.83% | 72.27% | 70.01% | 0.11% | 69.94% 25.38 |
| | stdv | 5.01% | 10.58% | 2.91% | 6.03% | 2.80% | 8.22% | 2.93% | 3.43% | 4.01% | 2.62% | 4.04% | 0.07% | 67.56% |
| AL-20# | ave | 64.16% | 19.57% | 51.33% | 65.36% | 75.65% | 70.70% | 68.34% | 71.25% | 67.76% | 67.73% | 67.06% | 0.54% | UD |
| | stdv | 8.42% | 6.88% | 8.04% | 10.42% | 3.52% | 4.18% | 5.05% | 4.04% | 9.29% | 7.72% | 8.53% | 0.87% | 38.53 |
| AL-17# | ave | 70.46% | 65.03% | 72.81% | 74.09% | 77.79% | 73.21% | 70.94% | 70.41% | 69.56% | 69.94% | 67.56% | 0.15% | |
| | stdv | 3.29% | 5.94% | 6.41% | 2.13% | 2.74% | 4.47% | 6.35% | 3.43% | 4.24% | 4.15% | 6.17% | 0.06% | UD |

COMPOUNDS AND COMPOSITIONS FOR INHIBITION AND ELIMINATION OF ZIKA INFECTION AND USES FOR SAME

CROSS REFERENCE TO RELATED APPLICATIONS

This application claims priority to U.S. Provisional Application No. 62/472,881, filed on Mar. 17, 2017, the disclosure of which is hereby incorporated by reference.

STATEMENT REGARDING FEDERALLY SPONSORED RESEARCH

This invention was made with government support under grant nos. DK098093 and DK111907 awarded by the National Institutes of Health. The government has certain rights in the invention.

FIELD OF DISCLOSURE

The disclosure generally relates compounds, compositions, and methods to treat Zika virus infection.

BACKGROUND OF THE DISCLOSURE

Zika virus (ZIKV), a mosquito-borne positive-sense single-stranded RNA virus in the Flaviviridae family, was first isolated in 1947 in the Zika Forest in Uganda from a sentinel Rhesus macaque and subsequently found in Aedes africanus mosquitoes. Historically ZIKV infections were limited in scope with sporadic global outbreaks until a recent large outbreak first observed in Brazil brought ZIKV to the forefront of public health concerns. ZIKV infection is considered to be associated with an increased incidence of congenital defects, and several reports support a direct link between ZIKV infection and congenital and adult brain defects.

The World Health Organization has therefore declared a global health emergency and compelled the scientific community to find solutions to the ZIKV threat (Heymann et al., Lancet 387, 719-21, 2016). Although an antibody-based treatment of ZIKV infection was recently reported to prevent ZIKV replication in mice (Sapparapu et al., Nature 540, 443-47, 2016), the high cost of antibody-based therapy limits its broad application. There is therefore an urgent need to develop cost-efficient therapies for ZIKV patients. Toward this goal, one group identified two established anti-flaviviral drugs (bortezomib and mycophenolic acid) and a drug with previously unknown antiviral activity (daptomycin) that can decrease ZIKV infection in Huh-7 and other cell lines (Barrows et al., Cell Host & Microbe 20, 259-70, 2016). A second group identified three categories of compounds, including a pan-caspase inhibitor that protects human neural progenitor cells ("hNPCs") from ZIKV-induced cell apoptosis (emricasan), an FDA approved anthelmintic drug that inhibits ZIKV infection (niclosamide), and a group of cyclin-dependent kinases inhibitors that inhibit ZIKV replication. Combination therapy with drugs from all three categories protects hNPCs and astrocytes from ZIKV-induced cell death (Xu et al., Nat. Med. 10, 1101-07, 2016).

Although these studies identify ZIKV inhibitors, most reported compounds were only tested in vitro during short-term culture. The long-term effect of these drugs is unknown. More importantly, none of the reported compounds has been evaluated in vivo. To date, no prophylactic or therapeutic treatment is available to prevent or treat ZIKV infection. Therefore, it remains an urgent and unmet need to identify drug candidates preventing ZIKV transmission to uninfected subjects and for treating and eliminating ZIKV in infected patients.

SUMMARY OF THE DISCLOSURE

The present disclosure provides methods for identification of compounds for the inhibition and/or elimination of Zika virus (ZIKV), such as inhibition and/or elimination of Zika virus from the system of a subject. The compounds can be used in compositions that can be used for treatment of subjects who have been infected with the Zika virus or who are at risk of being infected with the Zika virus. Thus, the compositions can be used for prophylactic and/or therapeutic purposes. The compositions can comprise the active compounds as described herein and other excipients and stabilizers and the like. Such additives are well known in the art.

In this disclosure, a high content screen using a chemical library containing FDA approved drugs or drug candidates was performed and compounds that can inhibit Zika virus (ZIKV) infection identified. It was shown that one of these drug candidates, hippeastrine hydrobromide (HH), eliminates ZIKV from hNPCs previously infected with virus. HH was further tested using a human fetal forebrain-like organoid model and shown to eliminate ZIKV from infected tissue while preserving normal neural architecture. Finally, both drug candidates were also shown to suppress ZIKV infection in the adult mouse brain in vivo. This disclosure identifies drug candidates that provide long-term in vivo control of ZIKV infection in both fetal and adult brain, and can be used to develop broadly effective clinical therapies for ZIKV infection.

In an aspect, the present disclosure provides compounds. The compounds can be used to treat (e.g., therapeutically or prophylactically) Zika infection.

In an example, a compound of the present disclosure has the following structure:

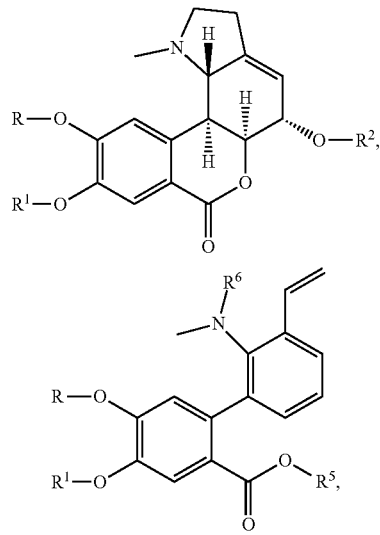

-continued

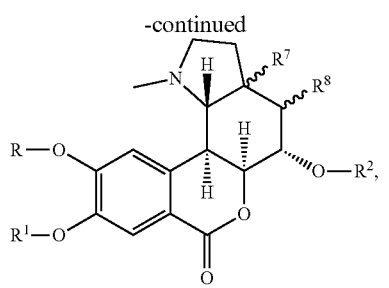

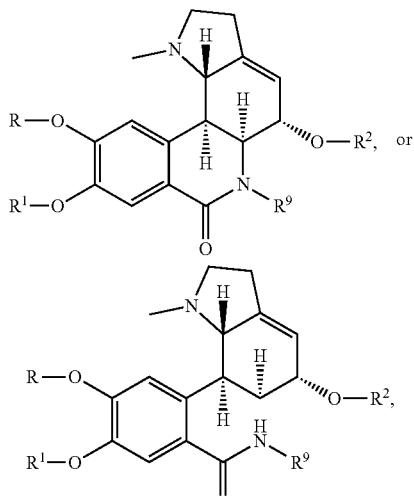

where R and $R^1$ are independently selected from H; $C_1$ to $C_8$ acyl aliphatic groups; $C_1$ to $C_8$ carbamide aliphatic groups; $C_1$ to $C_8$ amide aliphatic groups; $C_1$ to $C_8$ aliphatic groups; $C_1$ to $C_8$ acyl aliphatic aryl groups, where $C_1$ to $C_8$ is the length of the aliphatic portion of the acyl aliphatic aryl group, $C_1$ to $C_8$ carbamide aliphatic aryl groups, wherein $C_1$ to $C_8$ is the length of the aliphatic portion of the carbamide aliphatic aryl group; or $C_1$ to $C_8$ amide aliphatic aryl groups, where $C_1$ to $C_8$ is the length of the aliphatic portion of the amide aliphatic aryl group; or R and $R^1$ taken together form

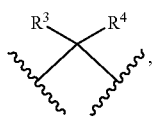

where $R^3$ and $R^4$ are independently selected from H and $C_1$ to $C_8$ aliphatic groups; where $R^2$ is selected from H; $C_1$ to $C_8$ acyl aliphatic groups; $C_1$ to $C_8$ carbamide aliphatic groups; $C_1$ to $C_8$ amide aliphatic groups; $C_1$ to $C_8$ acyl aromatic groups; $C_1$ to $C_8$ carbamide aryl groups; or $C_1$ to $C_8$ amide aryl groups, or $R^2$ has the following structure:

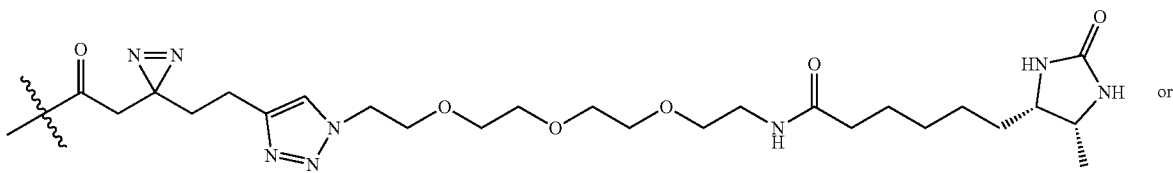

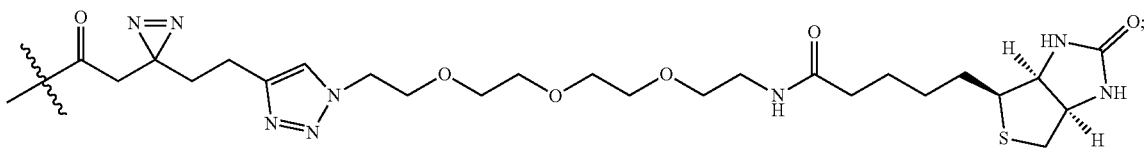

where $R^5$ is selected from H and $C_1$ to $C_8$ aliphatic groups, or $R^5$ has the following structure:

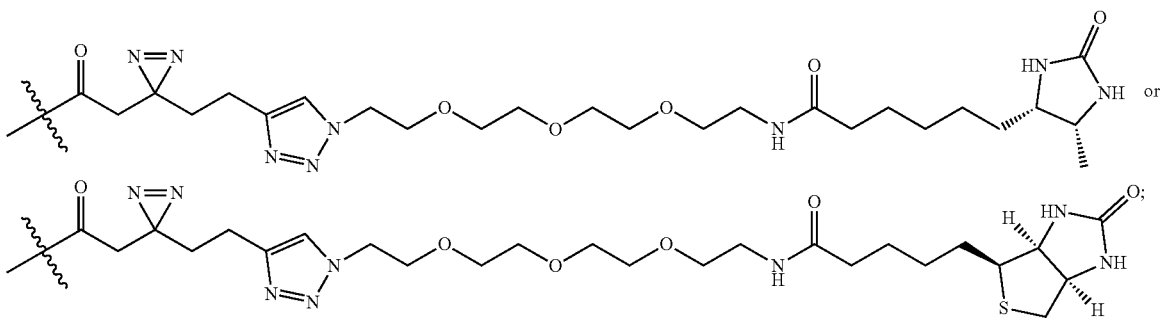

where $R^6$ is selected from H and $C_1$ to $C_8$ aliphatic groups; where $R^7$ is H, where the stereochemistry is R or S; where $R^8$ is H, where the stereochemistry is R or S; and where $R^9$ is a $C_1$ to $C_8$ aliphatic group.

In an aspect, the present disclosure provides compositions. The compositions comprise one or more compound of the present disclosure. The compositions can comprise one or more pharmaceutically acceptable carrier.

In an aspect, the present disclosure provides methods of treating and/or inhibiting a Zika viral infection. For example, a method of treating comprises administering one or more compound of the present disclosure or a composition comprising one or more compounds of the present disclosure to a subject in need of treatment for a Zika infection (e.g., a subject infected with ZIKV or a subject in need of a prophylactic treatment for a Zika viral infection). In various examples, a method comprises administering to a subject who has a Zika infection a therapeutically effective amount of a compound or composition of the present disclosure.

DESCRIPTION OF THE DISCLOSURE

Figure 1:
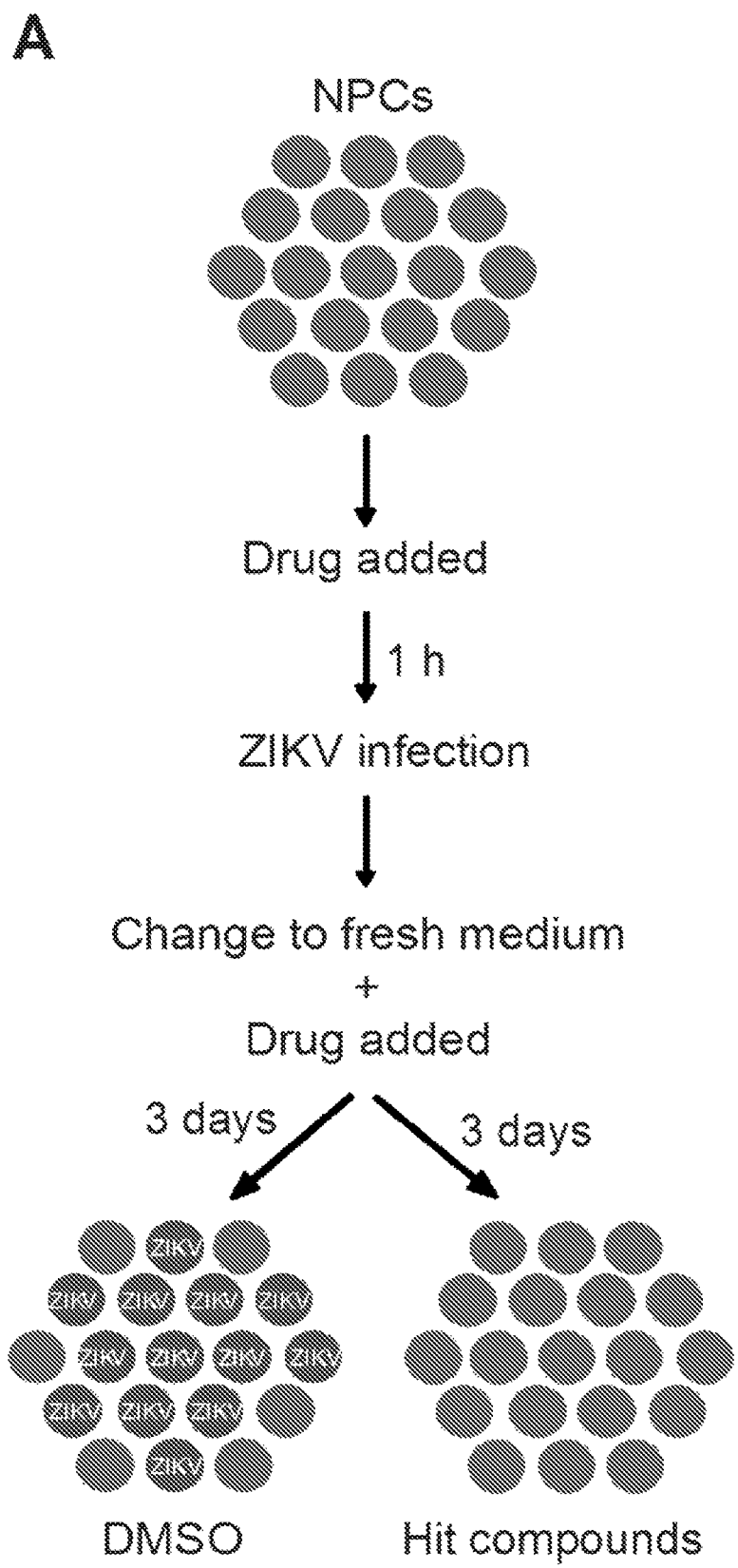
FIG. 1 shows a high content chemical screen identifies anti-ZIKV compounds in hNPCs. (A) Scheme of high content chemical screen. (B) Chemical structure of hit compounds. (C) Inhibitory curve and $IC_{50}$ of HH or AQ on hNPCs (n=6). (D-H) Immunocytochemistry analysis (D), the quantification of the infection rate (E), the quantification of proliferation rate (F), the quantification of cell apoptosis rate (G) and the normalized cell viability (H) of hNPCs at 72 h after ZIKV (MR 766 strain) infection with or without drug treatment. Scale bars, 100 µm. The ZIKV infection rate is defined as the percentage of ZIKV $E^+$ cells. The proliferation rate is defined as the percentages of $Ki67^+$ cells. The cell apoptosis rate was defined as the percentage of cleaved-Caspase 3/$CAS3^+$ cells. The normalized cell viability was calculated by dividing the total cell number of each condition by the total cell number under mock infection conditions. (n=6). (I) qRT-PCR analysis to monitor the total ZIKV vRNA in the supernatant of hNPC cultures at 72 h after ZIKV infection with or without drug treatment. (J) Vero cell reinfection assay to monitor the ZIKV infectious particles in the supernatant of hNPC cultures with or without drug treatment. To perform the Vero cell reinfection assay, hNPCs at 72 h after ZIKV infection were washed three times and changed to drug free medium for an additional 24 h. Vero cells were infected with the supernatant collected from hNPCs for 2 h and changed to virus free medium for an additional 24 h. Vero cells were stained with antibody against ZIKV E and DAPI. Scale bars, 200 µm. (n=3). (K) Quantification of ZIKV infectious particles produced by ZIKV-infected hNPCs with or without compound treatment by the Vero cell reinfection assay. (L) Heatmap analysis of mock-infected hNPCs treated with DMSO (mock); mock infected hNPCs treated with 25 µM HH (HH), mock-infected hNPCs treated with 15 µM AQ (AQ), ZIKV (MR766 strain, MOI=0.125) infected hNPCs treated with DMSO (ZIKV+DMSO); ZIKV-infected hNPCs treated with 25 µM HH (ZIKV+HH), and ZIKV-infected hNPCs treated with 15 µM AQ (ZIKV+AQ). Genes were selected from the up/down-regulated genes (fold change >4) in ZIKV-infected hNPCs treated with DMSO compared to mock-infected hNPCs treated with DMSO. (M and N) Immunocytochemistry analysis (M) and quantification of the infection rate (N) of hNPCs at 72 h after ZIKV (PRVABC59 strain) infection with or without drug treatment (n=6). Scale bars, 100 µm. p values were calculated by one-way repeated measures ANOVA with a Bonferroni test for multiple comparisons. $*p<0.05$, $p<0.01$ and $*p<0.001$.
Figure 1:
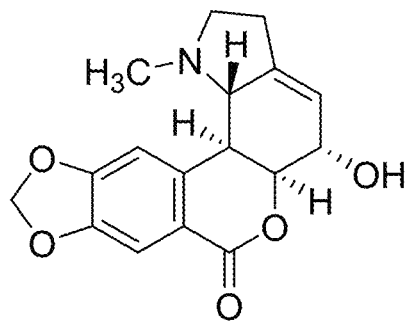
Figure 1:
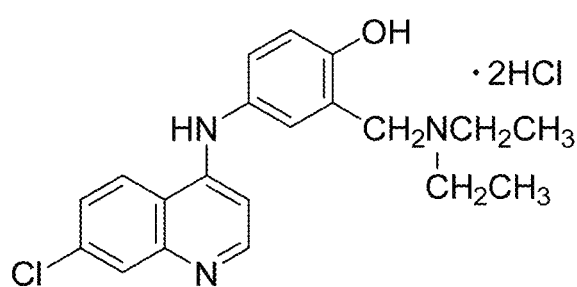
Figure 1:
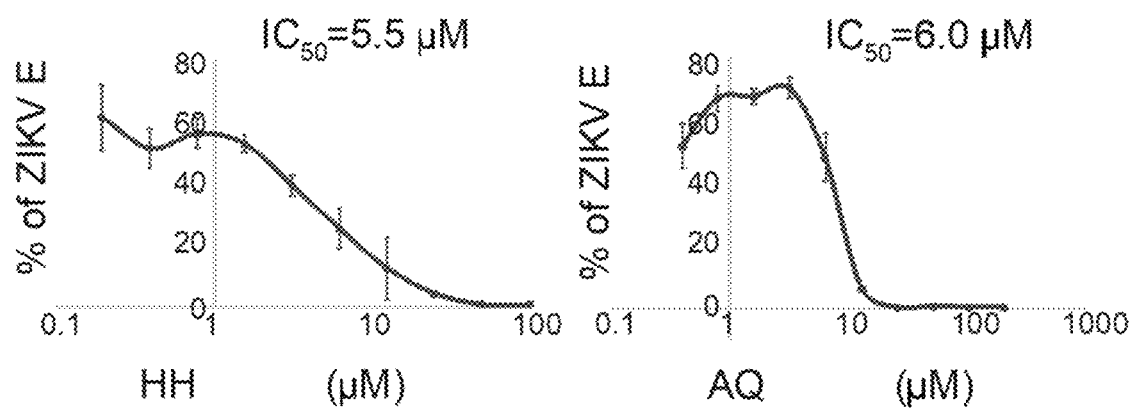
Figure 1:
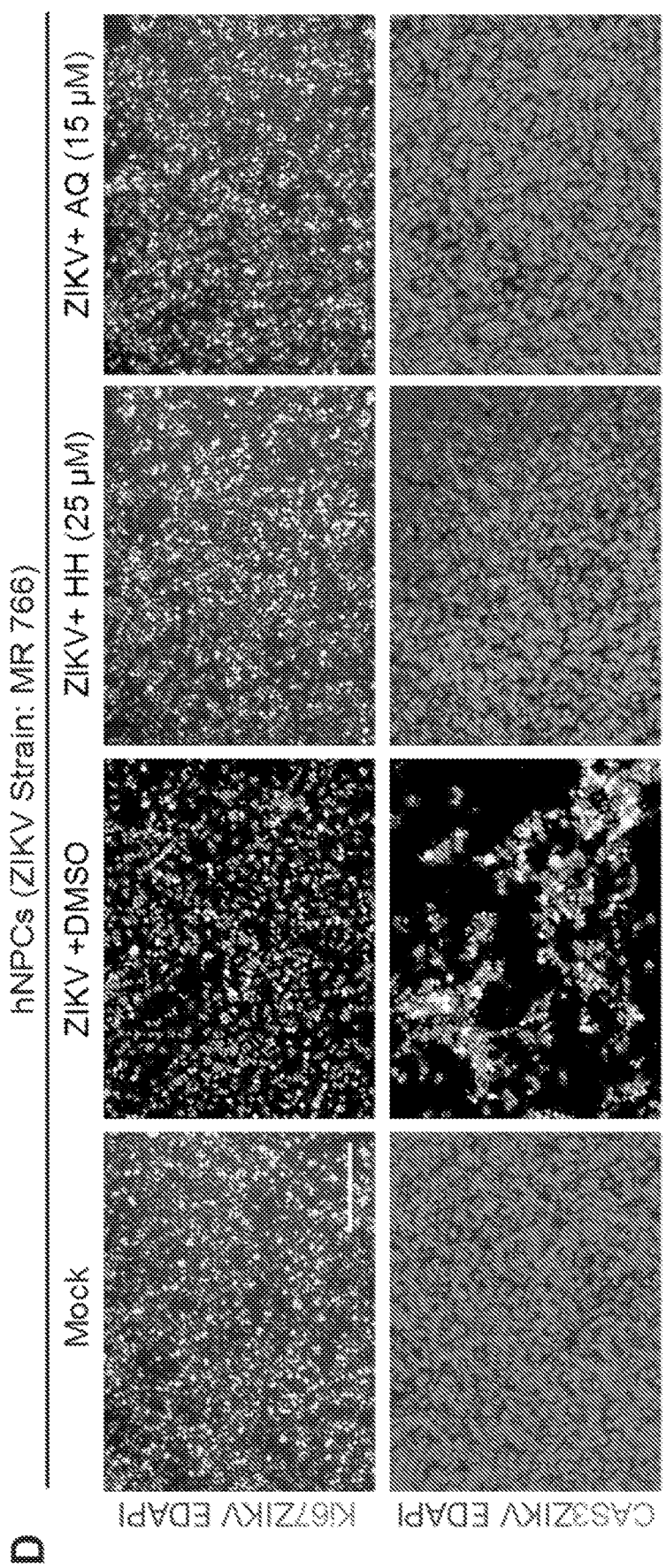
Figure 1:
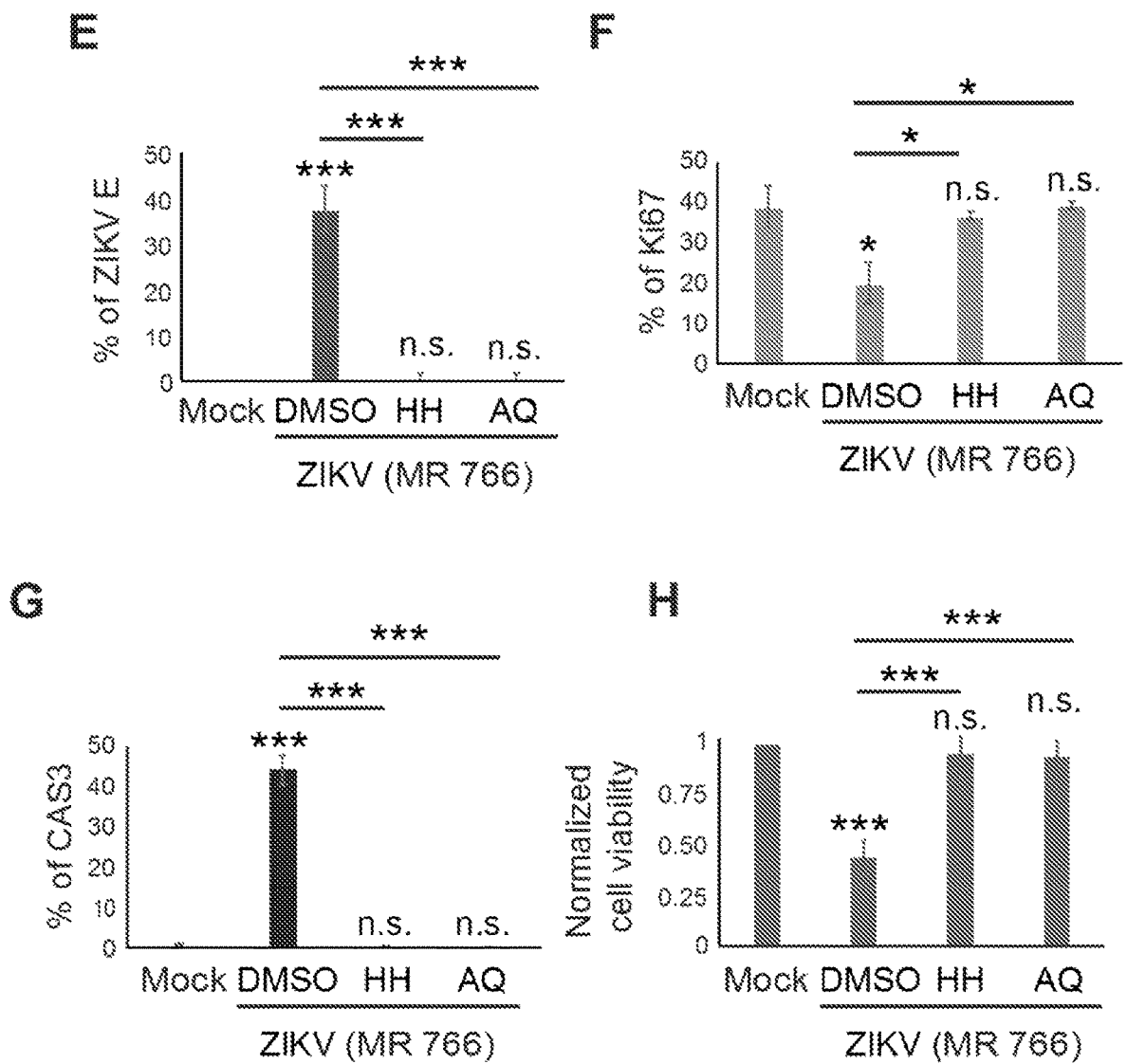
Figure 1:
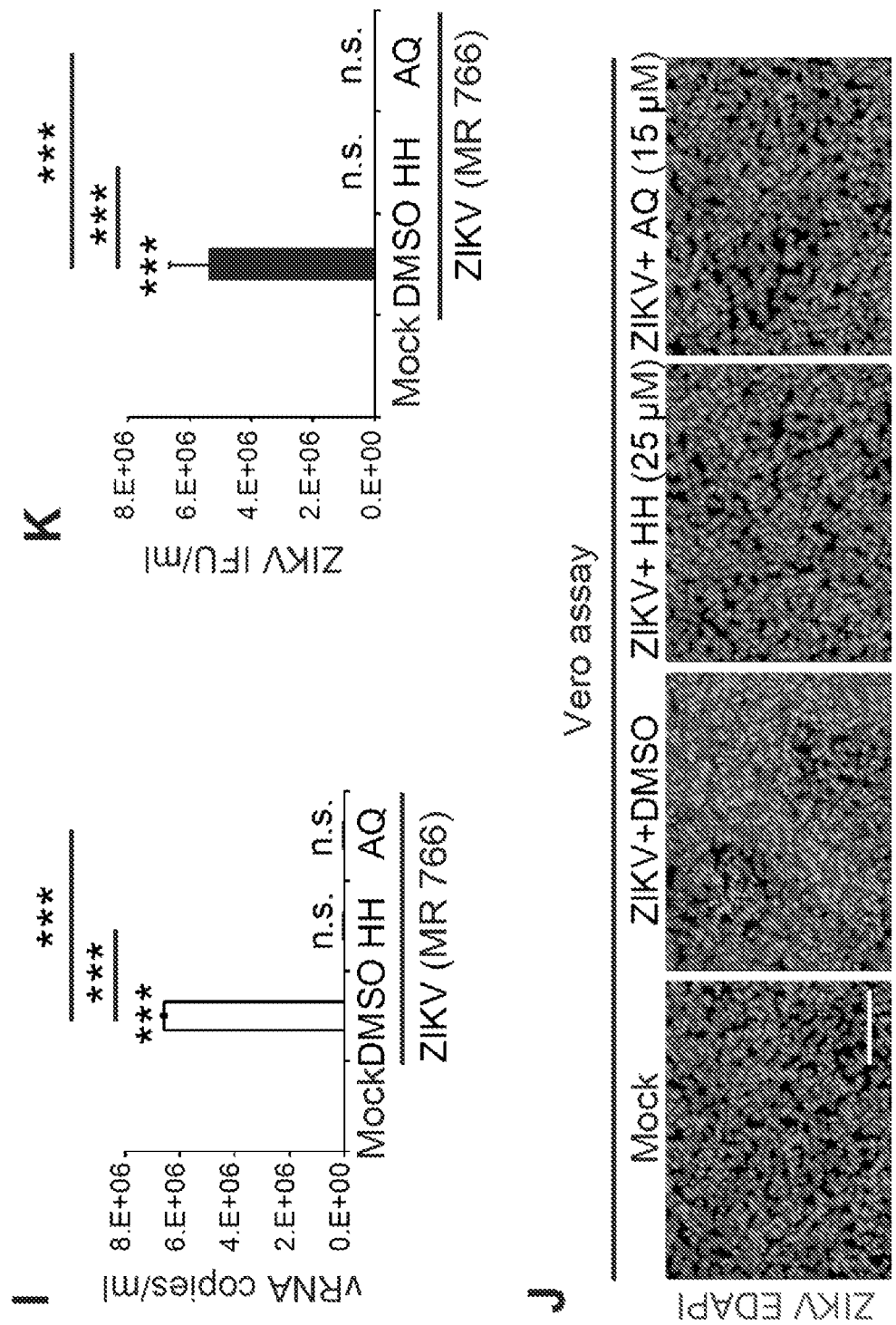
Figure 1:
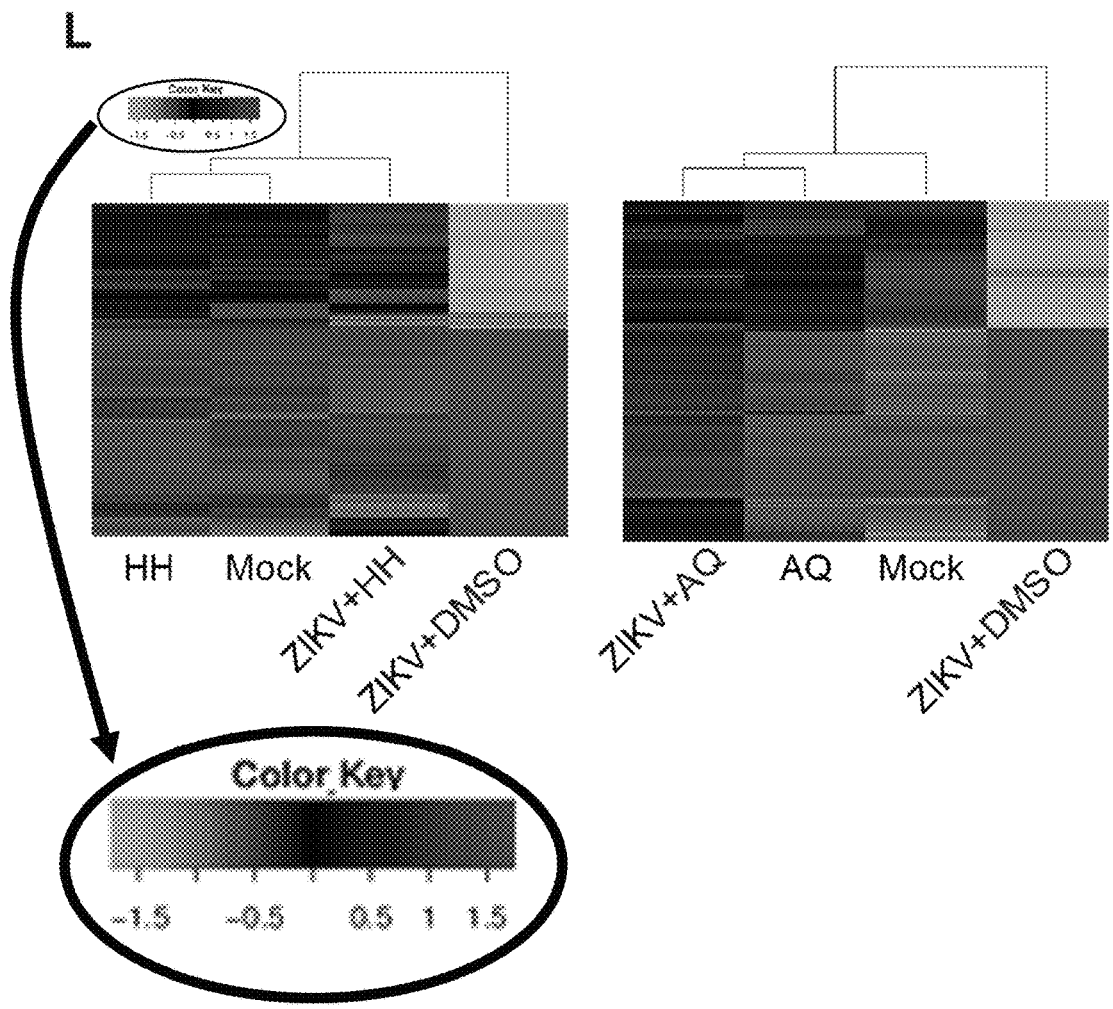
Figure 1:
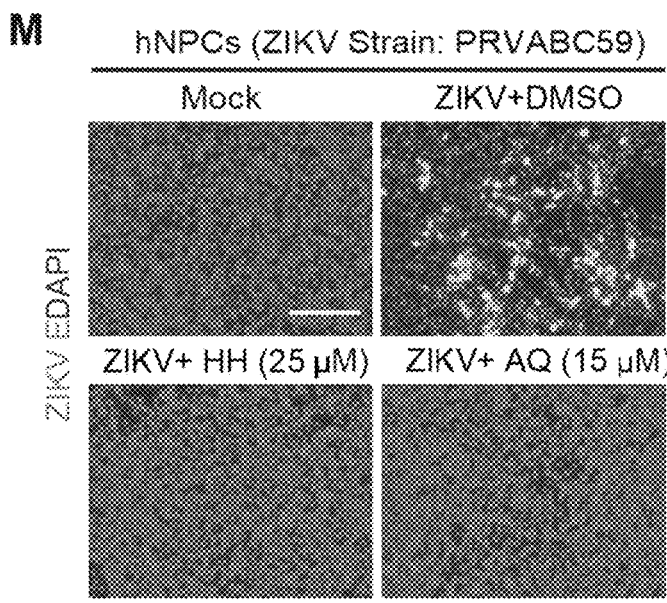
Figure 1:
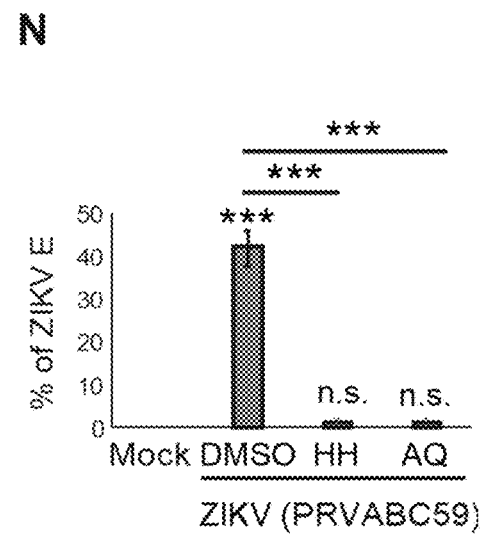

The present disclosure provides for identification of compounds for the inhibition and/or elimination of Zika virus (ZIKV), such as inhibition and/or elimination of Zika virus from the system of a subject. The compounds can be used in compositions that can be used for treatment of subjects who have been infected with the Zika virus or who are at risk of being infected with the Zika virus. Thus, the compositions can be used for prophylactic and/or therapeutic purposes. The compositions can comprise the active compounds as described herein and other excipients and stabilizers and the like. Such additives are well known in the art.

As used herein, unless otherwise stated, the term "group" refers to a chemical entity that has one terminus that can be covalently bonded to other chemical species. Examples of groups include, but are not limited to:

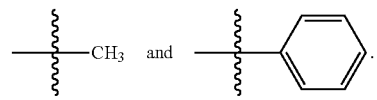

As used herein, unless otherwise stated, the term "moiety" refers to a chemical entity that has two or more termini that can be covalently bonded to other chemical species. Examples of moieties include, but are not limited to:

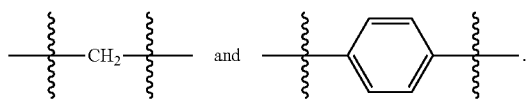

As used herein, unless otherwise indicated, the term "aliphatic" refers to branched or unbranched hydrocarbon groups that, optionally, contain one or more degrees of unsaturation. Degrees of unsaturation include, but are not limited to, alkenyl groups/moieties, alkynyl groups/moieties, and cyclic aliphatic groups/moieties. For example, the aliphatic group can be a $C_1$ to $C_8$, including all integer numbers of carbons and ranges of numbers of carbons therebetween (e.g., $C_1$, $C_2$, $C_3$, $C_4$, $C_5$, $C_6$, $C_7$, and $C_8$) aliphatic group. The aliphatic group can be unsubstituted or substituted with one or more substituent. Examples of substituents include, but are not limited to, various substituents such as, for example, halogens (—F, —Cl, —Br, and —I), additional aliphatic groups (e.g., alkenes, alkynes), aryl groups, alkoxides, amine groups, carboxylates, carboxylic acids, ether groups, diazirine groups, and the like, and combinations thereof.

As used herein, unless otherwise indicated, the term "alkyl" refers to branched or unbranched saturated hydrocarbon groups. Examples of alkyl groups include, but are not limited to, methyl groups, ethyl groups, propyl groups, butyl groups, isopropyl groups, tert-butyl groups, and the like. For example, the alkyl group can be a $C_1$ to $C_8$, including all integer numbers of carbons and ranges of numbers of carbons therebetween (e.g., $C_1$, $C_2$, $C_3$, $C_4$, $C_5$, $C_6$, $C_7$, and $C_8$), alkyl group. The alkyl group can be unsubstituted or substituted with one or more substituent. Examples of substituents include, but are not limited to, various substituents such as, for example, halogens (—F, —Cl, —Br, and —I), aliphatic groups (e.g., alkyl groups, alkenyl groups, alkynyl groups), aryl groups, alkoxide groups, amine groups, carboxylate groups, carboxylic acids, ether groups, diazirine groups, and the like, and combinations thereof.

As used herein, unless otherwise indicated, the term "aryl" refers to $C_5$ to $C_{14}$, including all integer numbers of carbons and ranges of numbers of carbons therebetween, aromatic or partially aromatic carbocyclic groups. The aryl group can comprise polyaryl moieties such as, for example, fused rings or biaryl moieties. The aryl group can be unsubstituted or substituted with one or more substituent. Examples of substituents include, but are not limited to, various substituents such as, for example, halogens (—F, —Cl, —Br, and —I), aliphatic groups (e.g., alkenes, alkynes), aryl groups, alkoxides, carboxylates, carboxylic acids, ether groups, and the like, and combinations thereof. Examples of aryl groups include, but are not limited to, phenyl groups, biaryl groups (e.g., biphenyl groups), and fused ring groups (e.g., naphthyl groups).

As used herein, unless otherwise indicated, the term "linking moiety" (also referred to as a linker) refers to a moiety linking two groups together, two moieties together, or a combination thereof. An example of a linking moiety is polyethylene glycol (PEG), having the following structure:

where n is 2-5, including all values and ranges therebetween (e.g., 2, 3, 4, and 5).

Zika virus (ZIKV) infects fetal and adult human brains, and is associated with serious neurological complications including microcephaly and Guillain-Barré Syndrome (GBS). A high content chemical screen was performed using a library containing FDA-approved drugs or drug candidates. Two compounds, hippeastrine hydrobromide (HH) and amodiaquine dihydrochloride dihydrate (AQ), were discovered to inhibit ZIKV infection in human cortical neuron progenitor cells (hNPCs). HH inhibited ZIKV infection and rescued ZIKV-induced growth and differentiation defects in hNPCs and human fetal-like forebrain organoids. Finally, HH and AQ inhibited ZIKV infection in adult mouse brain in vivo. Strikingly, HH suppressed virus propagation when administered to adult mice carrying replicating ZIKV, highlighting its therapeutic potential. This disclosure identifies drug candidates for treatment of ZIKV infection and ZIKV-related neurological complications in fetal and adult patients.

Examples of active compounds include, but are not limited to, hippeastrine hydrobromide (HH) and amodiaquine dihydrochloride dihydrate (AQ), and also include their derivatives. In an example, compounds of the present disclosure have similar or improved biological activities against the Zika virus. HH has the following structure:

In an aspect, the present disclosure provides compounds. The compounds can be used to treat (e.g., therapeutically or prophylactically) a subject for Zika infection, which may be pharmaceutically acceptable salts.

In an example, the compound has the following structure:

where R and $R^1$ are independently selected from H; $C_1$ to $C_8$ (e.g., $C_1$, $C_2$, $C_3$, $C_4$, $C_5$, $C_6$, $C_7$, and $C_8$) acyl aliphatic groups; $C_1$ to $C_8$ (e.g., $C_1$, $C_2$, $C_3$, $C_4$, $C_5$, $C_6$, $C_7$, and $C_8$) carbamide aliphatic groups; $C_1$ to $C_8$ (e.g., $C_1$, $C_2$, $C_3$, $C_4$, $C_5$, $C_6$, $C_7$, and $C_8$) amide aliphatic groups; $C_1$ to $C_8$ (e.g., $C_1$, $C_2$, $C_3$, $C_4$, $C_5$, $C_6$, $C_7$, and $C_8$) aliphatic groups; $C_1$ to $C_8$ (e.g., $C_1$, $C_2$, $C_3$, $C_4$, $C_5$, $C_6$, $C_7$, and $C_8$) acyl aliphatic aryl groups, where $C_1$ to $C_8$ refers to the length of the aliphatic portion of the acyl aliphatic aryl group, $C_1$ to $C_8$ (e.g., $C_1$, $C_2$, $C_3$, $C_4$, $C_5$, $C_6$, $C_7$, and $C_8$) carbamide aliphatic aryl groups, where $C_1$ to $C_8$ refers to the length of the aliphatic portion of the carbamide aliphatic aryl group; or $C_1$ to $C_8$ (e.g., $C_1$, $C_2$, $C_3$, $C_4$, $C_5$, $C_6$, $C_7$, and $C_8$) amide aliphatic aryl groups, where $C_1$ to $C_8$ refers to the length of the aliphatic portion of the amide aliphatic aryl group; or R and $R^1$ taken together form

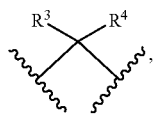

where $R^3$ and $R^4$ are independently selected from H and $C_1$ to $C_8$ (e.g., $C_1$, $C_2$, $C_3$, $C_4$, $C_5$, $C_6$, $C_7$, and $C_8$) aliphatic groups; and where $R^2$ is selected from H; $C_1$ to $C_8$ (e.g., $C_1$, $C_2$, $C_3$, $C_4$, $C_5$, $C_6$, $C_7$, and $C_8$) acyl aliphatic groups; $C_1$ to $C_8$ (e.g., $C_1$, $C_2$, $C_3$, $C_4$, $C_5$, $C_6$, $C_7$, and $C_8$) carbamide aliphatic groups; $C_1$ to $C_8$ (e.g., $C_1$, $C_2$, $C_3$, $C_4$, $C_5$, $C_6$, $C_7$, and $C_8$) amide aliphatic groups; $C_1$ to $C_8$ (e.g., $C_1$, $C_2$, $C_3$, $C_4$, $C_5$, $C_6$, $C_7$, and $C_8$) acyl aromatic groups; $C_1$ to $C_8$ (e.g., $C_1$, $C_2$, $C_3$, $C_4$, $C_5$, $C_6$, $C_7$, and $C_8$) carbamide aryl groups; or $C_1$ to $C_8$ (e.g., $C_1$, $C_2$, $C_3$, $C_4$, $C_5$, $C_6$, $C_7$, and $C_8$) amide aryl groups, or $R^2$ has the following structure:

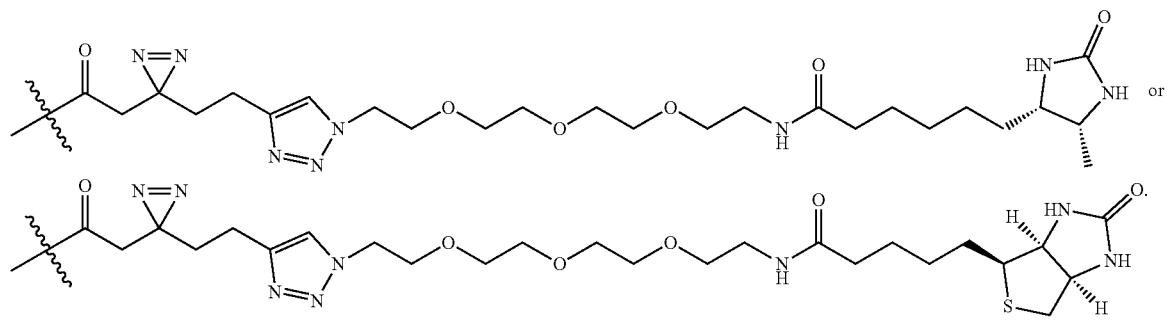

For example, a compound of the present disclosure has the following structure:

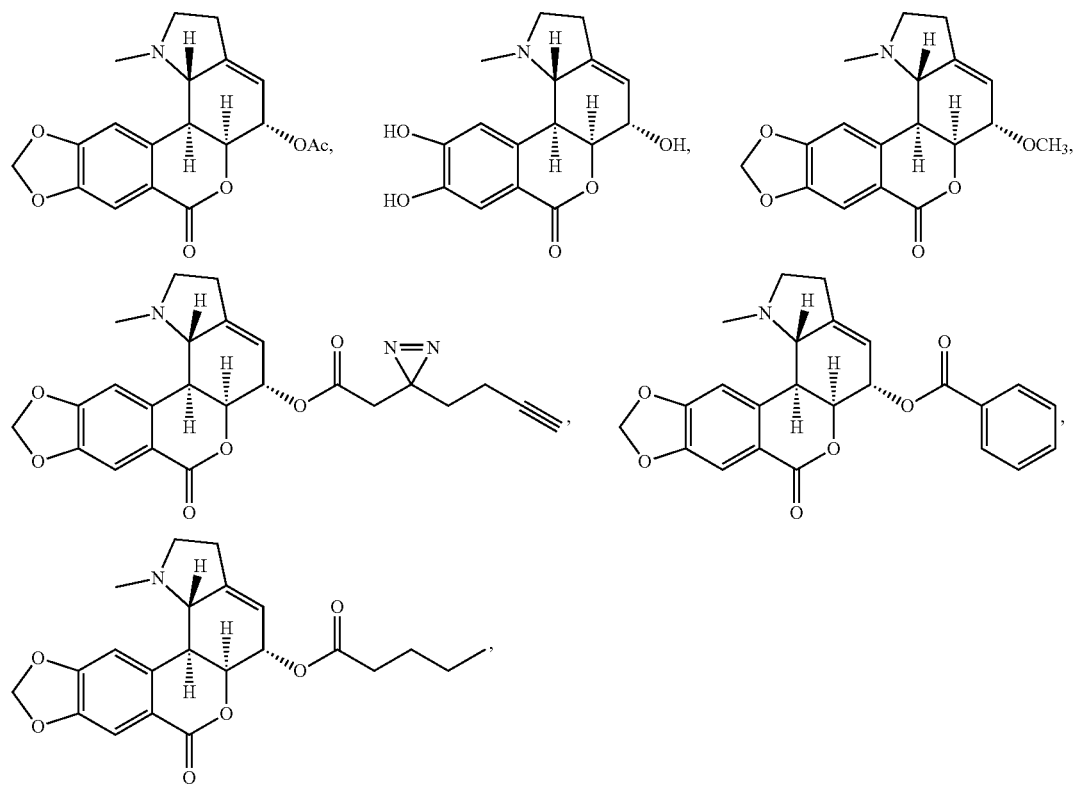

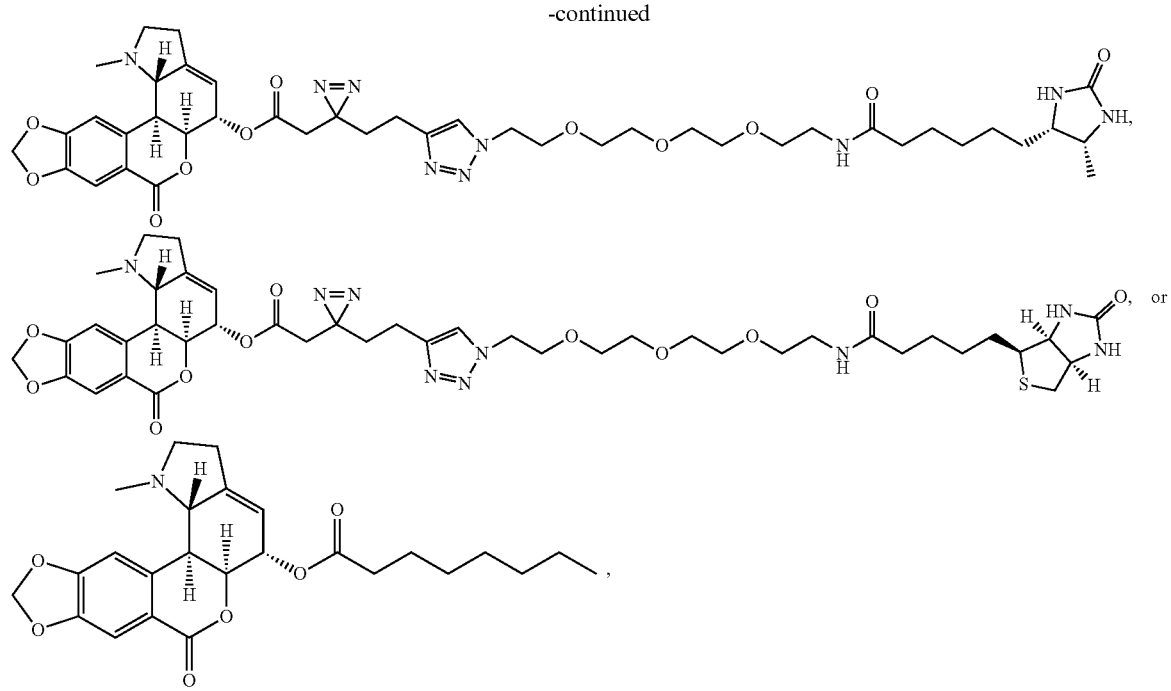

In an example, the compound is not HH.

In another example, the compound has the following structure:

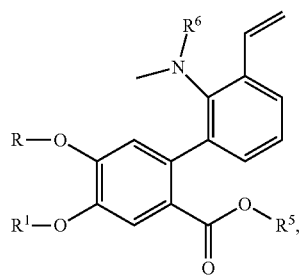

where R and R¹ are independently selected from H; $C_1$ to $C_8$ (e.g., $C_1$, $C_2$, $C_3$, $C_4$, $C_5$, $C_6$, $C_7$, and $C_8$) acyl aliphatic groups; $C_1$ to $C_8$ (e.g., $C_1$, $C_2$, $C_3$, $C_4$, $C_5$, $C_6$, $C_7$, and $C_8$) carbamide aliphatic groups; $C_1$ to $C_8$ (e.g., $C_1$, $C_2$, $C_3$, $C_4$, $C_5$, $C_6$, $C_7$, and $C_8$) amide aliphatic groups; $C_1$ to $C_8$ (e.g., $C_1$, $C_2$, $C_3$, $C_4$, $C_5$, $C_6$, $C_7$, and $C_8$) aliphatic groups; $C_1$ to $C_8$ (e.g., $C_1$, $C_2$, $C_3$, $C_4$, $C_5$, $C_6$, $C_7$, and $C_8$) acyl aliphatic aryl groups, where $C_1$ to $C_8$ refers to the length of the aliphatic portion of the acyl aliphatic aryl group; $C_1$ to $C_8$ (e.g., $C_1$, $C_2$, $C_3$, $C_4$, $C_5$, $C_6$, $C_7$, and $C_8$) carbamide aliphatic aryl groups, where $C_1$ to $C_8$ refers to the length of the aliphatic portion of the carbamide aliphatic aryl group; or $C_1$ to $C_8$ (e.g., $C_1$, $C_2$, $C_3$, $C_4$, $C_5$, $C_6$, $C_7$, and $C_8$) amide aliphatic aryl groups, where $C_1$ to $C_8$ refers to the length of the aliphatic portion of the amide aliphatic aryl group; or R and R¹ taken together form

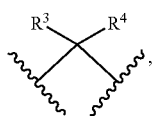

where R³ and R⁴ are independently selected from H and $C_1$ to $C_8$ (e.g., $C_1$, $C_2$, $C_3$, $C_4$, $C_5$, $C_6$, $C_7$, and $C_8$) aliphatic groups; where R⁵ is selected from H and $C_1$ to $C_8$ (e.g., $C_1$, $C_2$, $C_3$, $C_4$, $C_5$, $C_6$, $C_7$, and $C_8$) aliphatic groups, or R⁵ has the following structure:

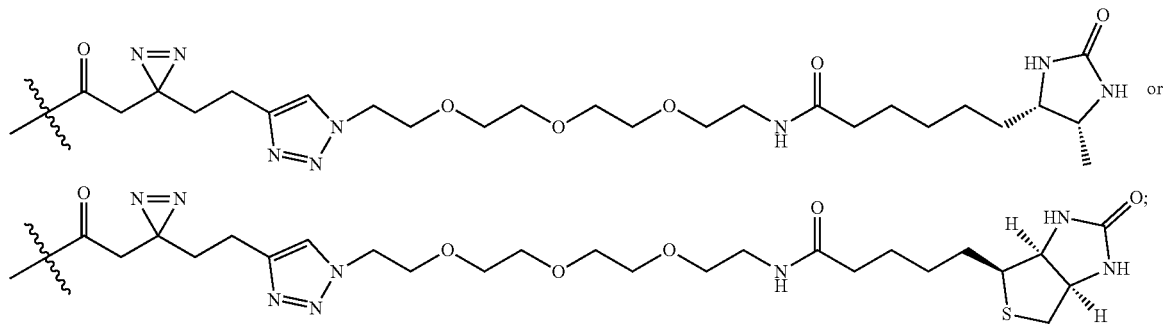

and $R^6$ is selected from H and $C_1$ to $C_8$ (e.g., $C_1$, $C_2$, $C_3$, $C_4$, $C_5$, $C_6$, $C_7$, and $C_8$) aliphatic groups.

In another example, the compound has the following structure:

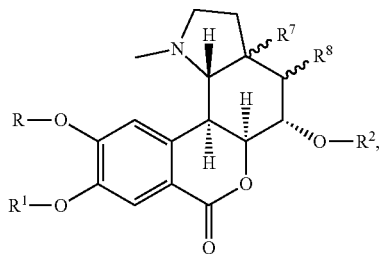

where R and R' are independently selected from H; $C_1$ to $C_8$ (e.g., $C_1$, $C_2$, $C_3$, $C_4$, $C_5$, $C_6$, $C_7$, and $C_8$) acyl aliphatic groups; $C_1$ to $C_8$ (e.g., $C_1$, $C_2$, $C_3$, $C_4$, $C_5$, $C_6$, $C_7$, and $C_8$) carbamide aliphatic groups; $C_1$ to $C_8$ (e.g., $C_1$, $C_2$, $C_3$, $C_4$, $C_5$, $C_6$, $C_7$, and $C_8$) amide aliphatic groups, $C_1$ to $C_8$ (e.g., $C_1$, $C_2$, $C_3$, $C_4$, $C_5$, $C_6$, $C_7$, and $C_8$) aliphatic groups; $C_1$ to $C_8$ (e.g., $C_1$, $C_2$, $C_3$, $C_4$, $C_5$, $C_6$, $C_7$, and $C_8$) acyl aliphatic aryl groups, where $C_1$ to $C_8$ (e.g., $C_1$, $C_2$, $C_3$, $C_4$, $C_5$, $C_6$, $C_7$, and $C_8$) refers to the length of the aliphatic portion of the acyl aliphatic aryl group, $C_1$ to $C_8$ (e.g., $C_1$, $C_2$, $C_3$, $C_4$, $C_5$, $C_6$, $C_7$, and $C_8$) carbamide aliphatic aryl groups, where $C_1$ to $C_8$ refers to the length of the aliphatic portion of the carbamide aliphatic aryl group; or $C_1$ to $C_8$ (e.g., $C_1$, $C_2$, $C_3$, $C_4$, $C_5$, $C_6$, $C_7$, and $C_8$) amide aliphatic aryl groups, where $C_1$ to $C_8$ refers to the length of the aliphatic portion of the amide aliphatic aryl group, or R and $R^1$ taken together form $$\begin{array}{c} R^3 \quad R^4 \\ \text{\textasciitilde} \diagup \text{\textasciitilde} \end{array},$$

where $R^3$ and $R^4$ are independently selected from H and $C_1$ to $C_8$ (e.g., $C_1$, $C_2$, $C_3$, $C_4$, $C_5$, $C_6$, $C_7$, and $C_8$) aliphatic groups; where $R^2$ is selected from H; $C_1$ to $C_8$ (e.g., $C_1$, $C_2$, $C_3$, $C_4$, $C_5$, $C_6$, $C_7$, and $C_8$) acyl aliphatic groups; $C_1$ to $C_8$ (e.g., $C_1$, $C_2$, $C_3$, $C_4$, $C_5$, $C_6$, $C_7$, and $C_8$) carbamide aliphatic groups; $C_1$ to $C_8$ (e.g., $C_1$, $C_2$, $C_3$, $C_4$, $C_5$, $C_6$, $C_7$, and $C_8$) amide aliphatic groups; $C_1$ to $C_8$ (e.g., $C_1$, $C_2$, $C_3$, $C_4$, $C_5$, $C_6$, $C_7$, and $C_8$) acyl aromatic groups; $C_1$ to $C_8$ (e.g., $C_1$, $C_2$, $C_3$, $C_4$, $C_5$, $C_6$, $C_7$, and $C_8$) carbamide aryl groups; or $C_1$ to $C_8$ amide aryl groups, or $R^2$ has the following structure:

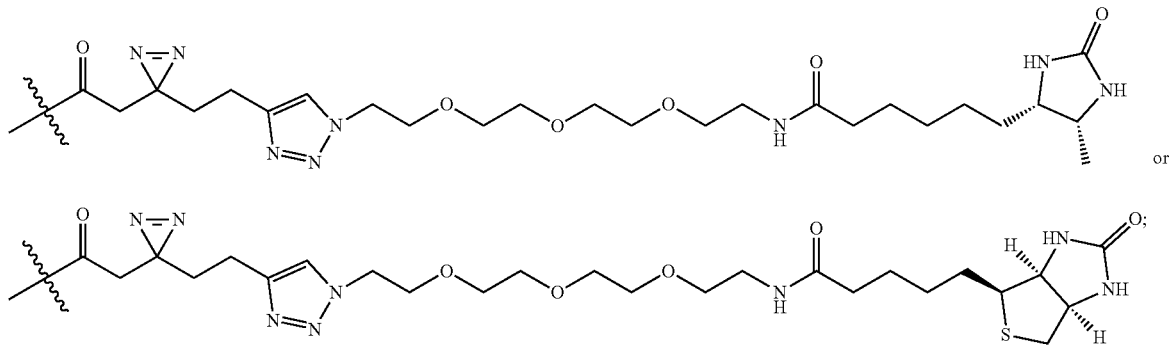

$R^7$ is H, where the stereochemistry is R or S; and $R^8$ is H, where the stereochemistry is R or S. For example, a compound of the present disclosure has the following structure:

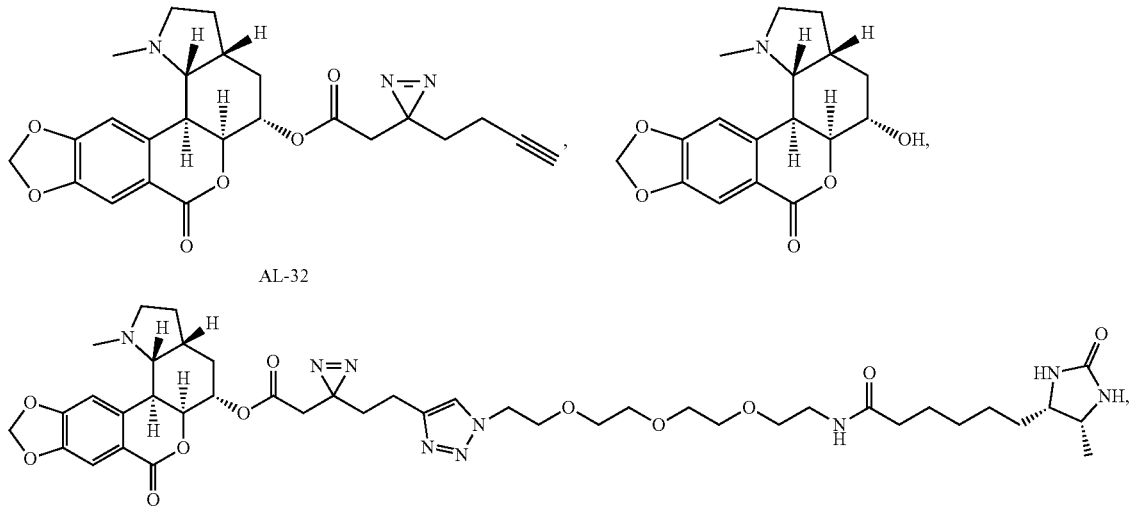

AL-32

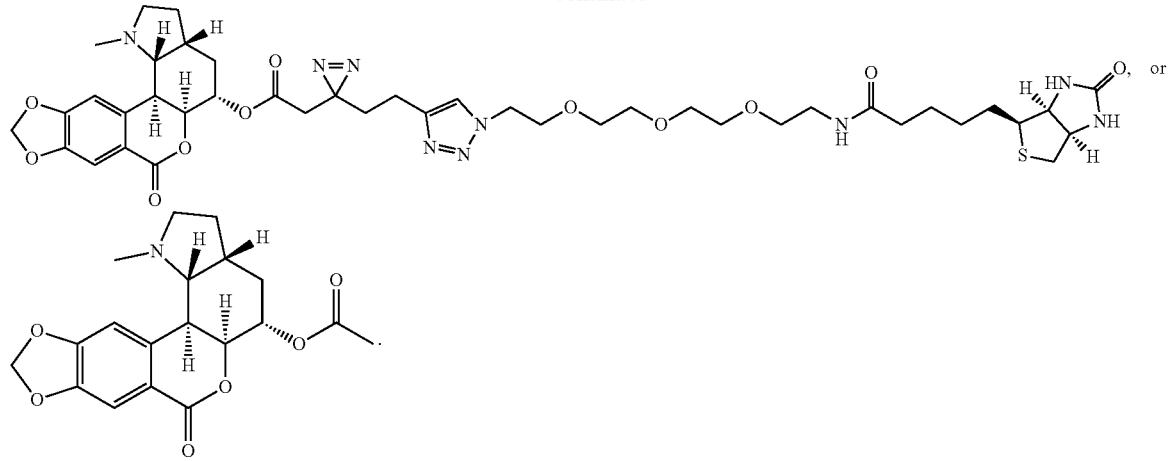

In another example, the compound has the following structure:

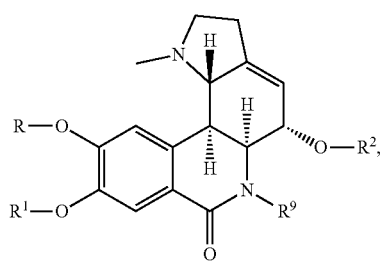

where R and $R^1$ are independently selected from H; $C_1$ to $C_8$ (e.g., $C_1$, $C_2$, $C_3$, $C_4$, $C_5$, $C_6$, $C_7$, and $C_8$) acyl aliphatic groups; $C_1$ to $C_8$ (e.g., $C_1$, $C_2$, $C_3$, $C_4$, $C_5$, $C_6$, $C_7$, and $C_8$) carbamide aliphatic groups; $C_1$ to $C_8$ (e.g., $C_1$, $C_2$, $C_3$, $C_4$, $C_5$, $C_6$, $C_7$, and $C_8$) amide aliphatic groups; $C_1$ to $C_8$ (e.g., $C_1$, $C_2$, $C_3$, $C_4$, $C_5$, $C_6$, $C_7$, and $C_8$) aliphatic groups; $C_1$ to $C_8$ (e.g., $C_1$, $C_2$, $C_3$, $C_4$, $C_5$, $C_6$, $C_7$, and $C_8$) acyl aliphatic aryl groups, where $C_1$ to $C_8$ refers to the length of the aliphatic portion of the acyl aliphatic aryl group; $C_1$ to $C_8$ (e.g., $C_1$, $C_2$, $C_3$, $C_4$, $C_5$, $C_6$, $C_7$, and $C_8$) carbamide aliphatic aryl groups, where $C_1$ to $C_8$ refers to the length of the aliphatic portion of the carbamide aliphatic aryl group; or $C_1$ to $C_8$ (e.g., $C_1$, $C_2$, $C_3$, $C_4$, $C_5$, $C_6$, $C_7$, and $C_8$) amide aliphatic aryl groups, where $C_1$ to $C_8$ refers to the length of the aliphatic portion of the amide aliphatic aryl group; or R and $R^1$ taken together form

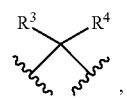

where $R^3$ and $R^4$ are independently selected from H and $C_1$ to $C_8$ (e.g., $C_1$, $C_2$, $C_3$, $C_4$, $C_5$, $C_6$, $C_7$, and $C_8$) aliphatic groups; where $R^2$ is selected from H; $C_1$ to $C_8$ (e.g., $C_1$, $C_2$, $C_3$, $C_4$, $C_5$, $C_6$, $C_7$, and $C_8$) acyl aliphatic groups; $C_1$ to $C_8$ (e.g., $C_1$, $C_2$, $C_3$, $C_4$, $C_5$, $C_6$, $C_7$, and $C_8$) carbamide aliphatic groups; $C_1$ to $C_8$ (e.g., $C_1$, $C_2$, $C_3$, $C_4$, $C_5$, $C_6$, $C_7$, and $C_8$) carbamide aliphatic groups; $C_1$ to $C_8$ (e.g., $C_1$, $C_2$, $C_3$, $C_4$, $C_5$, $C_6$, $C_7$, and $C_8$) acyl aromatic groups; $C_1$ to $C_8$ (e.g., $C_1$, $C_2$, $C_3$, $C_4$, $C_5$, $C_6$, $C_7$, and $C_8$) carbamide aryl groups; or $C_1$ to $C_8$ (e.g., $C_1$, $C_2$, $C_3$, $C_4$, $C_5$, $C_6$, $C_7$, and $C_8$) amide aryl groups; and $R^9$ is a $C_1$ to $C_8$ (e.g., $C_1$, $C_2$, $C_3$, $C_4$, $C_5$, $C_6$, $C_7$, and $C_8$) aliphatic group.

In another example, the compound has the following structure:

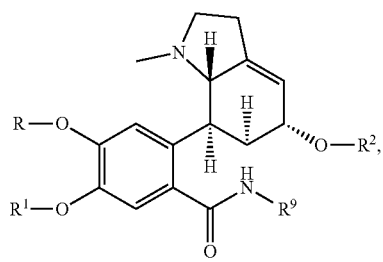

where R and $R^1$ are independently selected from H; $C_1$ to $C_8$ (e.g., $C_1$, $C_2$, $C_3$, $C_4$, $C_5$, $C_6$, $C_7$, and $C_8$) acyl aliphatic groups; $C_1$ to $C_8$ (e.g., $C_1$, $C_2$, $C_3$, $C_4$, $C_5$, $C_6$, $C_7$, and $C_8$) carbamide aliphatic groups; $C_1$ to $C_8$ (e.g., $C_1$, $C_2$, $C_3$, $C_4$, $C_5$, $C_6$, $C_7$, and $C_8$) amide aliphatic groups; $C_1$ to $C_8$ (e.g., $C_1$, $C_2$, $C_3$, $C_4$, $C_5$, $C_6$, $C_7$, and $C_8$) aliphatic groups; $C_1$ to $C_8$ (e.g., $C_1$, $C_2$, $C_3$, $C_4$, $C_5$, $C_6$, $C_7$, and $C_8$) acyl aliphatic aryl groups, where $C_1$ to $C_8$ refers to the length of the aliphatic portion of the acyl aliphatic aryl group; $C_1$ to $C_8$ (e.g., $C_1$, $C_2$, $C_3$, $C_4$, $C_5$, $C_6$, $C_7$, and $C_8$) carbamide aliphatic aryl groups, where $C_1$ to $C_8$ refers to the length of the aliphatic portion of the carbamide aliphatic aryl group; or $C_1$ to $C_8$ (e.g., $C_1$, $C_2$, $C_3$, $C_4$, $C_5$, $C_6$, $C_7$, and $C_8$) amide aliphatic aryl groups, where $C_1$ to $C_8$ refers to the length of the aliphatic portion of the amide aliphatic aryl group; or R and $R^1$ taken together form

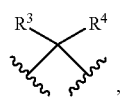

where $R^3$ and $R^4$ are independently selected from H and $C_1$ to $C_8$ (e.g., $C_1$, $C_2$, $C_3$, $C_4$, $C_5$, $C_6$, $C_7$, and $C_8$) aliphatic groups; where $R^2$ is selected from H; $C_1$ to $C_8$ (e.g., $C_1$, $C_2$, $C_3$, $C_4$, $C_5$, $C_6$, $C_7$, and $C_8$) acyl aliphatic groups; $C_1$ to $C_8$ (e.g., $C_1$, $C_2$, $C_3$, $C_4$, $C_5$, $C_6$, $C_7$, and $C_8$) carbamide aliphatic groups; $C_1$ to $C_8$ (e.g., $C_1$, $C_2$, $C_3$, $C_4$, $C_5$, $C_6$, $C_7$, and $C_8$) amide aliphatic groups; $C_1$ to $C_8$ (e.g., $C_1$, $C_2$, $C_3$, $C_4$, $C_5$, $C_6$, $C_7$, and $C_8$) acyl aromatic groups; $C_1$ to $C_8$ (e.g., $C_1$, $C_2$, $C_3$, $C_4$, $C_5$, $C_6$, $C_7$, and $C_8$) carbamide aryl groups; or $C_1$ to $C_8$ (e.g., $C_1$, $C_2$, $C_3$, $C_4$, $C_5$, $C_6$, $C_7$, and $C_8$) amide aryl groups, or $R^2$ has the following structure:

of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate,

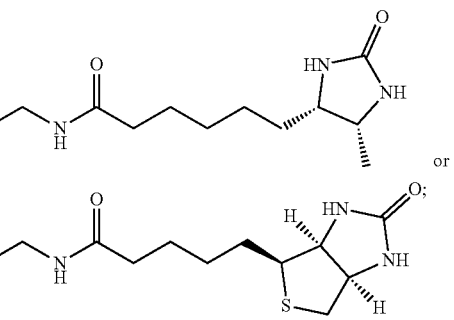

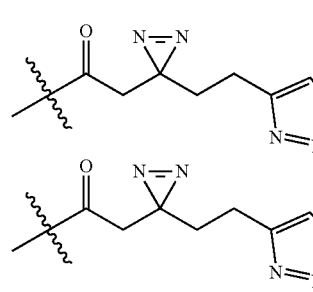

and $R^9$ is a $C_1$ to $C_8$ (e.g., $C_1$, $C_2$, $C_3$, $C_4$, $C_5$, $C_6$, $C_7$, and $C_8$) aliphatic group.

Any $R^2$ group herein may terminate with a functional group. The functional group can be reacted with another functional group to modify the $R^2$ group. Non-limiting examples of functional groups that $R^2$ can terminate with include: alkynes, azides, nucleophiles (e.g., thiols, amines, alcohols, alkoxides, and the like), and electrophiles (e.g., carboxylic acids, esters, aldehydes, epoxides, alkyl halides (e.g., —$CH_2Br$), carbocations, alkenes, and the like). The functional group is reacted with another functional group (e.g., alkynes, azides, nucleophiles (e.g., thiols, amines, alcohols, alkoxides, and the like), and electrophiles (e.g., carboxylic acids, esters, aldehydes, epoxides, alkyl halides (e.g., —$CH_2Br$), carbocations, alkenes, and the like)) attached (e.g., covalently bonded) to a pendant group (e.g., biotin or desthiobiotin). Non-limiting examples of such reactions include a nucleophilic reactions where a nucleophile (e.g., an amine) reacts with an electrophile (e.g., an ester) or a Click reaction between an azide and an alkyne. For example, a Click reaction can occur between the two functional groups (e.g., an $R^2$ group terminating with an alkyne and the pendant group terminating with an azide) such that the pendant group is attached (e.g., covalently bonded) to the $R^2$ group. In an example of a Click reaction, a pendant group (e.g., biotin or desthiobiotin) is attached (e.g., covalently bonded) to a linking moiety (e.g., a polyethylene glycol) that terminates with an azide that is reacted with the terminal alkyne of an $R^2$ of a compound of the present disclosure to form a triazole moiety.

Compounds of the disclosure can be in the form of salts. As used herein, the term "pharmaceutically acceptable salts" refers to salts of a compound of the present disclosure. Salts of compounds of the present disclosure can be prepared during the final isolation and purification of the compounds or separately, for example, by reacting the compound with an acid having a suitable cation. In an example, the pharmaceutically acceptable salts of a compound of the present disclosure are acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present disclosure appearing herein is intended to include pharmaceutically acceptable salts, hydrates, or prodrugs thereof.

In an aspect, the present disclosure provides compositions. The compositions comprise one or more compound (e.g., a combination of different compounds) of the present disclosure. The compositions may further comprise one or more pharmaceutically acceptable carrier, excipient, stabilizer, or combination thereof.

In an example, a composition of the present disclosure comprises one or more pharmaceutically acceptable carrier, excipient, stabilizer, or combination thereof and one or more compound having the following structure:

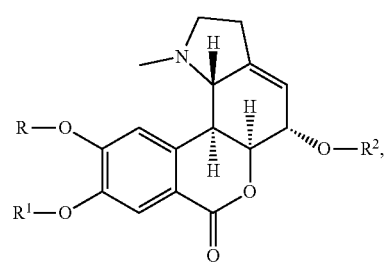

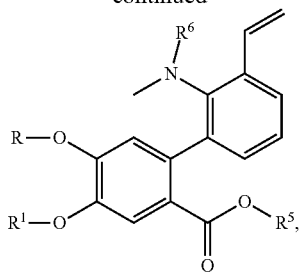

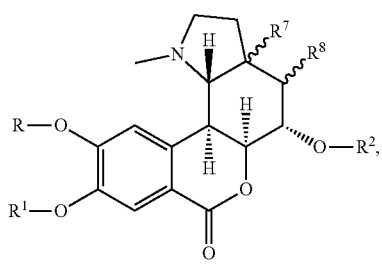

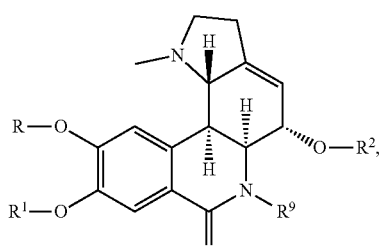

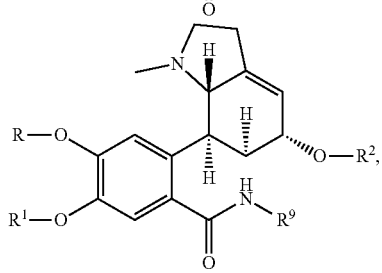

or combinations thereof;

where R and $R^1$ are independently selected from H; $C_1$ to $C_8$ (e.g., $C_1$, $C_2$, $C_3$, $C_4$, $C_5$, $C_6$, $C_7$, and $C_8$) acyl aliphatic groups; $C_1$ to $C_8$ (e.g., $C_1$, $C_2$, $C_3$, $C_4$, $C_5$, $C_6$, $C_7$, and $C_8$) carbamide aliphatic groups; $C_1$ to $C_8$ (e.g., $C_1$, $C_2$, $C_3$, $C_4$, $C_5$, $C_6$, $C_7$, and $C_8$) amide aliphatic groups; $C_1$ to $C_8$ (e.g., $C_1$, $C_2$, $C_3$, $C_4$, $C_5$, $C_6$, $C_7$, and $C_8$) aliphatic groups; $C_1$ to $C_8$ (e.g., $C_1$, $C_2$, $C_3$, $C_4$, $C_5$, $C_6$, $C_7$, and $C_8$) acyl aliphatic aryl groups, where $C_1$ to $C_8$ is the length of the aliphatic portion of the acyl aliphatic aryl group, $C_1$ to $C_8$ (e.g., $C_1$, $C_2$, $C_3$, $C_4$, $C_5$, $C_6$, $C_7$, and $C_8$) carbamide aliphatic aryl groups, wherein $C_1$ to $C_8$ is the length of the aliphatic portion of the carbamide aliphatic aryl group; or $C_1$ to $C_8$ (e.g., $C_1$, $C_2$, $C_3$, $C_4$, $C_5$, $C_6$, $C_7$, and $C_8$) amide aliphatic aryl groups, where $C_1$ to $C_8$ is the length of the aliphatic portion of the amide aliphatic aryl group; or R and $R^1$ taken together form

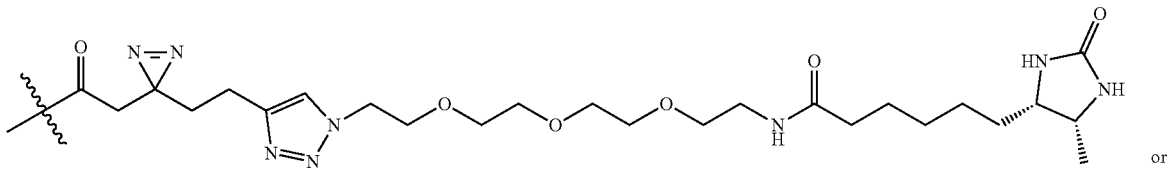

where $R^3$ and $R^4$ are independently selected from H and $C_1$ to $C_8$ (e.g., $C_1$, $C_2$, $C_3$, $C_4$, $C_5$, $C_6$, $C_7$, and $C_8$) aliphatic groups; where $R^2$ is selected from H; $C_1$ to $C_8$ (e.g., $C_1$, $C_2$, $C_3$, $C_4$, $C_5$, $C_6$, $C_7$, and $C_8$) acyl aliphatic groups; $C_1$ to $C_8$ (e.g., $C_1$, $C_2$, $C_3$, $C_4$, $C_5$, $C_6$, $C_7$, and $C_8$) carbamide aliphatic groups; $C_1$ to $C_8$ (e.g., $C_1$, $C_2$, $C_3$, $C_4$, $C_5$, $C_6$, $C_7$, and $C_8$) amide aliphatic groups; $C_1$ to $C_8$ (e.g., $C_1$, $C_2$, $C_3$, $C_4$, $C_5$, $C_6$, $C_7$, and $C_8$) acyl aromatic groups; $C_1$ to $C_8$ (e.g., $C_1$, $C_2$, $C_3$, $C_4$, $C_5$, $C_6$, $C_7$, and $C_8$) carbamide aryl groups; or $C_1$ to $C_8$ (e.g., $C_1$, $C_2$, $C_3$, $C_4$, $C_5$, $C_6$, $C_7$, and $C_8$) amide aryl groups, or $R^2$ has the following structure:

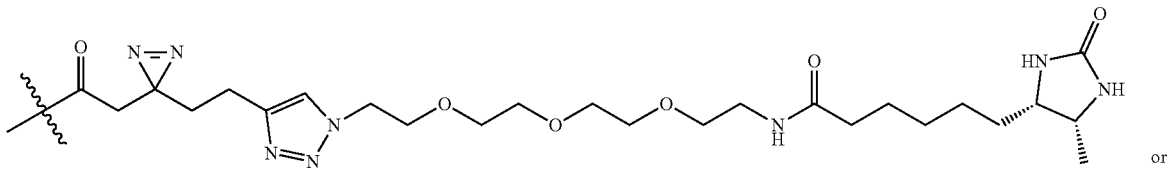

or

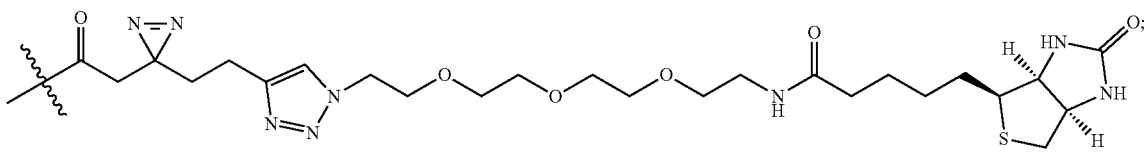

;

where R⁵ is selected from H and C₁ to C₈ (e.g., C₁, C₂, C₃, C₄, C₅, C₆, C₇, and C₈) aliphatic groups, or R⁵ has the following structure:

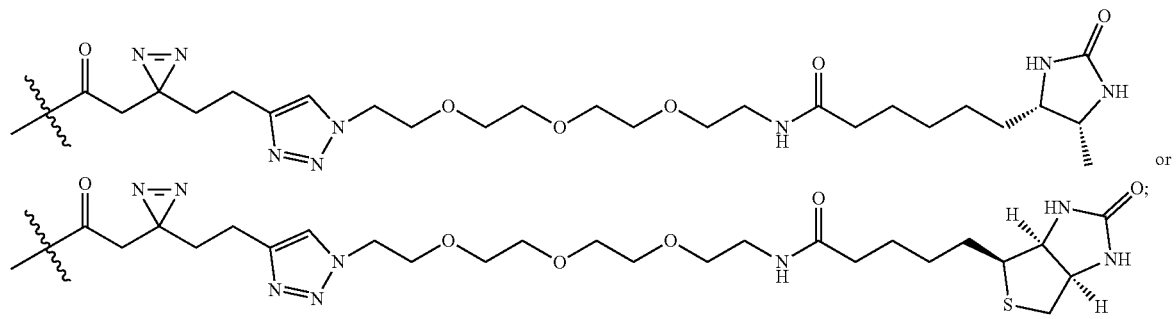

or where R⁶ is selected from H and C₁ to C₈ (e.g., C₁, C₂, C₃, C₄, C₅, C₆, C₇, and C₈) aliphatic groups; where R⁷ is H, where the stereochemistry is R or S; where R⁸ is H, where the stereochemistry is R or S; and where R⁹ is a C₁ to C₈ (e.g., C₁, C₂, C₃, C₄, C₅, C₆, C₇, and C₈) aliphatic group. For example, a compound of the present disclosure has the following structure:

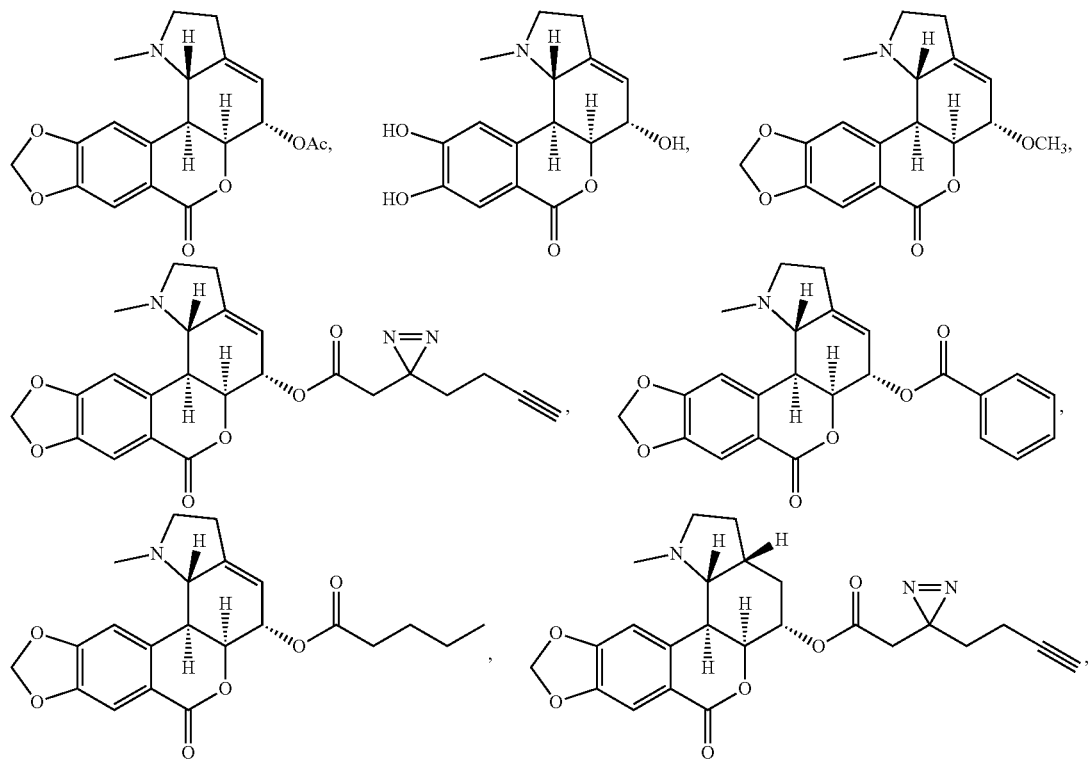

AL-32

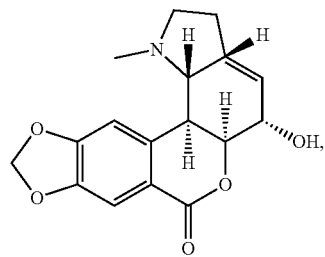

In an example, the compound is not HH.

The compositions can include one or more standard pharmaceutically acceptable carriers, excipients, stabilizers, or a combination thereof. Examples of pharmaceutically acceptable carriers, excipients, and stabilizers can be found in *Remington: The Science and Practice of Pharmacy* (2005) 21st Edition, Philadelphia, Pa. Lippincott Williams & Wilkins. For example, suitable carriers include excipients and stabilizers which are nontoxic to recipients at the dosages and concentrations employed, and include buffers such as, for example, acetate, Tris, phosphate, citrate, and other organic acids; antioxidants including ascorbic acid and methionine; preservatives such as, for example, octadecyldimethylbenzyl ammonium chloride; hexamethonium chloride; benzalkonium chloride, benzethonium chloride; phenol, butyl or benzyl alcohol; alkyl parabens such as, for example, methyl or propyl paraben; catechol; resorcinol; cyclohexanol; 3-pentanol; and m-cresol; amino acids such as, for example, glycine, glutamine, asparagine, histidine, arginine, or lysine; monosaccharides, disaccharides, and other carbohydrates including glucose, mannose, or dextrins; chelating agents such as, for example, EDTA; tonicifiers such as, for example, trehalose and sodium chloride; sugars such as, for example, sucrose, mannitol, trehalose or sorbitol; surfactant such as, for example, polysorbate; salt-forming counter-ions such as, for example, sodium; and/or non-ionic surfactants such as, for example, Tween or polyethylene glycol (PEG). The pharmaceutical compositions may comprise other therapeutic agents. The present compositions can be provided as single doses or in multiple doses covering the entire or partial treatment regimen. The compositions can be provided in liquid, solid, semi-solid, gel, aerosolized, vaporized, or any other form from which it can be delivered to a subject.

In one aspect, this disclosure provides kits for treating a subject in need of treatment (e.g., for a subject having symptoms of ZIKV or for inhibiting ZIKV infection). Such a kit includes compounds and/or compositions of the present disclosure and instructions for using same.

In an aspect, the present disclosure provides methods of treating a subject having ZIKV and/or inhibiting a subject from developing ZIKV infection. For example, a method of treating comprises administering one or more compound of the present disclosure or a composition comprising one or more compounds of the present disclosure to a subject in need of treatment for a Zika infection (e.g., a subject exhibiting symptoms of a Zika viral infection or a subject in need of a prophylactic treatment for a Zika viral infection). In various examples, a method comprises administering to a subject who has a Zika infection a therapeutically effective amount of a compound or composition of the present disclosure. A method can comprise using a combination of different compounds and/or compositions of the present disclosure.

"Therapeutically effective amount" as used herein means the amount of the compound or composition comprising one or more of the compounds administered to an subject (e.g., in a single dose, in multiple doses, in all of the doses, in a single administration, in multiple administrations, or in all of the administrations) stops or prevents Zika infection. For example, a therapeutically effective amount of a compound or composition is an amount that prevents or provides a clinically significant change in a disease (e.g., reduce by at least about 30 percent, at least about 50 percent, or at least about 90 percent) of one or more features of a disease or condition described herein.

As used herein, the term "subject" refers to animals such as mammals. Suitable examples of mammals include, but are not limited to, primates (e.g., humans), cows, sheep, goats, horses, dogs, cats, rabbits, rats, mice, and the like. In certain embodiments, the subject is a human.

The method can be carried out in a subject who has been diagnosed with or is suspected of being infected with ZIKV (i.e., therapeutic use). A method can also be carried out in subjects who have a relapse or a high risk of relapse after being treated for ZIKV infection. A method can be carried out in a subject in need of prophylaxis for ZIKV infections/illnesses.

Any of the compounds and/or compositions comprising the compounds described herein can be administered to a subject using any known method and route, including oral, parenteral, subcutaneous, intraperitoneal, intrapulmonary, intranasal and intracranial injections. Parenteral infusions include intramuscular, intravenous, intraarterial, intraperitoneal, and subcutaneous administration. Topical and/or transdermal administrations are also encompassed.

In an example, method comprises a composition of the present disclosure comprising one or more pharmaceutically acceptable carrier, excipient, stabilizer, or combination thereof and one or more compound having the following structure:

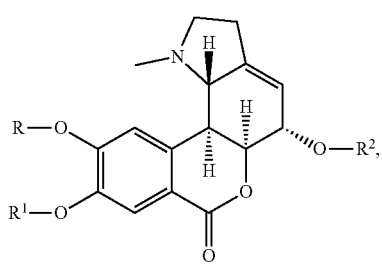

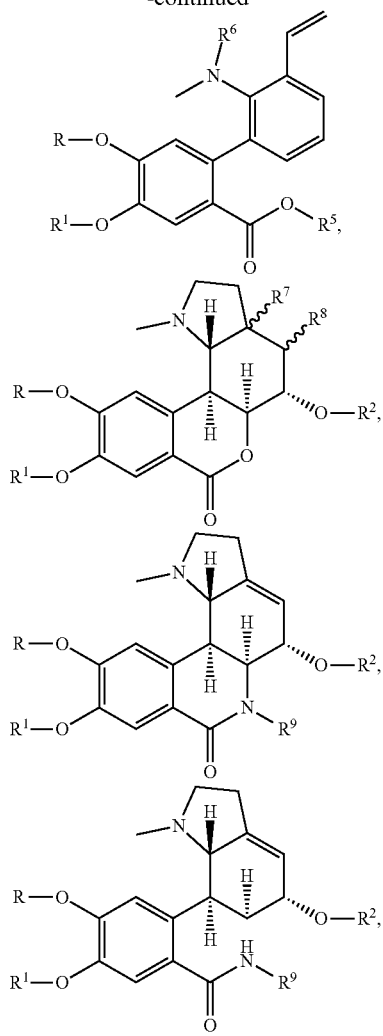

or combinations thereof;
where R and $R^1$ are independently selected from H; $C_1$ to $C_8$ (e.g., $C_1$, $C_2$, $C_3$, $C_4$, $C_5$, $C_6$, $C_7$, and $C_8$) acyl aliphatic groups; $C_1$ to $C_8$ (e.g., $C_1$, $C_2$, $C_3$, $C_4$, $C_5$, $C_6$, $C_7$, and $C_8$) carbamide aliphatic groups; $C_1$ to $C_8$ (e.g., $C_1$, $C_2$, $C_3$, $C_4$, $C_5$, $C_6$, $C_7$, and $C_8$) amide aliphatic groups; $C_1$ to $C_8$ (e.g., $C_1$, $C_2$, $C_3$, $C_4$, $C_5$, $C_6$, $C_7$, and $C_8$) aliphatic groups; $C_1$ to $C_8$ (e.g., $C_1$, $C_2$, $C_3$, $C_4$, $C_5$, $C_6$, $C_7$, and $C_8$) acyl aliphatic aryl groups, where $C_1$ to $C_8$ is the length of the aliphatic portion of the acyl aliphatic aryl group, $C_1$ to $C_8$ (e.g., $C_1$, $C_2$, $C_3$, $C_4$, $C_5$, $C_6$, $C_7$, and $C_8$) carbamide aliphatic aryl groups, wherein $C_1$ to $C_8$ is the length of the aliphatic portion of the carbamide aliphatic aryl group; or $C_1$ to $C_8$ (e.g., $C_1$, $C_2$, $C_3$, $C_4$, $C_5$, $C_6$, $C_7$, and $C_8$) amide aliphatic aryl groups, where $C_1$ to $C_8$ is the length of the aliphatic portion of the amide aliphatic aryl group; or R and $R^1$ taken together form

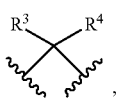

where $R^3$ and $R^4$ are independently selected from H and $C_1$ to $C_8$ (e.g., $C_1$, $C_2$, $C_3$, $C_4$, $C_5$, $C_6$, $C_7$, and $C_8$) aliphatic groups; where R² is selected from H; C₁ to C₈ (e.g., C₁, C₂, C₃, C₄, C₅, C₆, C₇, and C₈) acyl aliphatic groups; C₁ to C₈ (e.g., C₁, C₂, C₃, C₄, C₅, C₆, C₇, and C₈) carbamide aliphatic groups; C₁ to C₈ (e.g., C₁, C₂, C₃, C₄, C₅, C₆, C₇, and C₈) amide aliphatic groups; C₁ to C₈ (e.g., C₁, C₂, C₃, C₄, C₅, C₆, C₇, and C₈) acyl aromatic groups; C₁ to C₈ (e.g., C₁, C₂, C₃, C₄, C₅, C₆, C₇, and C₈) carbamide aryl groups; or C₁ to C₈ (e.g., C₁, C₂, C₃, C₄, C₅, C₆, C₇, and C₈) amide aryl groups, or R² has the following structure:

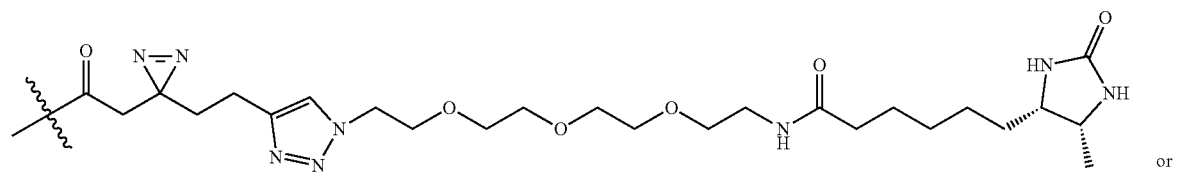

or

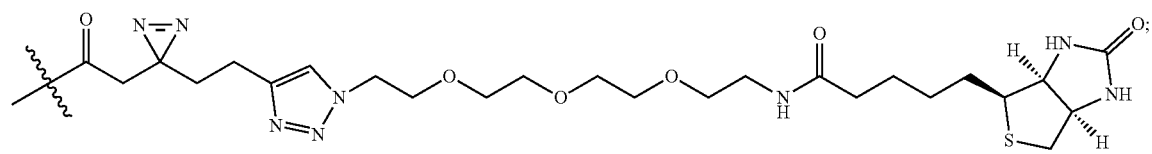

where R⁵ is selected from H and C₁ to C₈ aliphatic groups, or R⁵ has the following structure:

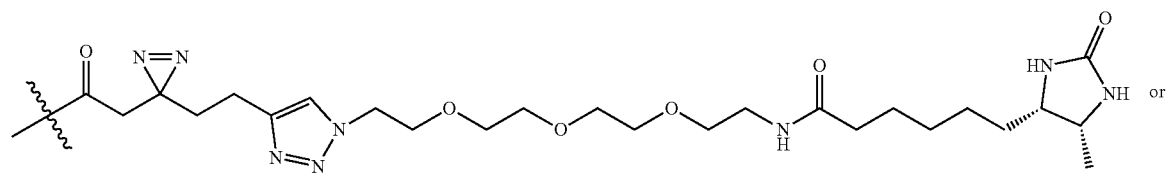

or

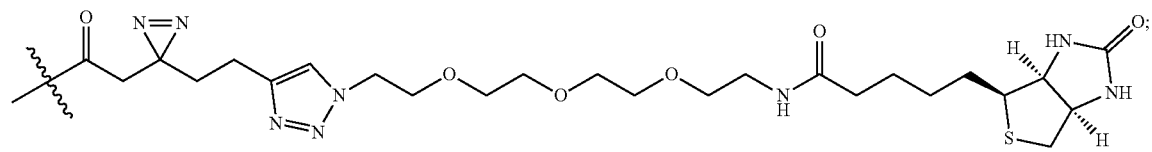

where R⁶ is selected from H and C₁ to C₈ (e.g., C₁, C₂, C₃, C₄, C₅, C₆, C₇, and C₈) aliphatic groups; where R⁷ is H, where the stereochemistry is R or S; where R⁸ is H, where the stereochemistry is R or S; and where R⁹ is a C₁ to C₈ (e.g., C₁, C₂, C₃, C₄, C₅, C₆, C₇, and C₈) aliphatic group. For example, a compound of the present disclosure has the following structure:

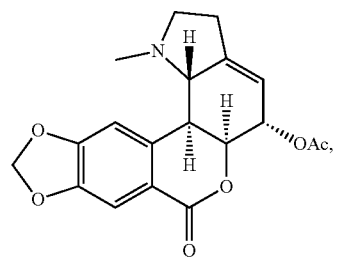 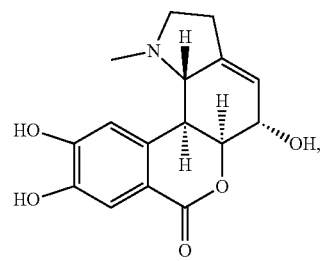 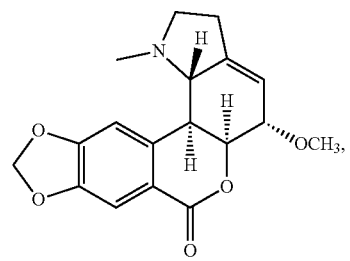

33
34
-continued
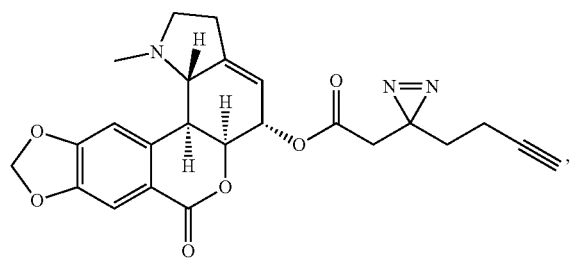
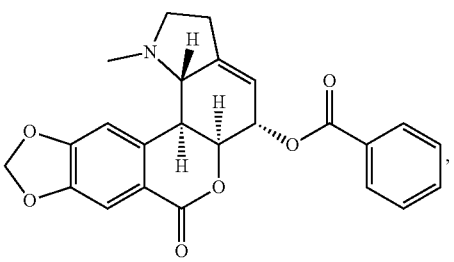
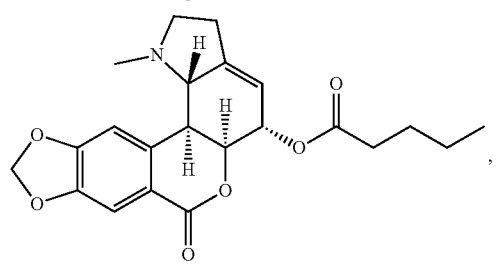
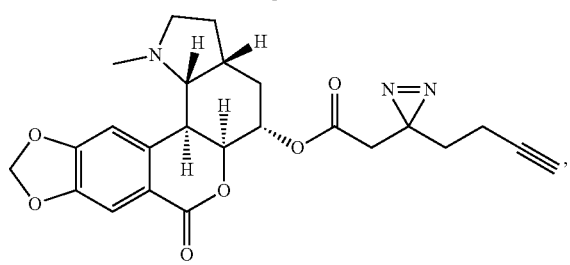
AL-32
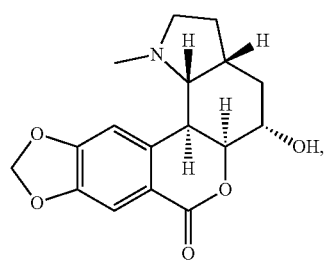
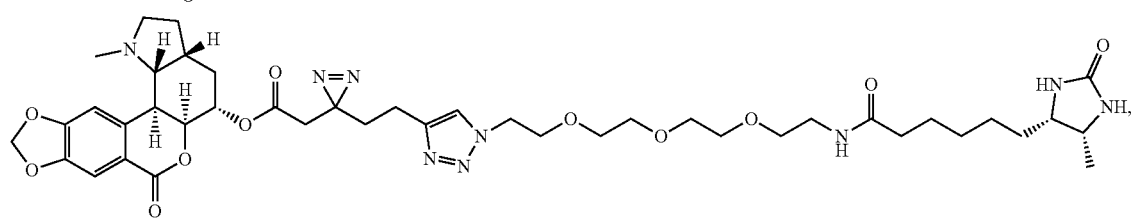
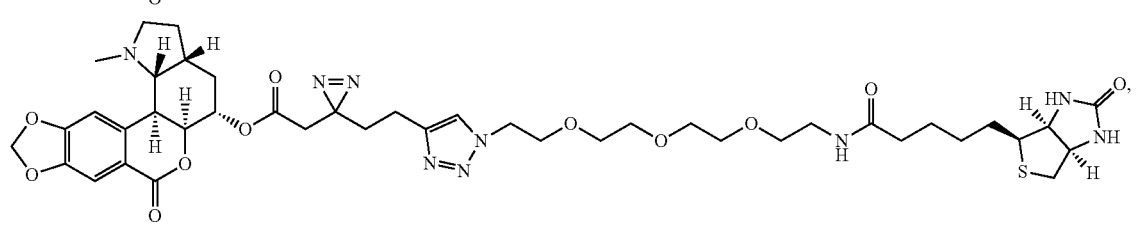
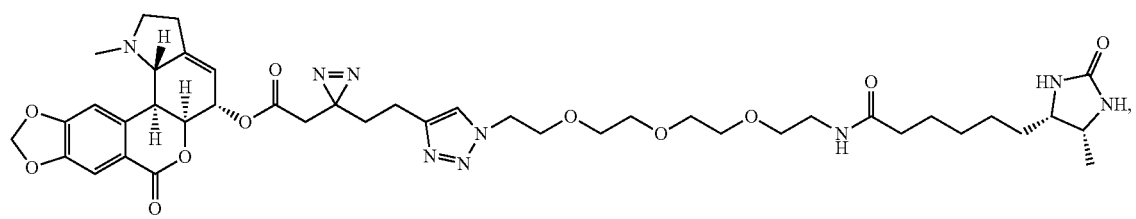
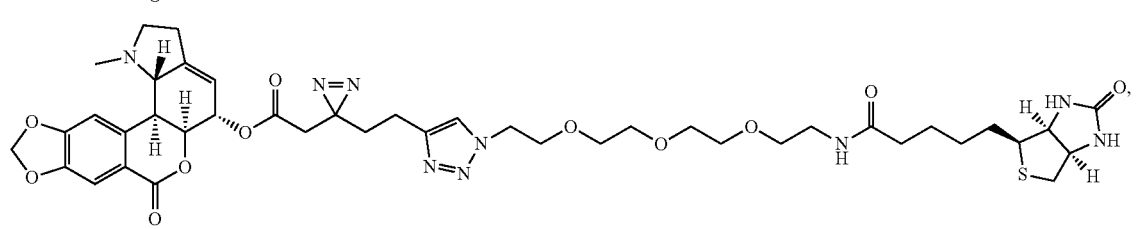

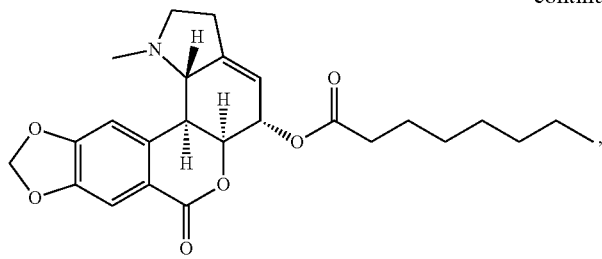 or 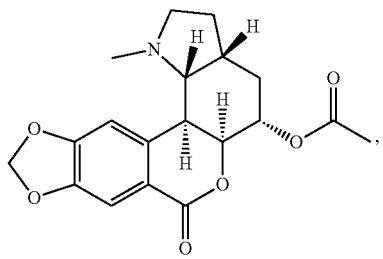

The following examples are presented to illustrate certain aspects of the present disclosure. They are not intended to be limiting in any way.

Example 1

This example describes use of compounds of the present disclosure.

Results

Figure 5:
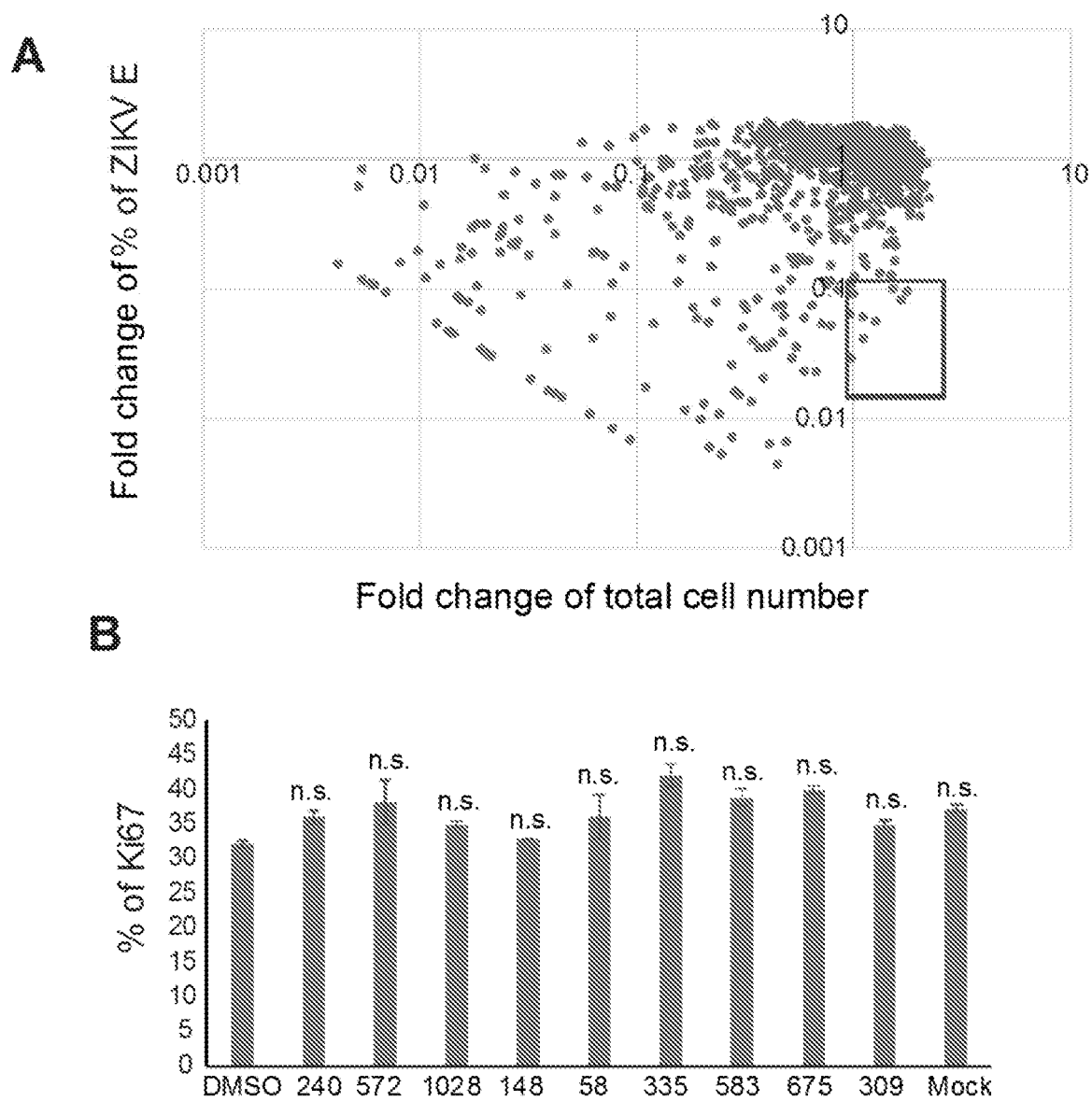
FIG. 5 shows a high content chemical screen identifies anti-ZIKV drug candidates that promote proliferation in hNPCs. (A) Two dimensional analysis of anti-ZIKV drug screen. X-axis represents the fold change of total cell number, which was calculated by dividing the total cell number of the chemical treated well by the average total cell number of DMSO treated wells. Y-axis represents the fold change of the percentage of ZIKV infected cells, which was calculated by dividing the percentage of ZIKV E expressing cells of the chemical-treated well by the average percentage of ZIKV E expressing cells in DMSO-treated wells. The compounds, in which the fold change of total cell number >1 and the fold change of the percentage of ZIKV infection <20% were picked for subsequent evaluation. (B-D) The quantification of proliferation rate (B), infection rate (C) and total cell number (D) of hNPCs at 72 h after ZIKV infection with primary hit compounds or DMSO treatment (n=3). p values were calculated by one-way repeated measures ANOVA with a Bonferroni test for multiple comparisons. *p<0.05, p<0.01 and *p<0.001. (E) Vero re-infection assay using different ZIKV (MR 766 strain) titers to determine the sensitivity. (F) Gene ontology pathway analysis of genes that are 2>fold changed in Mock vs. HH, Mock vs. ZIKV+HH, Mock vs. AQ, and Mock vs. ZIKV+HH in FIG. 1L. (G) Two dimensional analysis of compound screen and the chemical structure of the hit compound Merbromin. The analysis sought compounds that increase cell proliferation rates in ZIKV-infected hNPCs. The X-axis represents the fold change of total cell number, which was calculated by dividing the total cell number of the chemical treated wells by the average of total cell number of DMSO treated wells. The Y-axis represents the fold change of cell proliferation rate, which was calculated by dividing the percentage of $Ki67^+$ cells of the chemical treated well by the average of the percentage of $Ki67^+$ cells of DMSO treated wells. One hit compound, for which the fold change of total cell number >1 and the fold change of the percentage of $Ki67^+$ cells >2.5 was picked for follow-up evaluation. (H-K) Immunocytochemical analysis (H), the quantification of the infection rate (I), the quantification of the proliferation rate (J) and the quantification of the total cell number (K) of hNPCs at 72 h after ZIKV infection with 20 μM Merbromin or DMSO treatment (n=3). Cells were fixed and stained for Ki67, ZIKV E and DAPI. Scale bars, 100 μm. p values were calculated by unpaired two-tailed Student's t-test. *p<0.05, and ***p<0.001.
Figure 5:
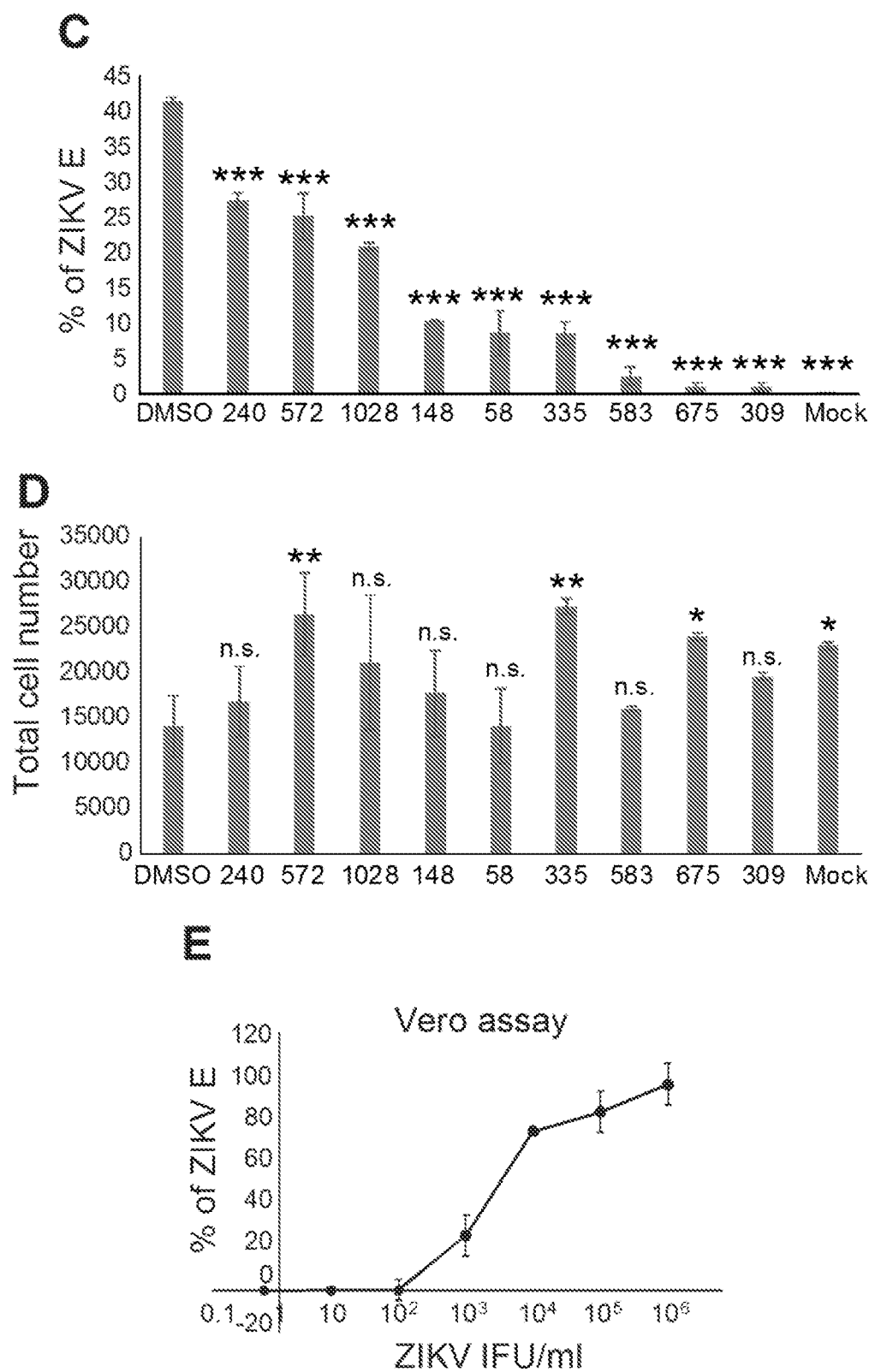
Figure 5:
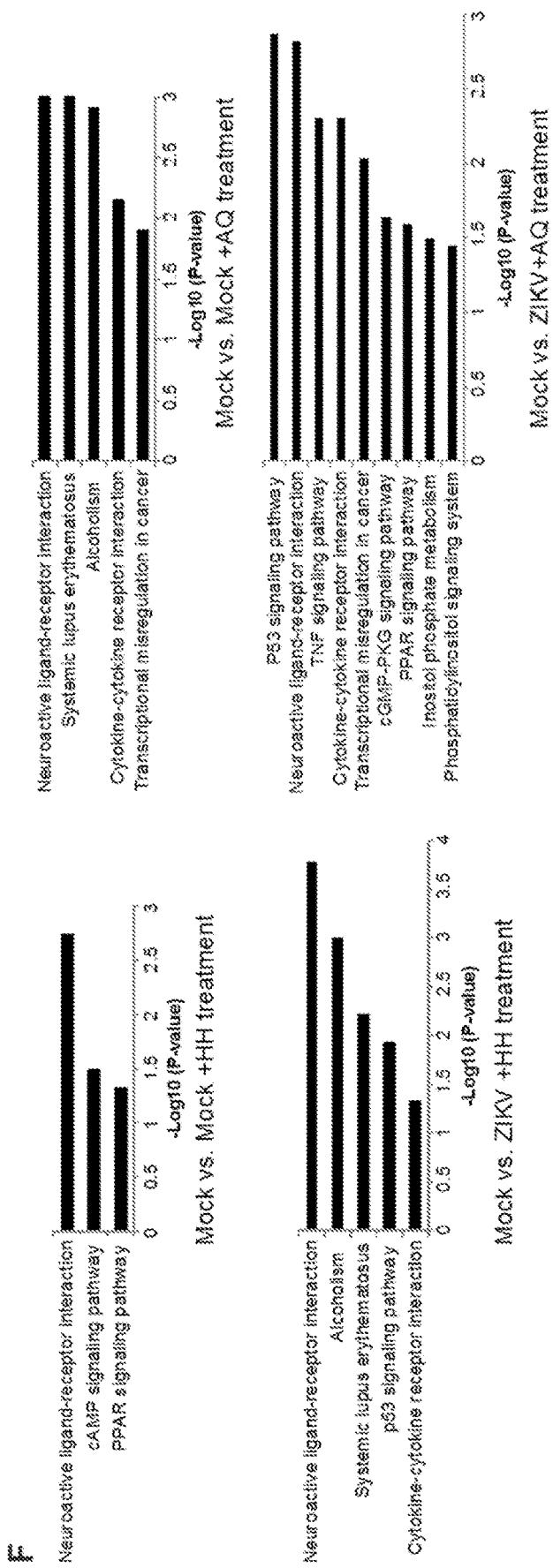
Figure 5:
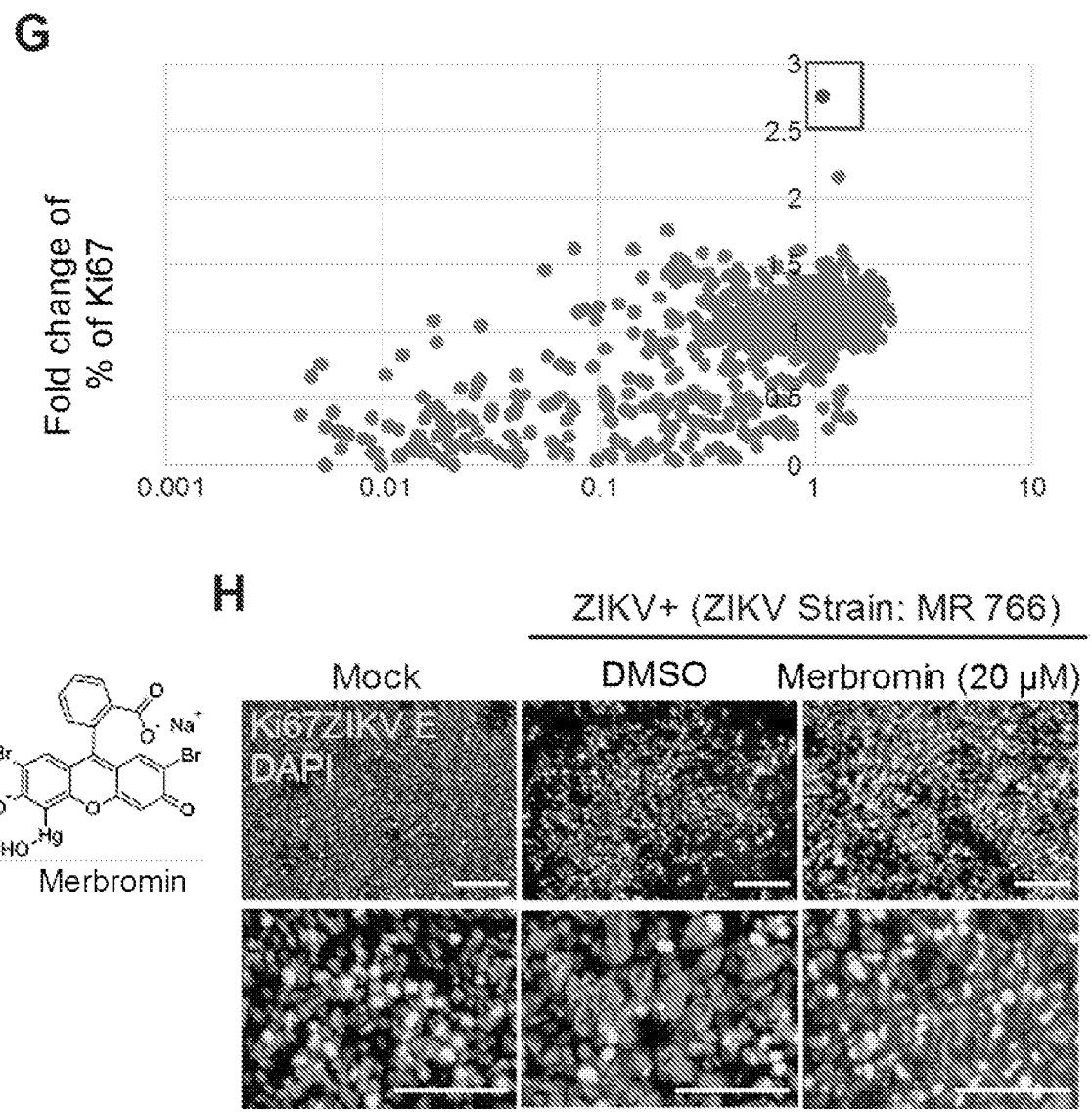
Figure 5:
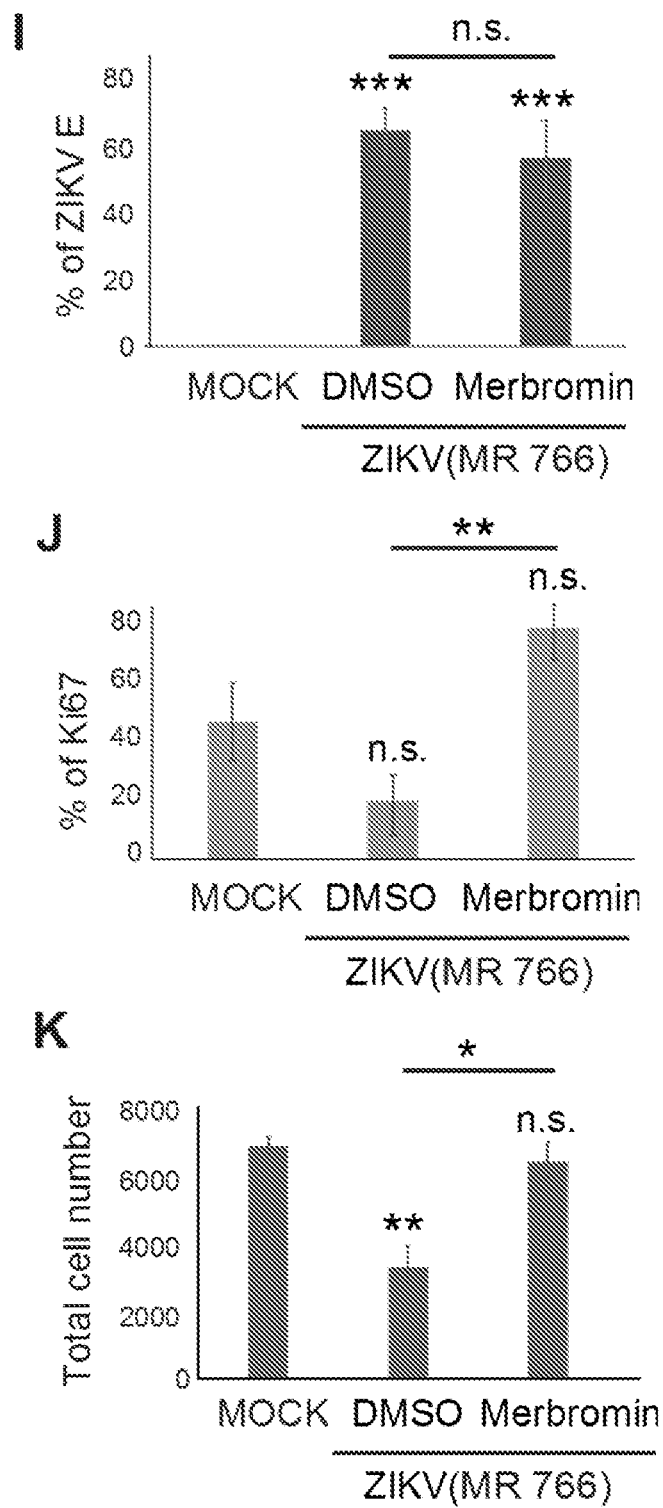

A high content chemical screen identifies compounds that inhibit ZIKV infection of hNPCs. To identify drugs that inhibit ZIKV infection, we screened the Prestwick library that includes 1120 FDA-approved drug and drug candidates, selected for known bioavailability and safety in humans. To perform the screen, hNPCs seeded in 384-well plates were treated with each compound from the library or vehicle control (DMSO) for 1 hour, followed by addition of ZIKV MR766 at a MOI=0.125. After two hour of inoculation with ZIKV, the virus-containing medium was replaced by fresh virus-free medium and compounds were replenished for each well (See Methods). After an additional three days of culture, cells were fixed and stained with antibodies against the ZIKV envelop protein (ZIKV E) and a cell proliferation marker Ki67 (FIG. 1A). The percentages of ZIKV E$^+$ cells, Ki67$^+$ cells and total cell number were quantified by an automated imaging and analysis system. A two dimensional analysis was performed to choose the primary hit compounds (FIG. 5A). The X-axis represents the fold change of total cell number, which was calculated by dividing the total cell number of the chemical-treated well by the average total cell number of DMSO-treated wells. The Y-axis represents the fold change of the percentage of ZIKV infected cells, which was calculated by dividing the percentage of cells expressing ZIKV E in each chemical-treated well by the average of the percentage of cells expressing ZIKV E from DMSO-treated wells. Positive hits were defined as compounds that resulted in a total cell number fold change of greater than 1 and a suppression of ZIKA infection to less than 20% of control. Based on the fold change of the percentage of ZIKV infection, the signal-to-basal (S/B) ratio is 4.2 and the coefficient of variation (CV) is 6.9%. The Z factor is 0.59 indicating a robust screening system. To avoid the possibility that a lower infection rate was due to hNPC growth arrest, only compounds that did not significantly alter the percentage of Ki67$^+$ cells were picked as primary hits.

TABLE 1

Information of confirmed hit compounds.

| Chemical name | CAS-number | Therapeutic group | Number in library |
|---|---|---|---|
| Proglumide | 6620-60-6 | Anti-ulcerative | 240 |
| Mometasone furoate | 83919-23-7 | Anti-inflammatory | 572 |
| Benzathinebenzyl-penicillin | 5928-84-7 | Anti-bacterial | 1028 |
| Canrenoic acid potassium salt | 2181-04-6 | Anti-hyper-cholesterolemic | 148 |
| Oxethazaine | 126-27-2 | Local anesthesic | 58 |
| Zaprinast | 37762-06-4 | Erectogen | 335 |
| Papaverine hydrochloride | 61-25-6 | Vasodilator | 583 |
| Hippeastrine hydrobromide | 22352-41-6 | Hypotensor | 675 |
| Amodiaquin dihydrochloride dihydrate | 6398-98-7 | Antimalarial | 309 |

Using these criteria, 9 primary hit compounds were confirmed to significantly inhibit ZIKV infection without affecting cell proliferation at 10 μM (FIG. 5B-D). Detailed information of the 9 hit compounds is summarized in Table 1. Two hit compounds that showed the highest efficacy (FIG. 5C), Hippeastrine hydrobromide (HH), and Amodiaquine dihydrochloride dihydrate (AQ), were chosen for further study (FIG. 1B). The IC$_{50}$ values of anti-ZIKV activity are 5.5 μM and 6.0 μM for HH and AQ, respectively (FIG. 1C). Both compounds effectively inhibited ZIKV infection and blocked ZIKV induced growth arrest or apoptosis compared to DMSO controls (FIG. 1D-H). HH and AQ also significantly suppressed the production of ZIKV viral RNA (vRNA) as indicated by qRT-PCR (FIG. 1I), and production of infectious ZIKV as indicated by a Vero cell re-infection assay (FIG. 1J-K and FIG. 5E). Furthermore, RNA-seq analysis suggested that HH or AQ treatment reversed the transcriptional changes induced by ZIKV (MR766 strain) infection (FIG. 1L). Interestingly, gene ontology analysis highlighted neuroactive ligand-receptor interaction pathway in both Mock vs. HH and Mock vs. AQ conditions (FIG. 5F). To confirm that the anti-ZIKV activity of HH and AQ is not restricted to MR766, another ZIKV strain, PRVABC59, collected in Puerto Rico from a human serum specimen in December of 2015 (NCBI Accession No. KU501215), was inoculated onto hNPCs at a MOI=0.125. Immunocytochemical analysis showed 25 μM HH or 15 μM AQ effectively inhibited ZIKV infection (FIGS. 1M and 1N).

Interestingly, we also identified a hit compound, Merbromin, that significantly increased hNPC proliferation and rescued the total cell loss in ZIKV infected hNPCs, although it did not affect ZIKV infection (FIG. 5G-1K). To identify drug candidates inhibiting and eliminating ZIKV infection, we focused on HH and AQ for further validation.

Figure 2:
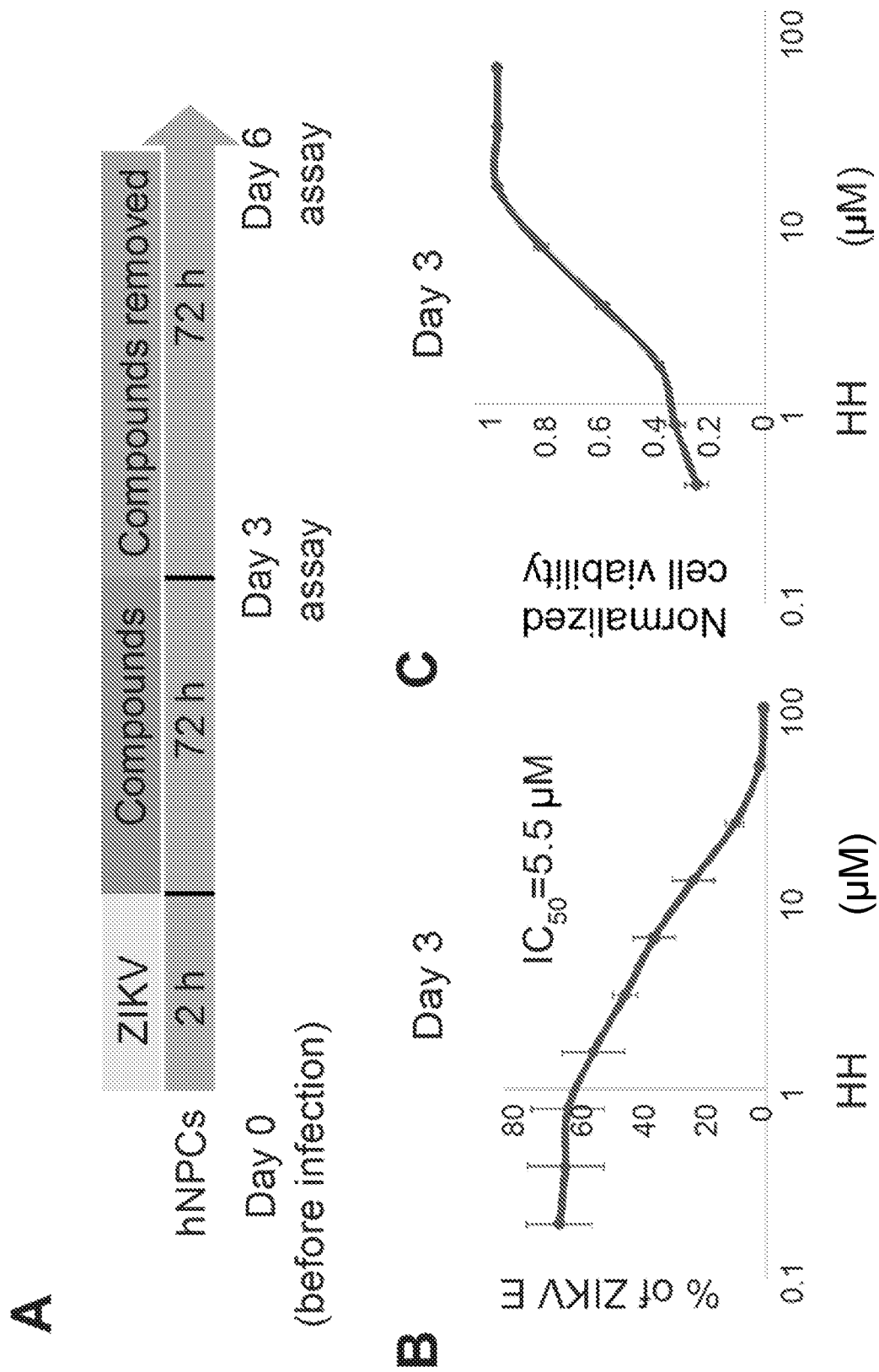
FIG. 2 shows HH eliminates virus in ZIKV-infected hNPCs. (A) Scheme to evaluate the elimination of ZIKV. At day 0, hNPCs were infected with ZIKV for 2 h. After removal of ZIKV infection medium, hNPCs were treated with drug candidates. At day 3, the culture medium was changed to fresh medium without compounds. The cells were maintained in drug-free culture until day 6 and used for immunohistochemistry and qRT-PCR. (B and C) Inhibitory curve and $IC_{50}$ of HH calculated based on the infection rate (B) and normalized cell viability (C) (n=6). (D and E) Immunocytochemistry analysis (D) and the quantification of infection rate, cell apoptosis rate, and total cell number (E) of hNPCs on day 3 and day 6. Cells was fixed and stained with cleaved Caspase-3 (CAS3), ZIKV E and DAPI. Scale bars, 100 µm. (F) qRT-PCR analysis to monitor the total ZIKV vRNA in the supernatant of hNPC cultures on day 6. Scale bars, 200 µm. (n=3). (G) Vero cell reinfection assay to monitor the infective ZIKV vRNA in the supernatant of hNPC cultures at day 6 after ZIKV infection. Scale bars, 200 µm. (n=3). (H) Quantification of ZIKV infectious particles produced by ZIKV-infected hNPCs at day 6 by the Vero cell reinfection assay. (I) hNPCs with or without ZIKV infection treated with HH maintain hNPC marker expression and differentiation capacity. hNPCs with or without ZIKV MR766 infection were treated with 25 µM HH or DMSO for 3 days and then stained for SOX2, NESTIN and with DAPI. hNPCs with or without ZIKV infection and treated with HH or DMSO for 3 days were differentiated to cortical neurons. The cortical neurons were then fixed and stained for MAP2, TUJ1 and with DAPI. Scale bars, 100 µm. (n=3). (J) ZIKV (MR766 strain) dynamics in hNPCs. qRT-PCR analysis to quantify the total and replicating (−) strand vRNAs in the hNPCs at different time points post infection. The dash line shows qRT-PCR detection limit. p values were calculated by one-way repeated measures ANOVA with a Bonferroni test for multiple comparisons. $*p<0.05$, $p<0.01$ and $*p<0.001$. (K) qRT-PCR analysis of hNPCs, on which 25 µM HH or DMSO were added at 24 h, 36 h and 48 h post-ZIKV (MR766 strain) infection and maintained for additional 3 days. p values were calculated by unpaired two-tailed Student's t-test. $*p<0.05$, $p<0.01$ and $*p<0.001$, if not mentioned specifically.
Figure 2:
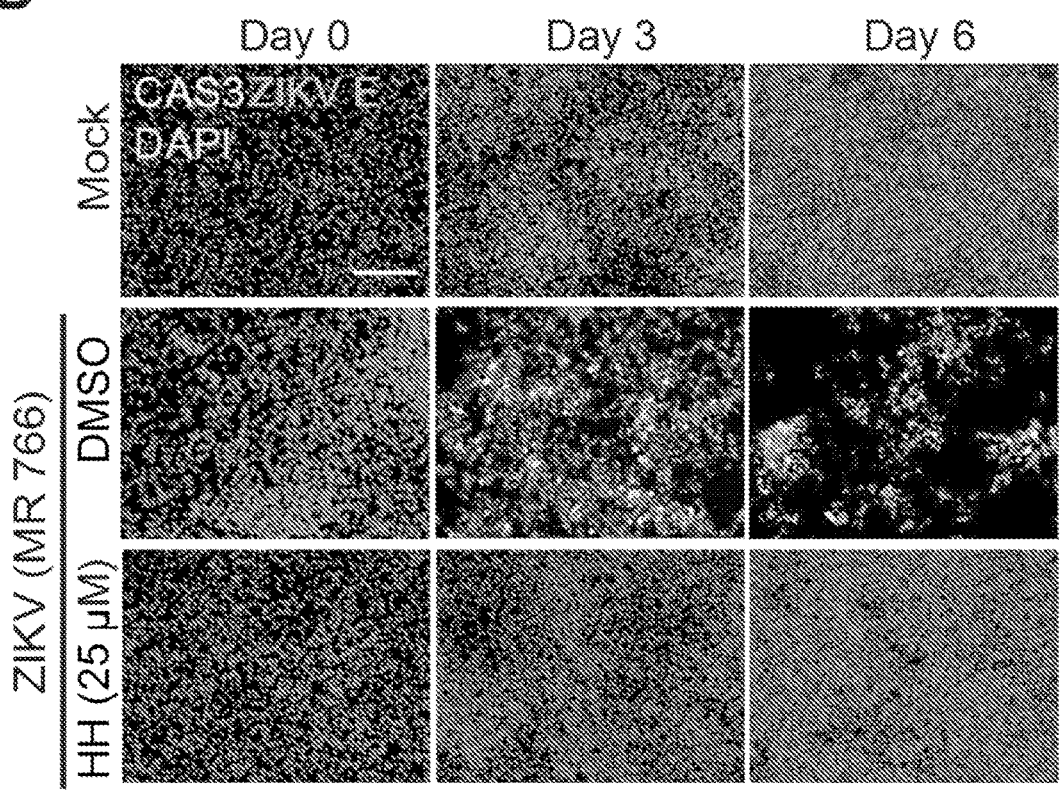
Figure 2:
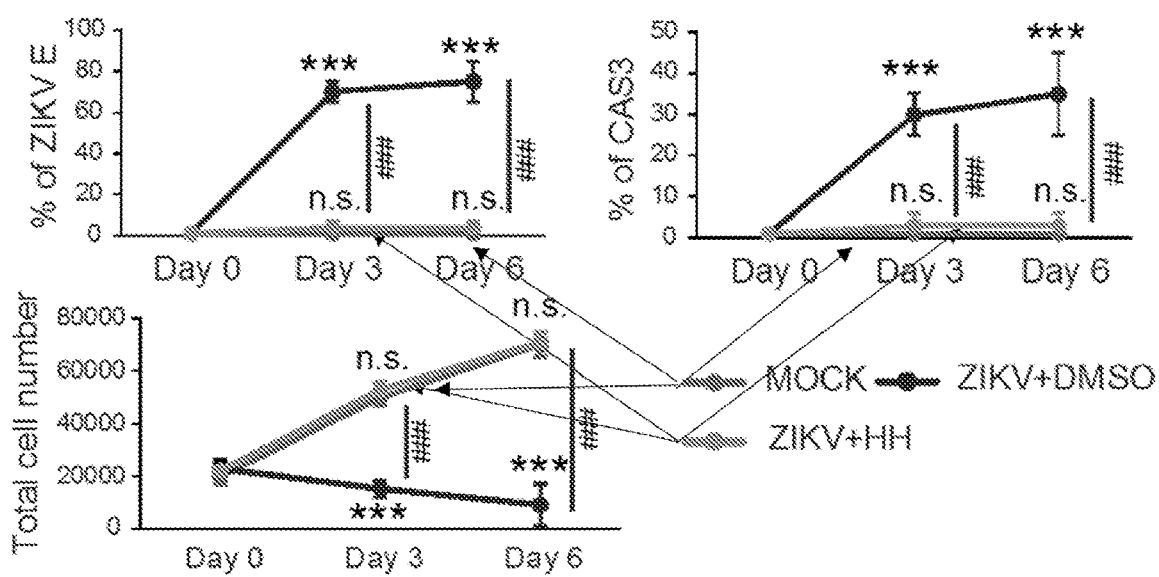
Figure 2:
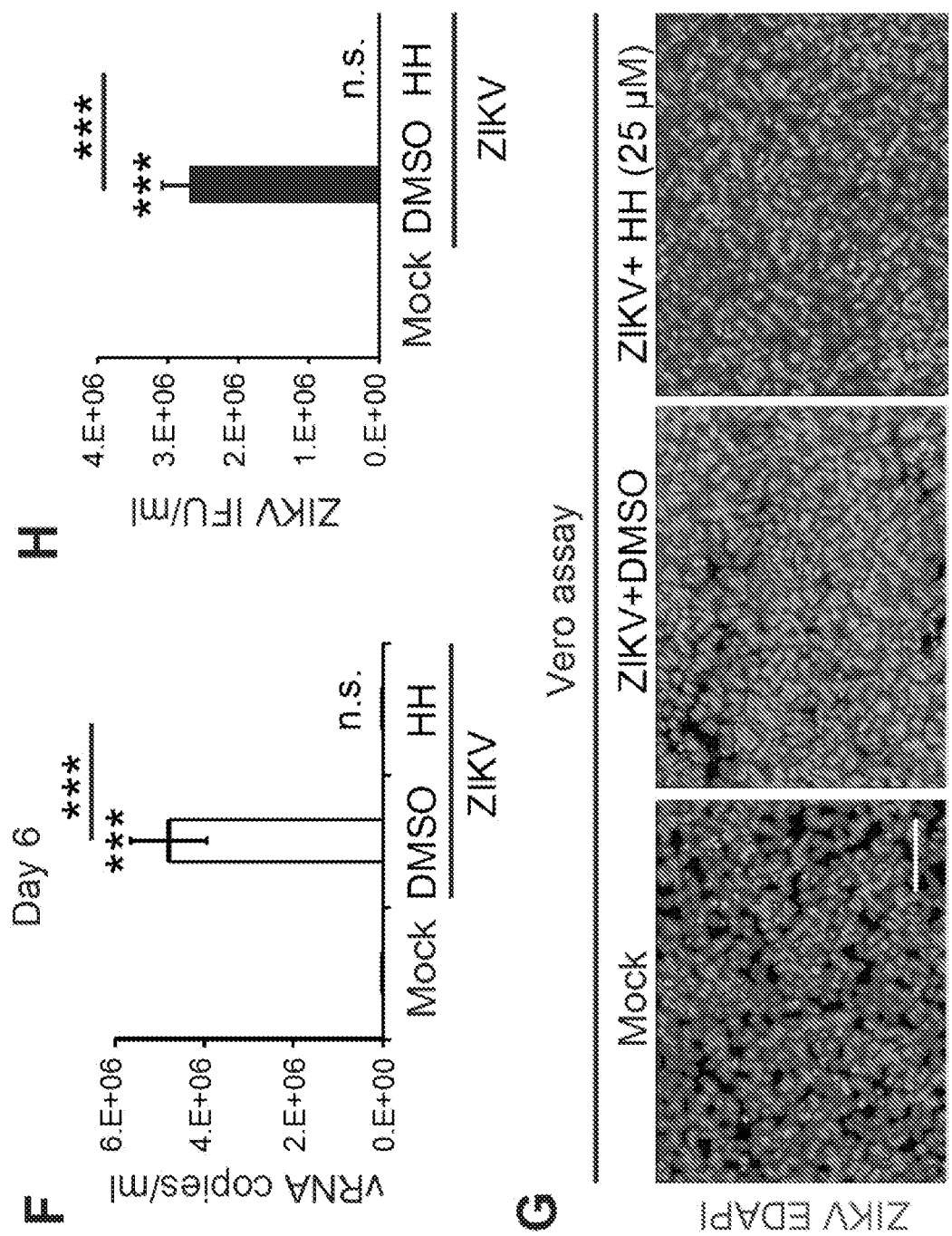
Figure 2:
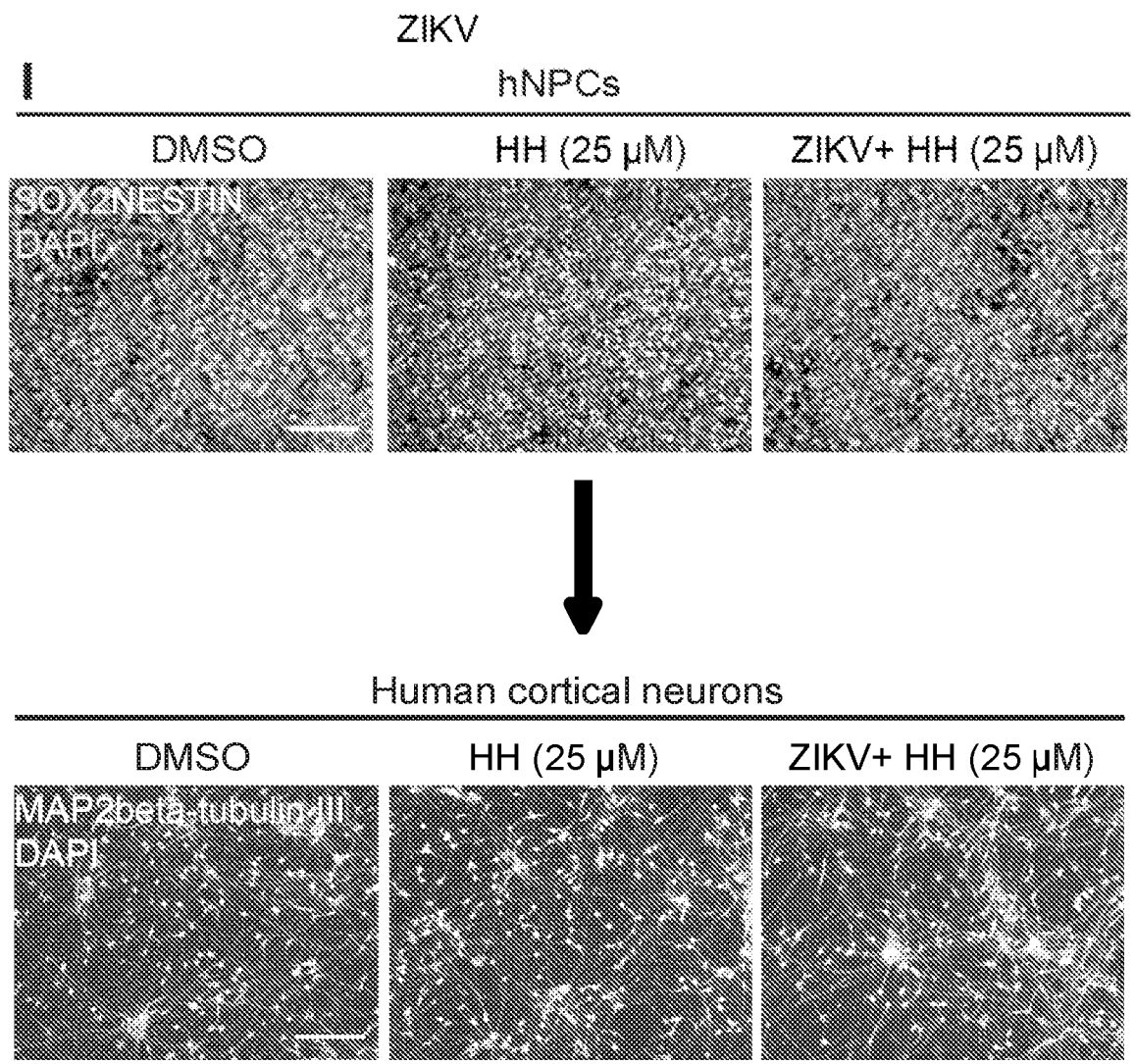
Figure 2:
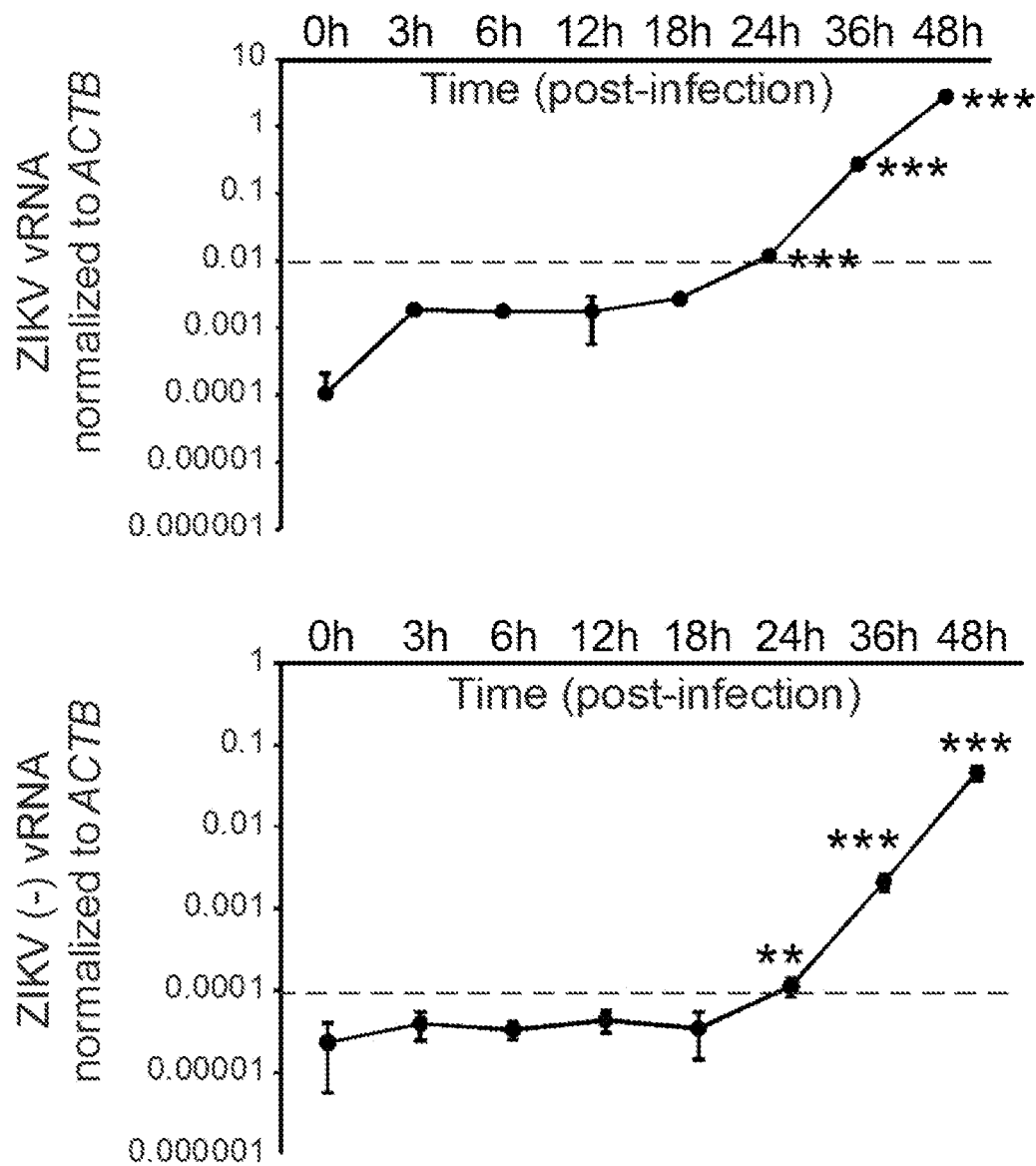
Figure 2:
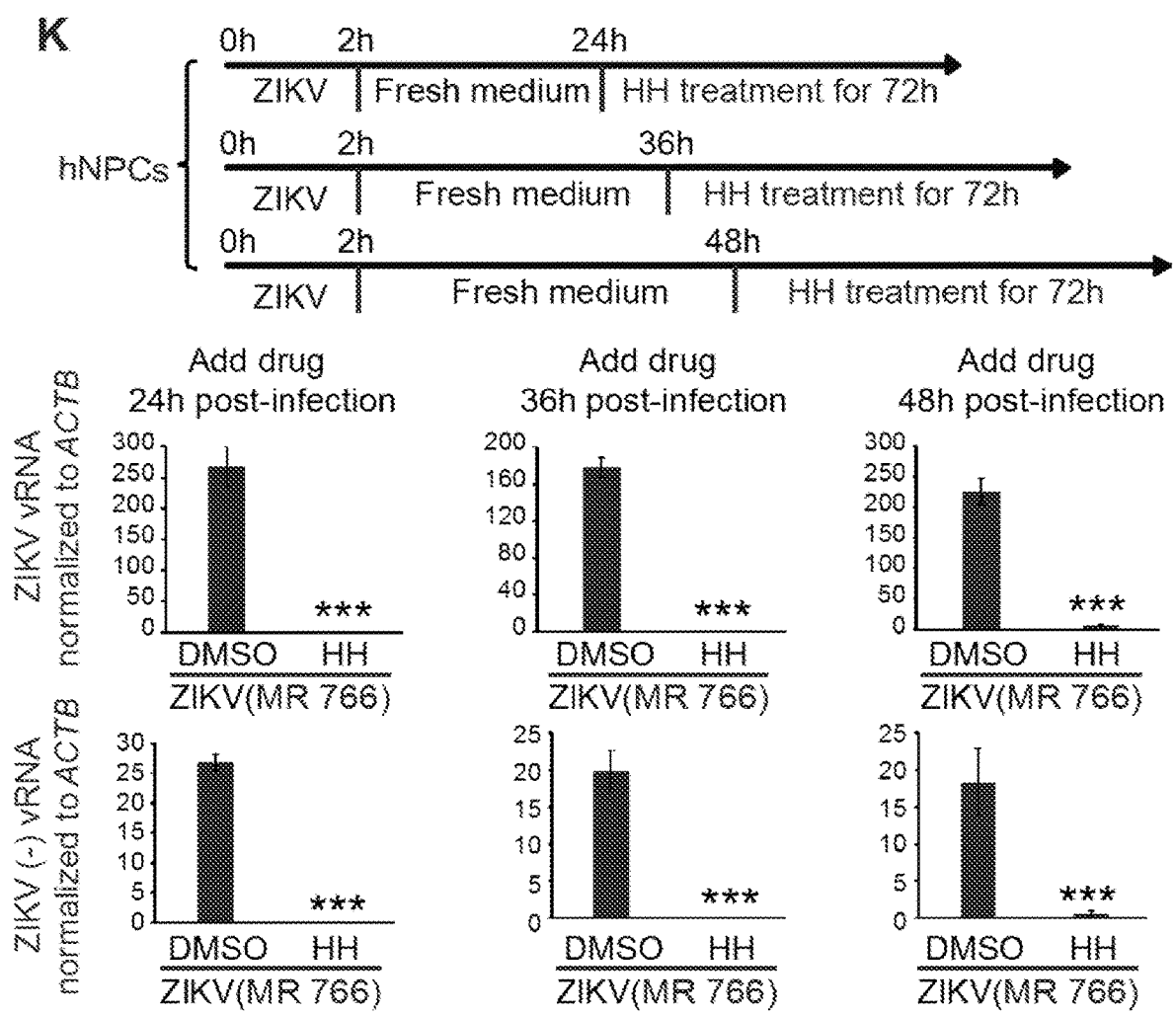
Figure 6:
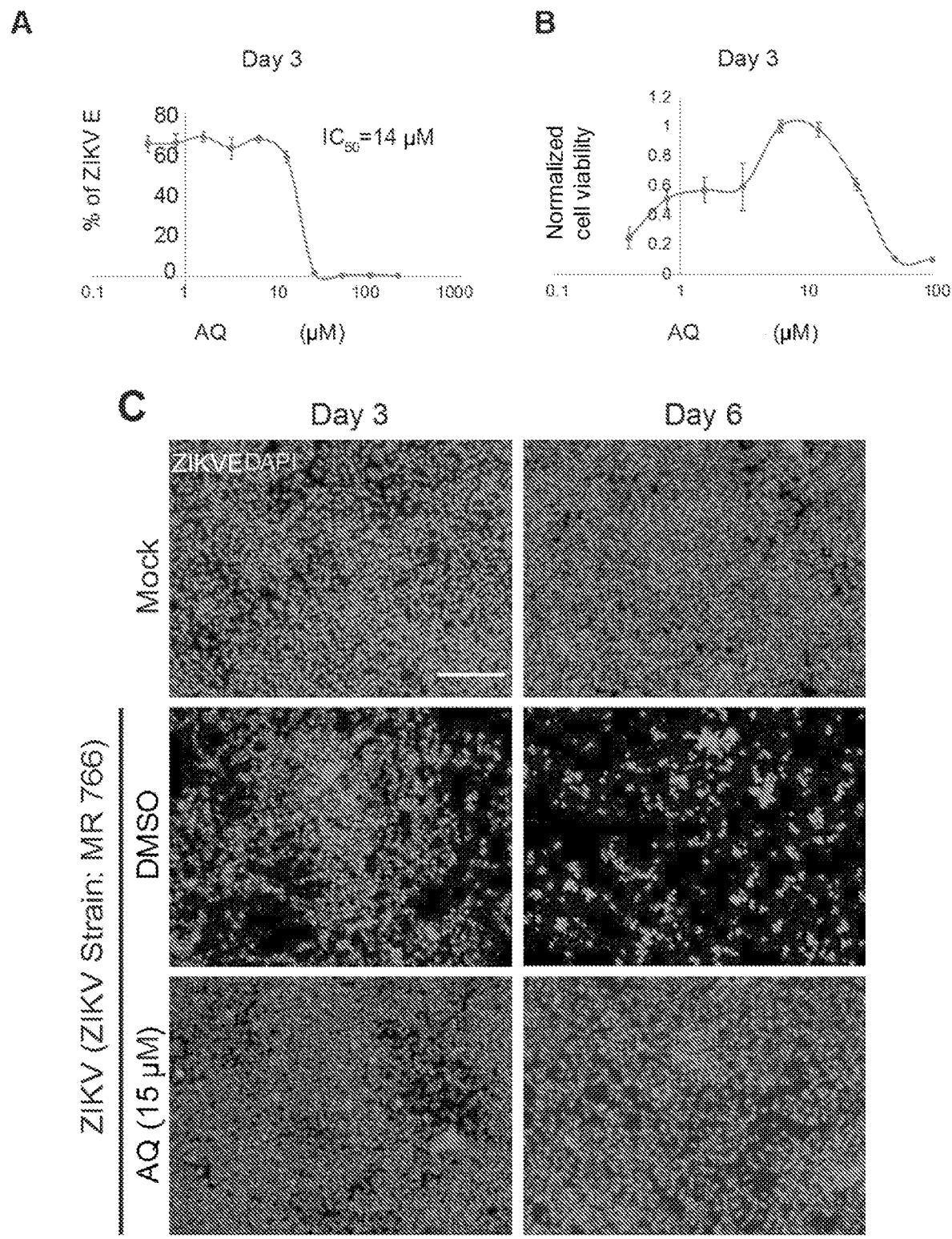
FIG. 6 shows HH, but not AQ, efficiently eliminates virus in ZIKV infected hNPCs. (A and B) Inhibitory curve and $IC_{50}$ of AQ were calculated based on the infection rate (A) and normalized cell viability (B) (n=6). (C and D) Immunocytochemistry analysis (C) and quantification of infection rate and total cell number (D) of hNPCs after ZIKV infection treated with 15 μM AQ or DMSO or mock infection (n=3). Cells were fixed and stained for ZIKV E and with DAPI. Scale bars, 100 μm. p values were calculated by unpaired two-tailed Student's t-test. *p<0.05, and ***p<0.001. (E) qRT-PCR analysis of total and replicating (−) strand of ZIKV (MR 766 strain) vRNA level in hNPCs from two additional donors. hNPCs from different donors were treated with 25 μM HH at 24 h post-infection. (F) The expression dynamics of ZIKV vRNA (FSS13025 strain) in hNPCs. qRT-PCR analysis to quantify the total and replicating (−) strand ZIKV vRNA levels in hNPCs at different time points post-infection. The dash line shows qRT-PCR detection limit. p values were calculated by one-way repeated measures ANOVA with a Bonferroni test for multiple comparisons. *p<0.05, p<0.01 and *p<0.001. (G) qRT-PCR analysis of hNPCs that were treated with 25 μM HH or DMSO at 48 h post-ZIKV (FSS13025 strain) infection and maintained for additional 3 days. p values were calculated by unpaired two-tailed Student's t-test. *p<0.05, p<0.01 and *p<0.001, unless otherwise stated.
Figure 6:
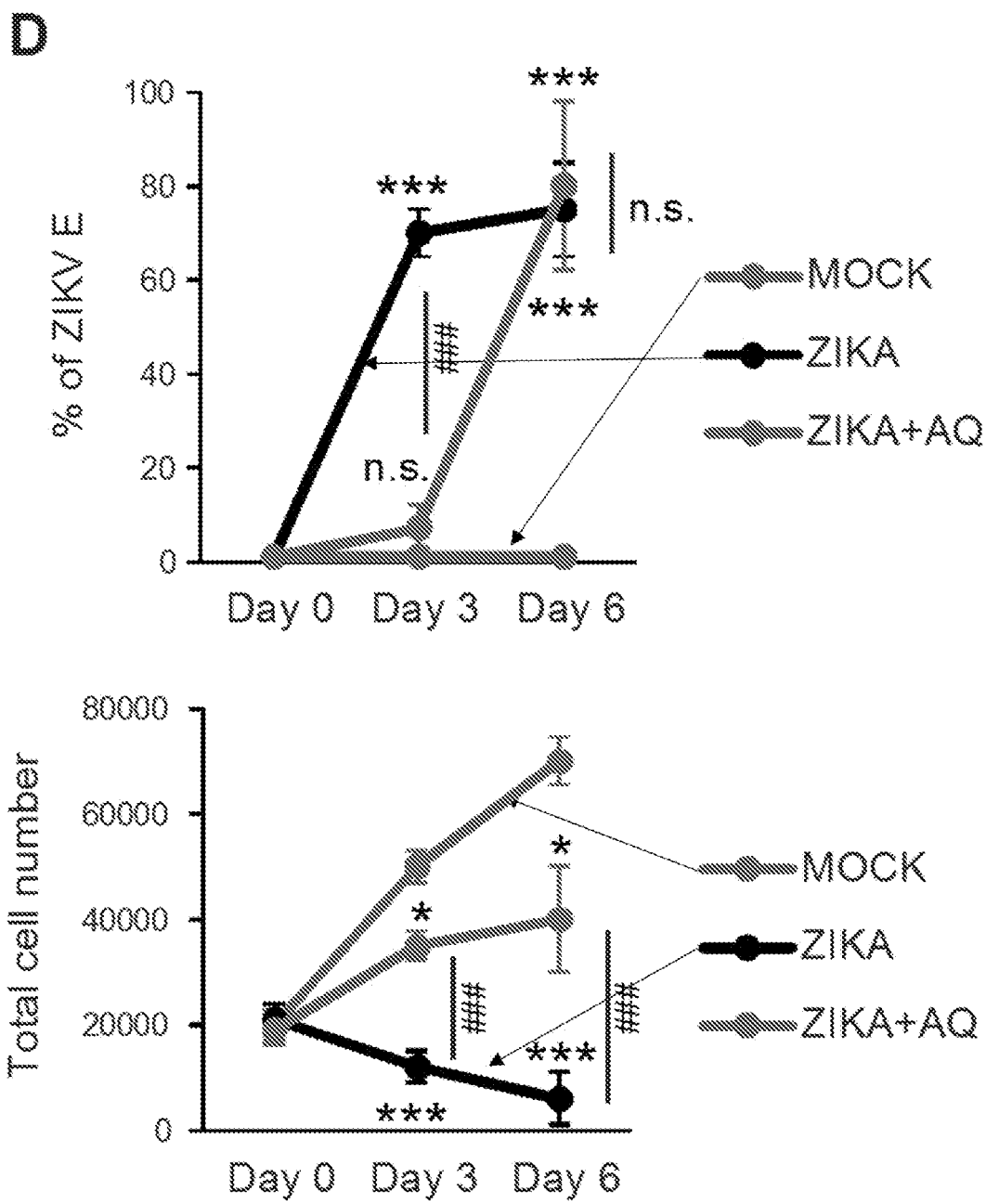
Figure 6:
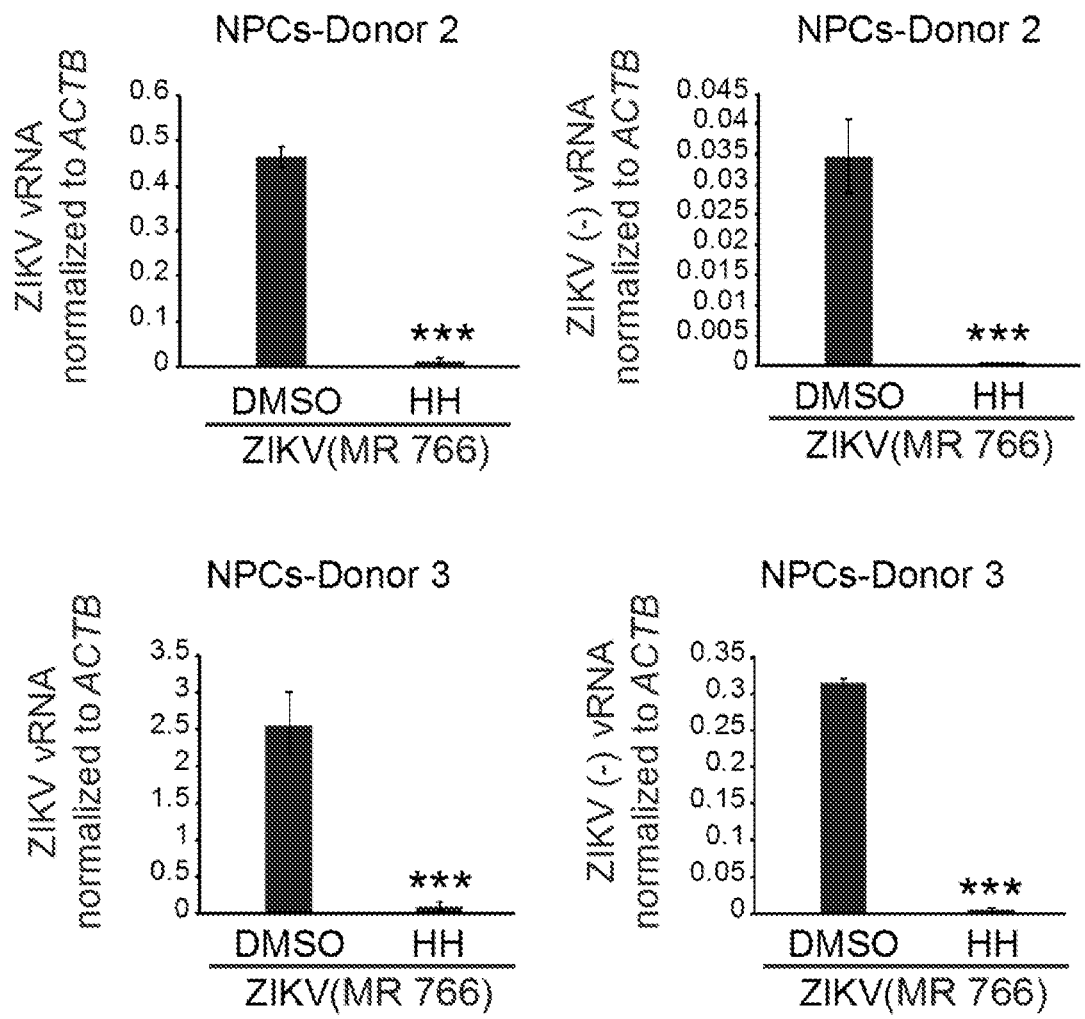
Figure 6:
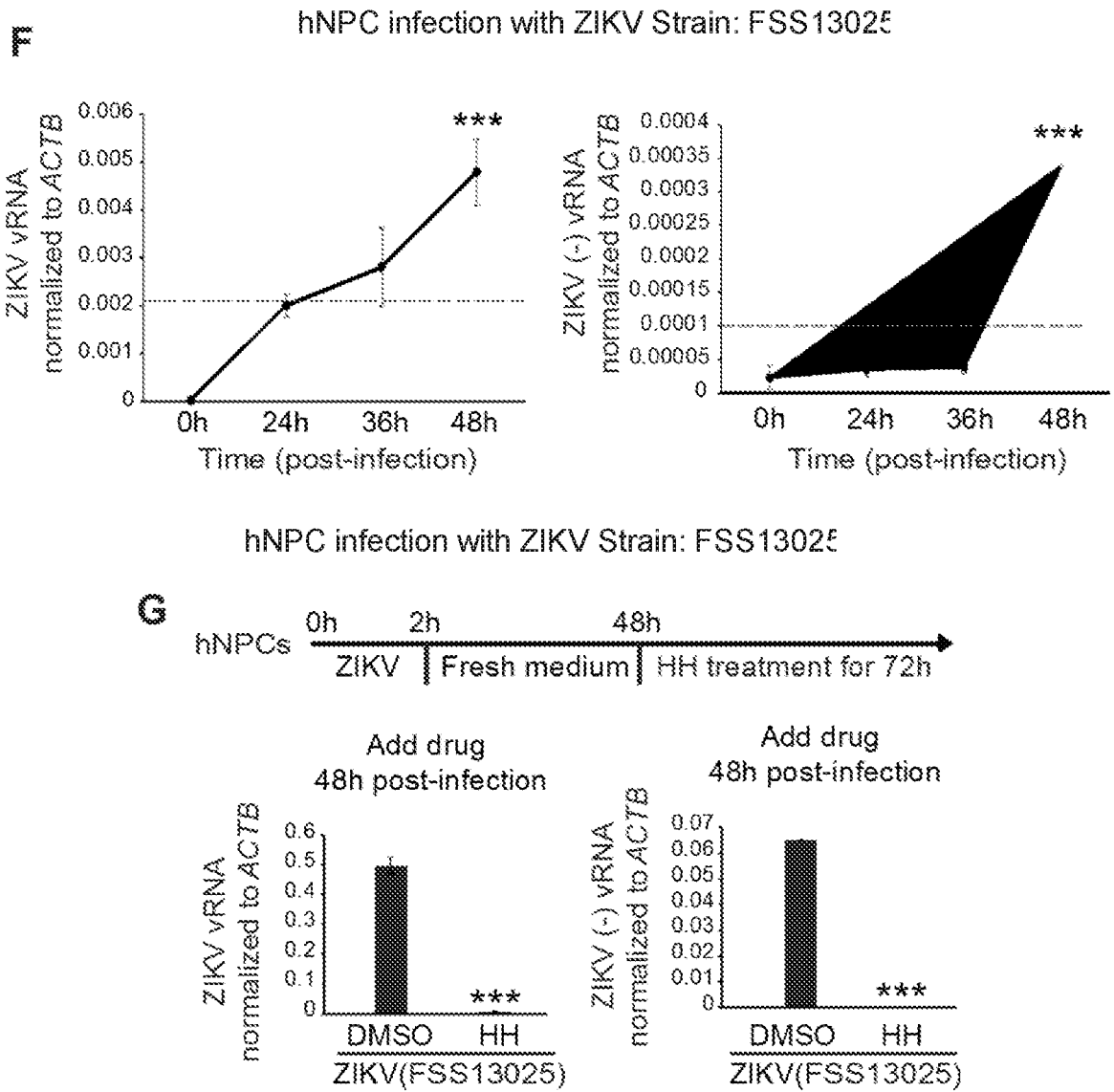

HH eliminates virus from ZIKV infected hNPCs. To determine whether the drug candidates are capable of eliminating ZIKV in previously infected hNPCs, HH or AQ was applied 2 h post ZIKV infection (FIG. 2A). Both compounds were capable of eliminating ZIKV infection, with HH showing comparable $IC_{50}$ values for both inhibiting and eliminating ZIKV (FIG. 2B). In addition, HH successfully rescued ZIKV-induced loss of cell viability in a dose-dependent manner with no obvious cytotoxicity even at the highest dose of 100 µM (FIG. 2C). In contrast, AQ affected cell viability at 25 µM, suggesting that AQ can be toxic to hNPCs (FIG. 6B).

ZIKV-infected hNPCs were treated with HH or AQ for 3 days, followed by 3 days culture in drug-free medium. Immunocytochemical analysis of ZIKV E, cleaved-caspase-3 (CAS3) and DAPI were performed at day 0 (just before ZIKV infection), day 3, and day 6 to measure the ZIKV infection rate, cell death rate and total cell numbers, respectively. Both HH and AQ suppressed ZIKV infection to undetectable levels by day 3 of treatment (FIG. 2D and FIG. 6C). By day 6, following 3 days culture without drug, HH-treated hNPCs remained undetectable for ZIKV infection (FIGS. 2D and 2E). Consistent with these observations, HH treatment also rescued the cell death rate and total cell number at levels comparable to control mock infection conditions (FIGS. 2D and 2E). In addition, neither ZIKV vRNA, as indicated by qRT-PCR (FIG. 2F), or production of infectious ZIKV, as indicated by a Vero cell re-infection assay, was detected in day 6 supernatant of HH-treated conditions (FIGS. 2G and 2H). Furthermore, hNPCs with or without ZIKV infection treated with HH for 3 days maintained the expression of neural progenitor markers, SOX2 and NESTIN, and were capable of differentiation into cortical neurons expressing MAP2 and beta-tubulin III (FIG. 2I). In contrast, hNPCs without HH treatment underwent significant cell death after 3 days of ZIKV infection, and there were no cells detected after cortical neuron differentiation (data not shown). Together, these data strongly suggest that HH can eliminate ZIKV from infected hNPCs without affecting cell identity or differentiation capacity. In contrast to HH treatment, AQ treatment resulted in viral rebound after 3 days of growth in drug-free medium. The percentage of ZIKV infected cells in AQ-treated wells at day 6 is comparable to the level of infection in the DMSO control condition (FIGS. 6C and 6D), suggesting that AQ only transiently suppresses ZIKV infection but fails to effectively eliminate virus from the cells.

To further evaluate the therapeutic potential of HH, qRT-PCR analysis was performed to monitor the dynamics of ZIKV vRNA expression (MR766 strain) in hNPCs. Both total and replicating (−) strand of ZIKV vRNAs could be detected at 24 h post-infection, and the vRNA level kept increasing at 36 h and 48 h post-infection (FIG. 2J). Based on this result, 25 µM HH or DMSO control was added to the hNPC cultures at 24 h, 36 h or 48 h post-infection and maintained for an additional 3 days. HH treatment successfully suppressed the total and replicating (−) ZIKV vRNA levels as indicated by qRT-PCR (FIG. 2K). In addition, to determine the effect of HH on hNPCs derived from different donors, 25 µM HH or DMSO control was added to the hNPCs derived from either of two additional donors at 24 h post-infection. The qRT-PCR data showed that HH consistently suppressed the production of total and replicating (−) strand ZIKV vRNAs in hNPCs derived from different donors (FIG. 6E). Moreover, we evaluated the dynamics of ZIKV vRNA expression (FSS13025 strain) in hNPCs. The qRT-PCR analysis showed that both total and replicating (−) strand of ZIKV vRNAs were detected at 48 h post-infection (FIG. 6F). HH treatment at 48 h post-infection completely suppressed the production of total and replicating (−) strand of ZIKV vRNAs (FIG. 6G). Together, our data show that HH is capable of eliminating virus production from hNPCs carrying replicating ZIKV virus.

HH inhibits ZIKV infection in a human fetal-like forebrain organoid model. hPSC-derived forebrain organoids were developed as a three-dimensional (3D) culture system that recapitulates the multicellular orchestration of human cortical development, providing a unique opportunity to study disorders of brain growth including microcephaly (Bershteyn and Kriegstein, Cell 155, 19-20, 2013). Recently organoids were successfully applied to model ZIKV pathogenesis at different stages of human cortical development (Garcez et al., Science 352, 816-18, 2016; Qian et al., Cell 165, 1238-54, 2016). To further evaluate the anti-ZIKV activity of the hit compounds and their effects on structural brain development, we performed a series of experiments to test the short-term and long-term effects of AQ and HH on day 20 (D20) forebrain organoids following ZIKV infection.

Figure 3:
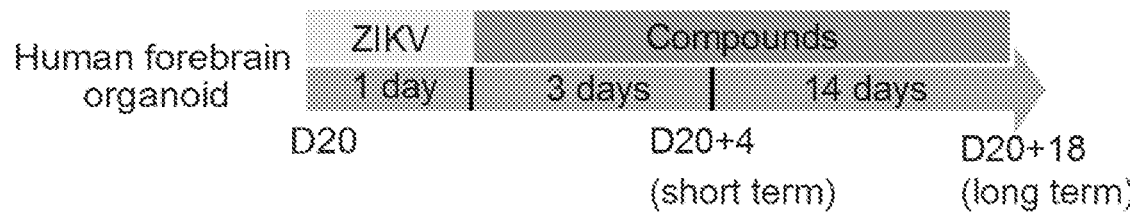
FIG. 3 shows HH inhibits ZIKV infection in short and long term forebrain organoid cultures. (A) Experimental design for evaluating the therapeutic efficacy and safety of HH using forebrain organoids. D20 or D40 Forebrain organoids were exposed to ZIKV ($5 \times 10^5$ PFU/ml) or mock-treated for 24 h. After removal of ZIKV-containing medium, fresh virus-free medium plus compounds were added. Organoids were analyzed at day 4 (D20+4) or day 18 (D20+18) after initial ZIKV infection. (B and C) HH eliminates ZIKV infection in short-term cultures. Immunocytochemistry analysis (B) and the quantification of infection rate (C) of mock, DMSO or 25 µM HH treated ZIKV-infected D20 organoids (n=3). Scale bars, 100 µm. D20+4 organoids mainly consist of $SOX2^+$ progenitors and are highly infiltrated by ZIKV. Treatment with 25 µM HH suppresses the ZIKV levels to below the detection limit. (D) qRT-PCR analysis of total ZIKV vRNA in the supernatant of DMSO or 25 µM HH treated ZIKV-infected D20 and D40 organoids (n=3). (E) HH rescues ZIKV-related proliferation and apoptosis defects in D20+4 organoids. The number of proliferating cells ($Ki67^+$) is decreased and the number of apoptotic cells ($CAS^+$) is increased in ZIKV-infected organoids compared to mock and 25 μM HH treated organoids (n=3). Scale bars, 100 μm. (F) HH suppresses ZIKV infection in long-term cultures. D20+18 organoids are highly infiltrated by ZIKV, while HH suppressed any detectable ZIKV infection (n=3). Scale bars, 50 μm. (G and H) Brightfield images of whole organoids show that HH rescues the ZIKV-associated organoid growth defect (G). Quantifications show average organoid perimeter of D20+18 organoids (H). Values represent mean±SEM (n=3). Scale bars, 1 mm. (I) HH rescues ZIKV-induced structural defects in forebrain organoids. Mock treated organoids contain clearly defined progenitor (SOX2) and neuronal (TUJ1) zones. Neurons migrate out of progenitor zones and settle at the edge of the organoid, while progenitor zones occupy more interior regions of the organoid. In contrast, D20+18 ZIVK infected organoids lack clearly defined progenitor and neuronal zones, which appear to intermix. Both neuron and progenitor zones appear to settle at the edge of the organoid. HH rescues the well-delineated structure of forebrain organoids (n=3). Scale bars, 100 μm. p values were calculated by unpaired two-tailed Student's t-test. *p<0.05, p<0.01 and *p<0.001.
Figure 3:
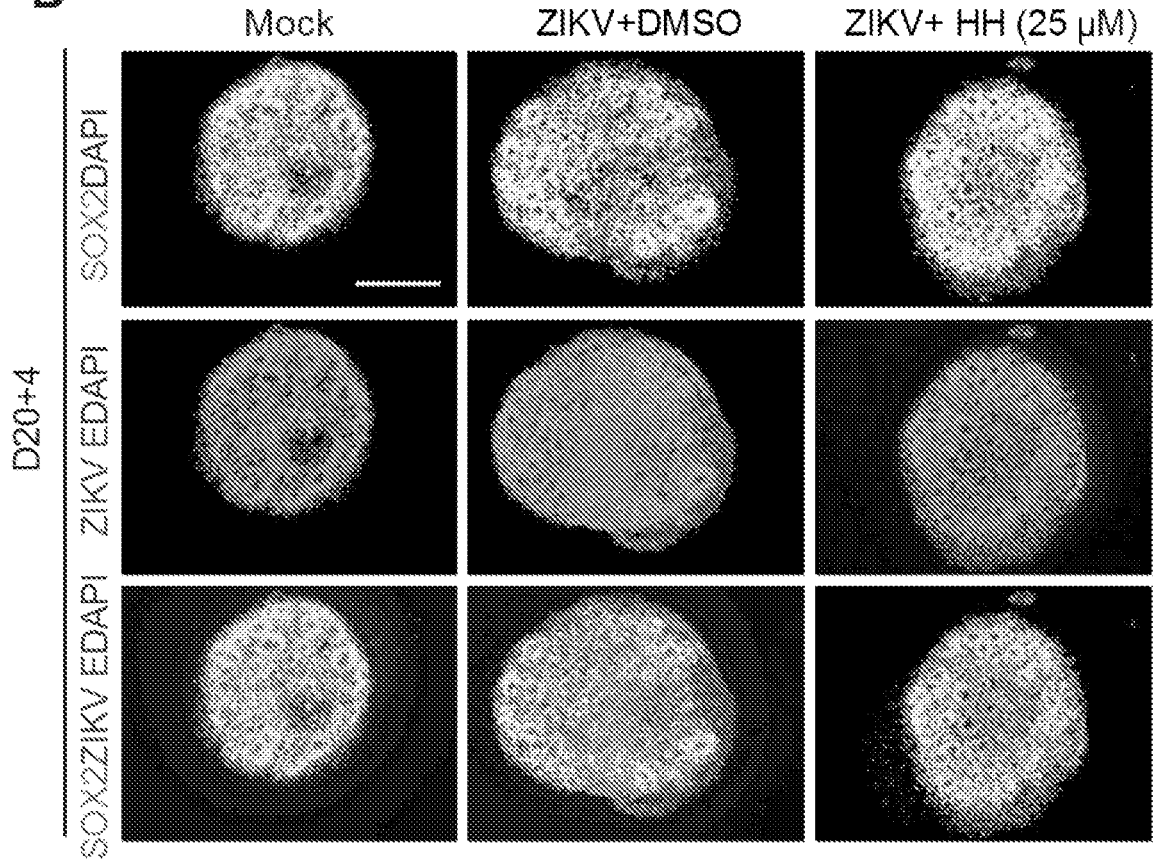
Figure 3:
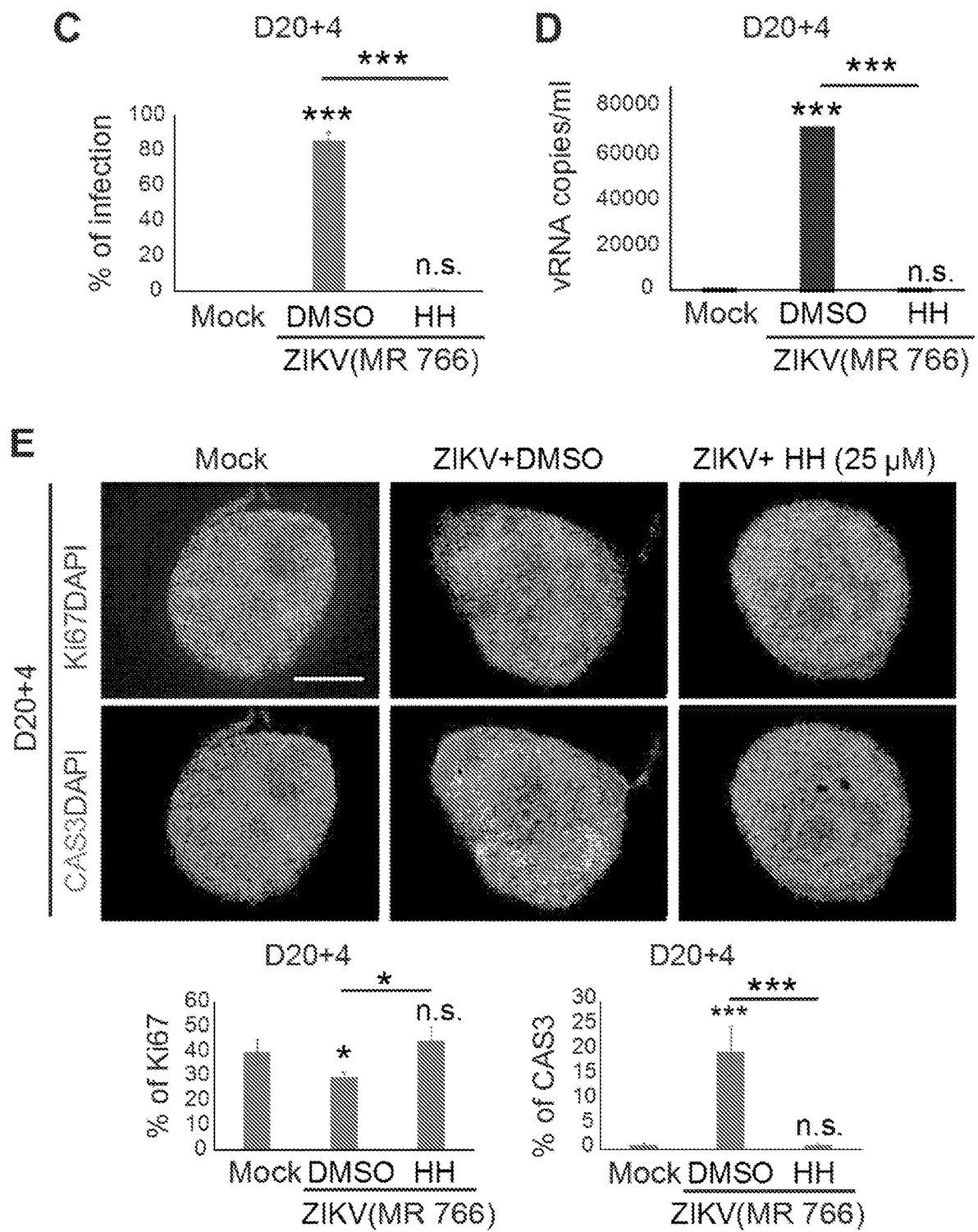
Figure 3:
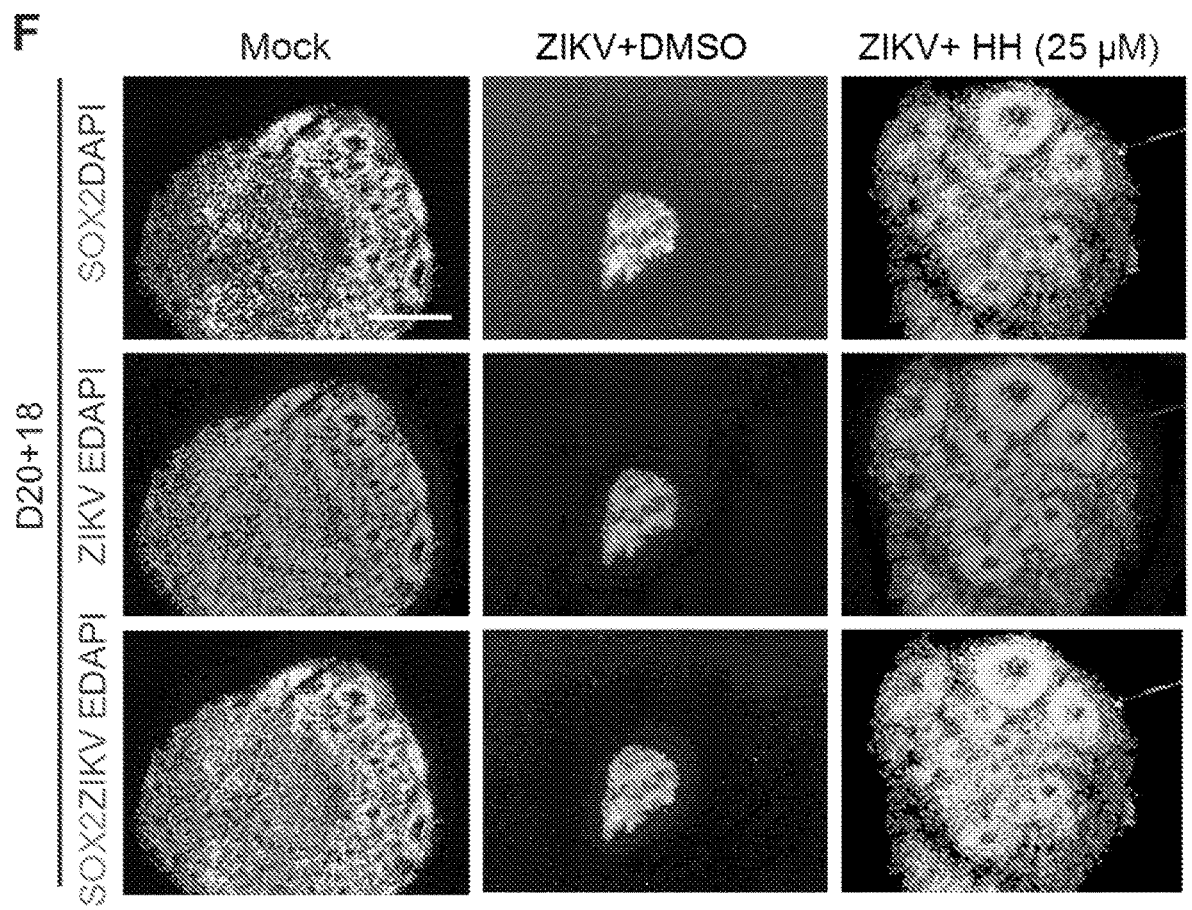
Figure 3:
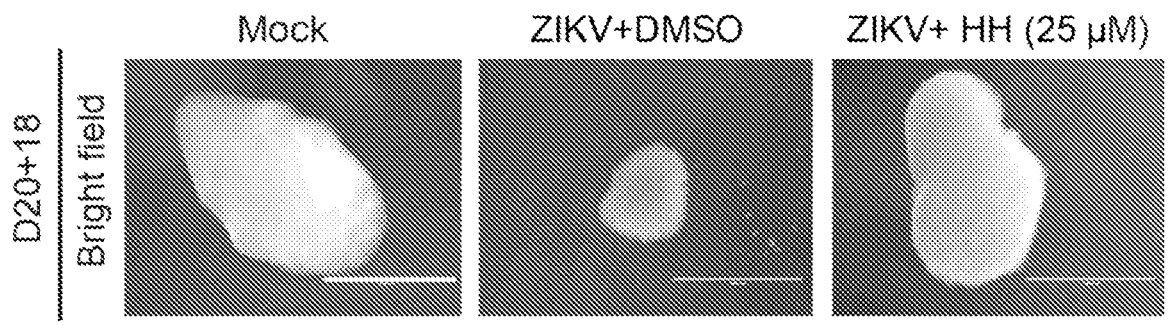
Figure 3:
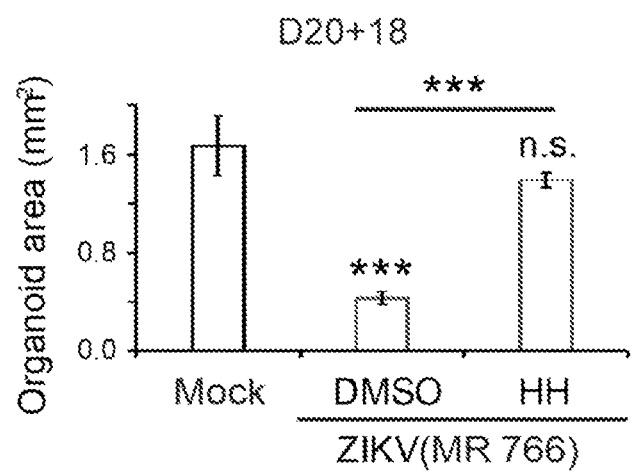
Figure 3:
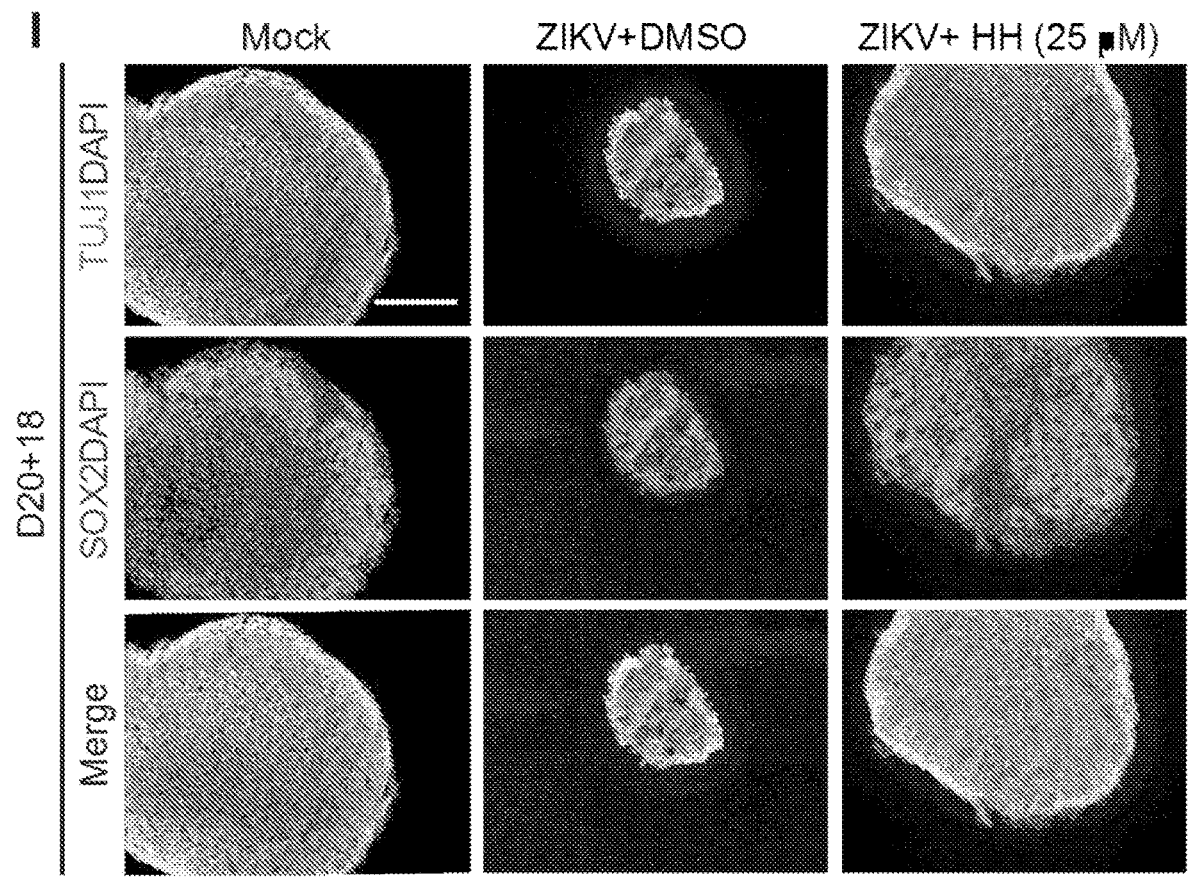

D20 forebrain organoids were inoculated with ZIKV (MR766 strain) for 24 h, followed by treatment with 15 µM AQ or 25 µM HH for 3 days (D20+4, short-term) or 17 days (D20+18, long-term). Organoids were analyzed for ZIKV infection, cell proliferation, and apoptosis (FIG. 3A). Immunohistochemical analysis of SOX2 and ZIKV E showed that D20 forebrain organoids consist mainly of $SOX2^+$ NPCs, and more than 80% of the cells were infected by ZIKV at D20+4 (FIGS. 3B and 3C). Strikingly, 25 µM HH was effective at suppressing the ZIKV infection rate to undetectable levels after the 3 day treatment of D20-infected organoids (FIGS. 3B and 3C). qRT-PCR assays confirmed that HH suppresses total ZIKV vRNA level in the supernatant from D20+4 organoids (FIG. 3D).

Given the ability of HH to eliminate detectable ZIKV infection, we next asked if HH rescues ZIKV-associated proliferation and apoptosis defects. Infection of D20 organoids with ZIKV reduced the relative number of $Ki67^+$ proliferating cells (40±6% in mock, 28±2% in ZIKV, p=0.035), and increased the number of $CAS3^+$ apoptotic cells (1±0.5% mock, 20±5% ZIKV, p=0.0003) 4 days after infection (FIG. 3E). These phenotypes were completely rescued by treatment for 3 days with 25 µM HH (FIG. 3E).

Figure 7:
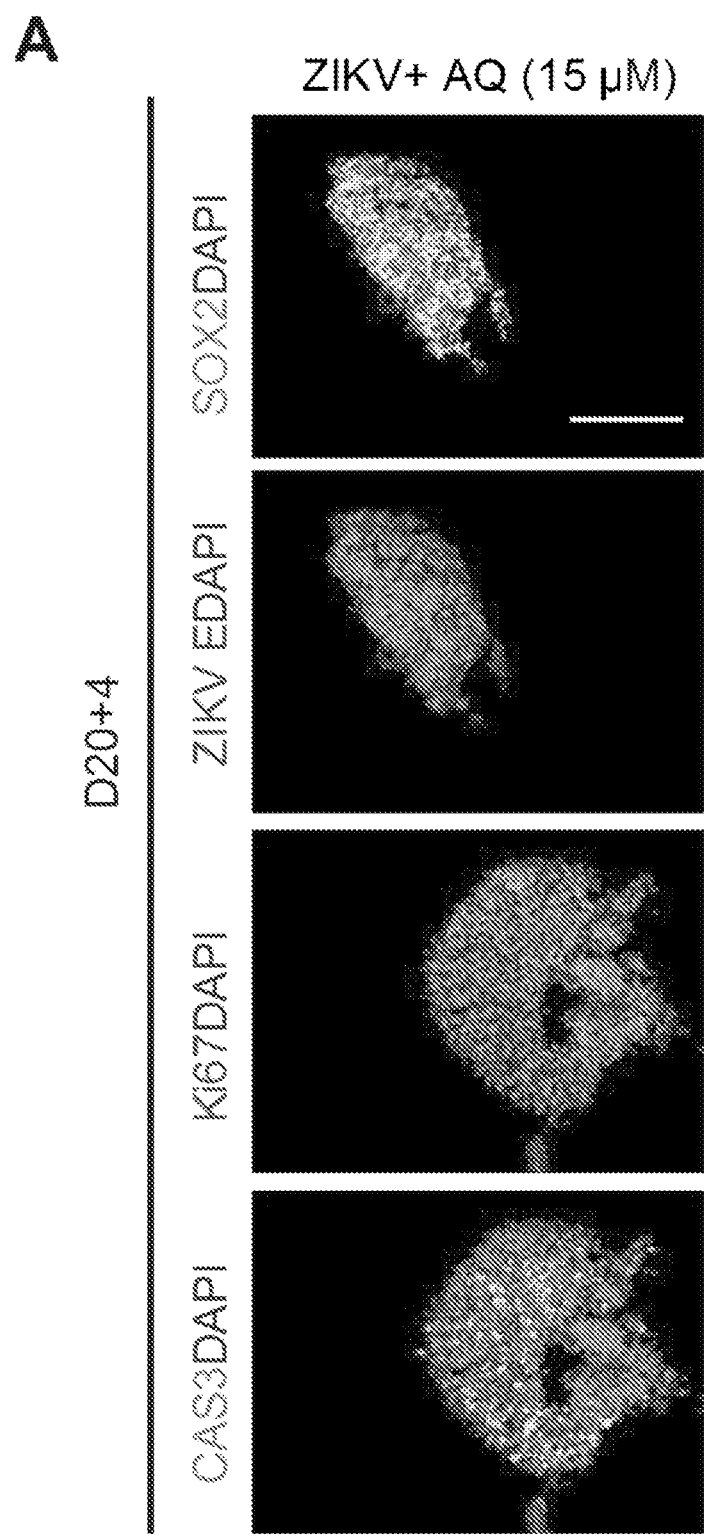
FIG. 7 shows HH, not AQ suppresses virus propagation in ZIKV-infected human forebrain organoids. (A) AQ reduced ZIKV infection, but also induced toxicity in short-term organoid cultures. Immunocytochemical analysis of D20+4 ZIKV-infected organoids treated with 15 μM AQ or DMSO or with mock infection (n=3). D20+4 organoids were stained for SOX2, ZIKV E and with DAPI to monitor the ZIKV infection rate. D20+4 organoids were also stained for Ki67, CAS3 and with DAPI to monitor the cell proliferation and apoptosis rate. Treatment with AQ reduces ZIKV infection, but increases cell apoptosis rate. Scale bars, 100 μm. (B) The expression dynamics of ZIKV vRNA (FSS13025 strain) in human forebrain organoids. qRT-PCR analysis to quantify the total and replicating (−) strand vRNA levels in the human forebrain organoids at different time points post-infection. The dash line shows qRT-PCR detection limit. p values were calculated by one-way repeated measures ANOVA with a Bonferroni test for multiple comparisons. *p<0.05, p<0.01 and *p<0.001. (C) qRT-PCR analysis of human forebrain organoids that were treated with 25 μM HH or DMSO at 42 h or 48 h post-ZIKV (FSS13025 strain) infection and maintained for additional 3 days. p values were calculated by unpaired two-tailed Student's t-test. *p<0.05, p<0.01 and *p<0.001, if not mentioned specifically.
Figure 7:
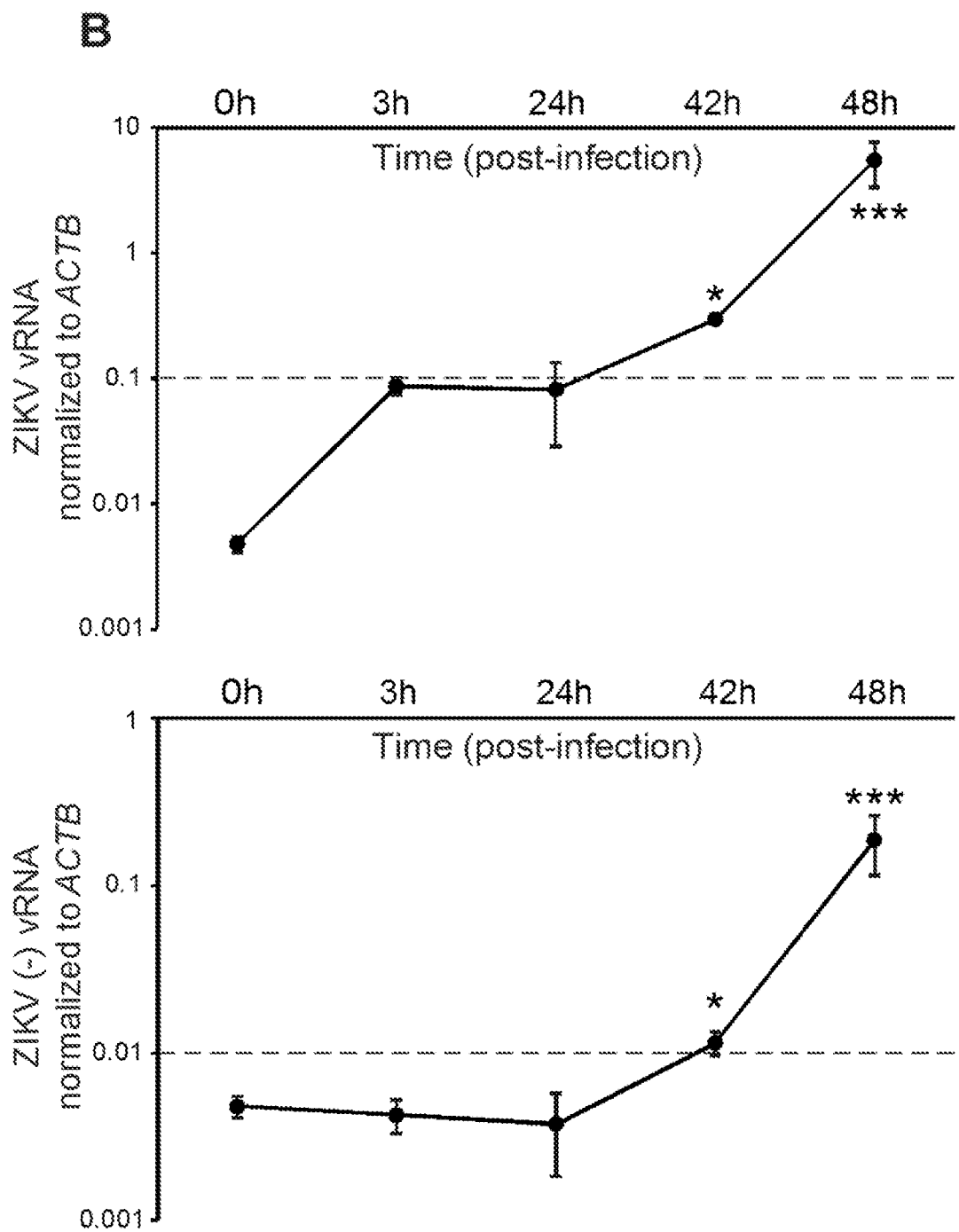
Figure 7:
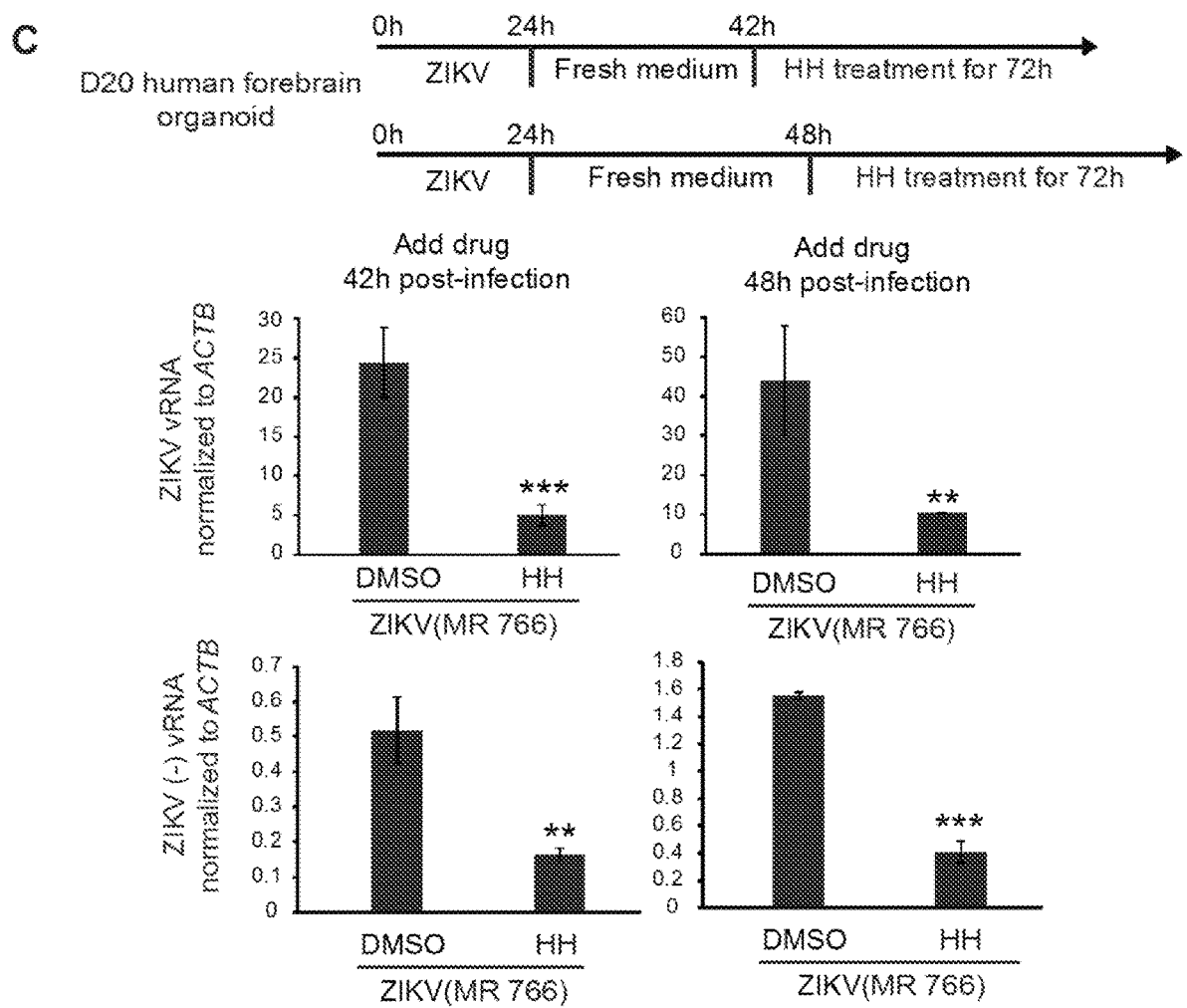

We performed similar experiments with compound AQ. Although 15 µM AQ suppresses ZIKV infection in D20 organoids, it resulted in a substantial reduction in mitotic cells and a substantial increase in apoptotic cells (FIG. 7). This suggests that AQ is an effective anti-ZIKV agent, but the high cellular toxicity in neural progenitors might cause safety concerns. HH did not exhibit similar neurotoxicity as AQ, suggesting a favorable safety profile.

Given the efficacy of HH in short-term organoid cultures, we next assessed whether HH confers durable, long-term control of ZIKV infection and whether it can rescue microcephaly-related defects caused by ZIKV infection. D20 organoids were infected with ZIKV and after 18 additional days of growth, analyzed for ZIKV infection. Immunohistochemical analysis of SOX2 and ZIKV E in D20+18 organoids shows that HH treated organoids were devoid of any detectable ZIKV, while ZIKV infected organoids without drug treatment were strongly infiltrated by virus (FIG. 3F).

To determine whether HH rescues microcephaly-related pathologies, organoid size was measured 18 days after infection. At D20+18, the cross-sectional area of ZIKV infected organoids was significantly decreased compared to mock infected conditions, consistent with ZIKV-associated microcephaly in infants (mock, 1.6 $mm^2$; ZIKV, 0.4 $mm^2$, p=0.0009, FIGS. 3G and 3H). In contrast, ZIKV-infected organoids that were treated with 25 μM HH grew to a similar size as mock-infected organoids (HH, 1.4 mm$^2$, FIGS. 3G and 3H). Moreover, HH successfully rescued ZIKV-induced structural defects seen in long-term cultures. Similar to the mock condition, in the ZIKV-infected organoids treated with 25 μM HH, there are clearly defined zones of progenitors (SOX2$^+$) and neurons (TUJ1$^+$), while in the ZIKV infected organoids treated with DMSO, the progenitor and neuronal zones are intermixed and lack any discernible organization (FIG. 3I). Together, these data indicate that HH successfully inhibits ZIKV activity during long-term forebrain organoid growth and rescues crucial aspects associated with fetal brain development.

To further validate the effect of HH on ZIKV-infected brain organoids, we first monitored ZIKV vRNA expression dynamics in organoids using qRT-PCR analysis. Both total and replicating (−) strand of ZIKV vRNA levels were detected at 42 h post-infection, and the virus level was significantly increased at 48 h post-infection (FIG. 7B). HH treatment significantly decreased the total and replicating (−) ZIKV vRNA levels when added at 42 h or 48 h post-infection and maintained for additional 3 days (FIG. 7C).

Figure 8:
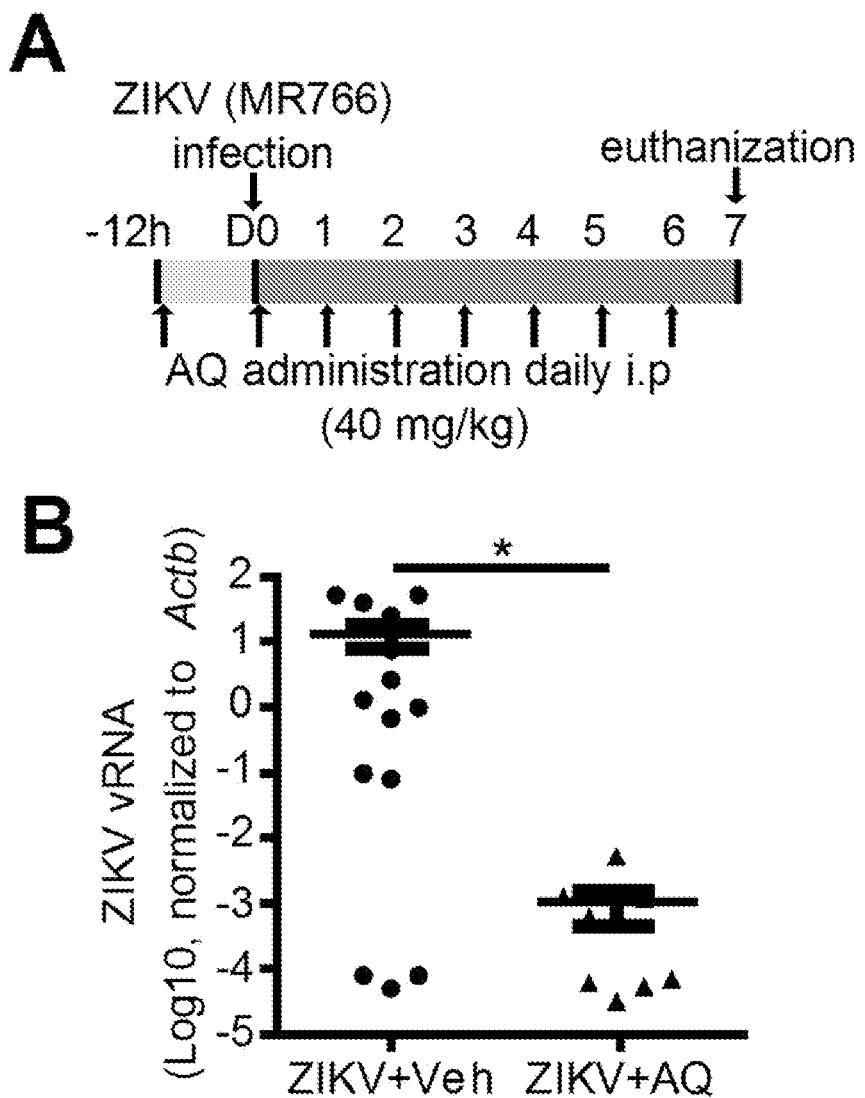
FIG. 8 shows AQ suppresses ZIKV infection in vivo. (A) Scheme of prophylactic treatment of HH in vivo. HH was administrated to SCID-Beige mice 12 h before infection with MR766 virus strain. HH was injected at a dose of 100 mg/kg/day subcutaneously and euthanized at day 7. (B) qRT-PCR analysis of ZIKV vRNA in brains of ZIKV-infected mice treated with vehicle (n=14) or AQ (n=9). Normalized to Beta-Actin. (C-E) Immunohistochemical analysis of ZIKV in adult cortex of AQ-treated ZIKV infected mice (n=6) (C), and co-staining with neuron marker TUJ1 (D) and astrocyte marker GFAP (E). AQ suppresses infection in adult cortex. Scale bar=100 μm in (C) and 10 μm in (D, E). (F-H) Immunohistochemical analysis of ZIKV in adult hippocampus of AQ-treated ZIKV infected mice (n=6) (F), and co-staining with neural progenitor marker SOX2 (G) and immature neuron marker DCX (H). AQ suppresses infection in adult hippocampus. Scale bar=100 in (F) and 10 μm in (G, H). (I-K) Immunohistochemical analysis of ZIKV in adult striatum of AQ-treated ZIKV infected mice (n=6) (I), and co-staining with neural progenitor marker SOX2 (J) and immature neuron marker DCX (K). AQ suppresses infection in adult striatum. Scale bar=100 μm in (H) and 10 μm in (J, K). (L) Immunohistochemical analysis of cell apoptosis in brain of ZIKV infected mice treated with AQ (n=6). No apoptosis is detected in the presence of AQ. Scale bar=100 μm. p values were calculated by one-way repeated measures ANOVA or two-way repeated measures ANOVA with a Bonferroni test for multiple comparisons. *p<0.05, p<0.01 and *p<0.001.
Figure 8:
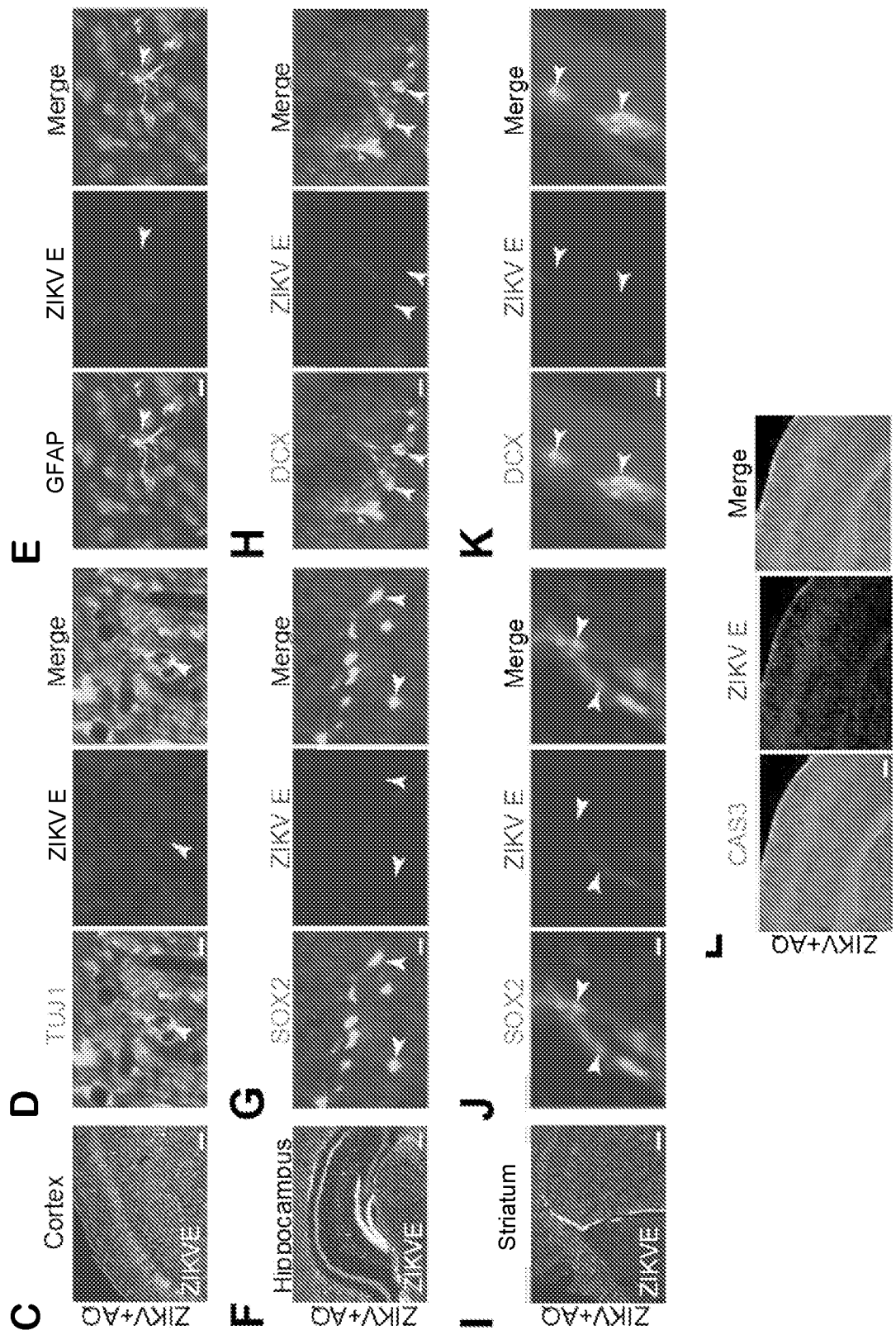

HH or AQ suppresses ZIKV infection in vivo. To evaluate the prophylactic activity of drug candidates in vivo, HH or AQ was administrated to 6-8 week old SCID-Beige mice 12 h before they were infected with MR766 virus strain. HH was injected at a dose of 100 mg/kg/day subcutaneously (FIG. 4A), and AQ was administrated at a dose of 40 mg/kg/day through intraperitoneal injection (FIG. 8A). PBS, the solvent used to dissolve both compounds, was used as vehicle control.

Figure 4:
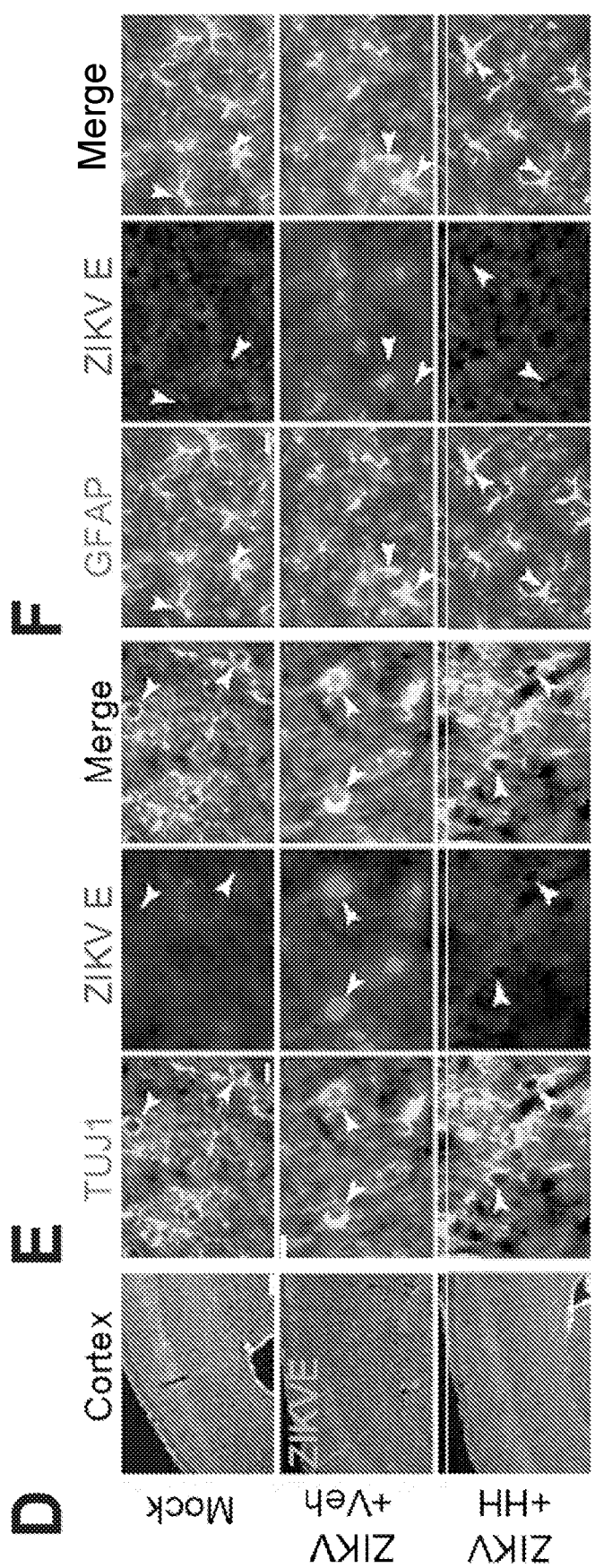
FIG. 4 shows HH suppresses ZIKV infection in vivo. (A) Scheme of prophylactic treatment of HH in vivo. HH was administrated to SCID-Beige mice 12 h before infection with MR766 virus strain. HH was injected at a dose of 100 mg/kg/day subcutaneously and euthanized at day 7. (B) qRT-PCR analysis of total ZIKV vRNA in liver, spleen, kidney and brain of ZIKV infected mice. n=12 for liver, spleen and kidney and 20 for brain. (C) qRT-PCR analysis of total ZIKV vRNA in brains of ZIKV-infected mice treated with vehicle (n=14) or HH (n=8). Black line shows the detection limit for qRT-PCR. (D-F) Immunohistochemical analysis of adult cortex. ZIKV strongly infects adult cortex (n=11) and infection is completely inhibited by HH (n=8) (D). Co-staining with neuron marker TUJ1 shows that neurons are highly infected by ZIKV (E) while cortical astrocytes are rarely infected by ZIKV (F). HH prevents infection in all cortical cells. Scale bar=100 μm in (D) and 10 μm in (E, F). (G-I) Immunohistochemical analysis of adult hippocampus. ZIKV strongly infects adult hippocampus including the post-mitotic cornu amonis (CA) regions (n=11) and infection is completely inhibited by HH (n=8) (G). Co-staining with neural progenitor marker SOX2 (H) and immature neuron marker DCX (I) shows some infection of both immature cell types. HH inhibits infection of all cells in the hippocampus. Scale bar=100 μm in (G) and 10 μm in (H, I). (J-L) Immunohistochemical analysis of adult striatum. ZIKV strongly infects adult striatum (n=11) and infection is completely inhibited by HH (n=8) (J). Co-staining with neural progenitor marker SOX2 (K) and immature neuron marker DCX (L) reveals that ZIKV infects few if any immature cell types in the subventricular zone. The majority of ZIKV expression appears to be outside the subventricular zone, consistent with infection of post-mitotic neurons. Scale bar=100 μm in (J) and 10 μm in (K, L). (M, N) Immunohistochemical analysis of cellular apoptosis in adult cortex. ZIKV infection induces cellular apoptosis in adult cortex when compared to mock infection (n=11), and this is completely inhibited by treatment with HH (n=8) (M). ZIKV induces apoptosis of both infected and non-infected cells (N). Scale bar=100 μm in (M) and 10 μm in (N). (O, P) Expression kinetics of total vRNA (O) and (−) strand vRNA (P) of ZIKV (MR766 strain) in mouse brain. N is larger or equal to 4 mice at each time points. The mice were inoculated with ($1\times10^6$ PFU) through intraperitoneal injection. The mice were euthanized at 12 h, 24 h, 3 days, 4 days and 5 days post-infection. (Q) Scheme of therapeutic treatment of HH on ZIKV (MR766 strain) infected mice. The SCID-beige mice were infected with ZIKV (MR766 strain, $1\times10^6$ PFU). The mice at 5 days post-infection were treated with 100 mg/kg HH or vehicle daily for 5 days. The mice were then euthanized and RNA from brains was analyzed using qRT-PCR. (R, S) qRT-PCR analysis of total vRNA (R) and (−) strand RNA (S) in the brains of mice treated with vehicle (n=8) or HH (n=8) at day 5 post-infection. (T, U) Expression kinetics of total vRNA (N) and (−) strand vRNA (O) of ZIKV (FSS13025 strain) in mouse brain. N is larger or equal to 4 mice at each time points. The mice were inoculated with ($3\times10^6$ PFU) through intraperitoneal injection. The mice were euthanized at 12 h, 24 h, 3 days, 5 days and 7 days post-infection. (V) Scheme of therapeutic treatment of HH on ZIKV (FSS13025 strain) infected mice. The SCID-beige mice were infected with ZIKV (FSS13025 strain, $3\times10^6$ PFU). The mice at 7 days post-infection were treated with 100 mg/kg HH or vehicle daily for 7 days. The mice were euthanized after 7 days treatment and RNA from brains was analyzed using qRT-PCR. (W, X) qRT-PCR analysis of total vRNA (W) and (−) strand RNA (X) in the brains of mice treated with vehicle (n=8) or HH (n=11) at day 7 post-infection. p values were calculated by one-way repeated measures ANOVA or two-way repeated measures ANOVA with a Bonferroni test for multiple comparisons. *p<0.05, p<0.01 and *p<0.001.
Figure 4:
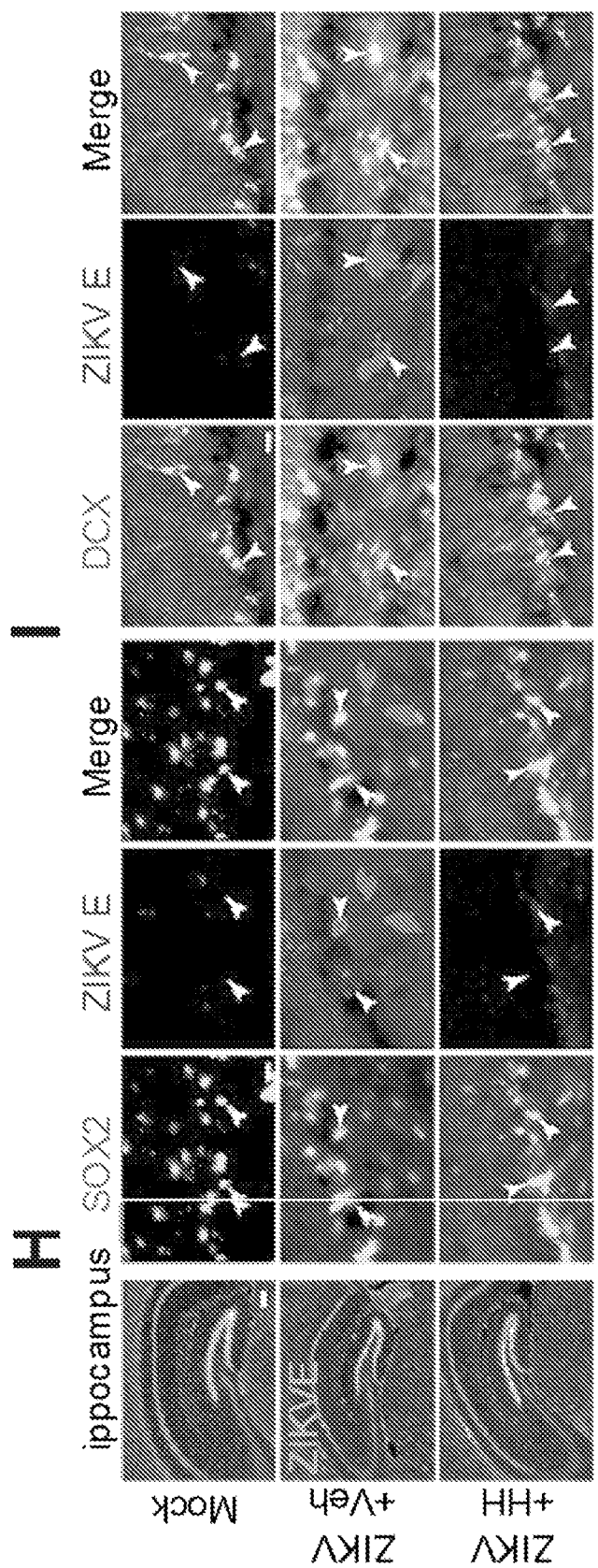
Figure 4:
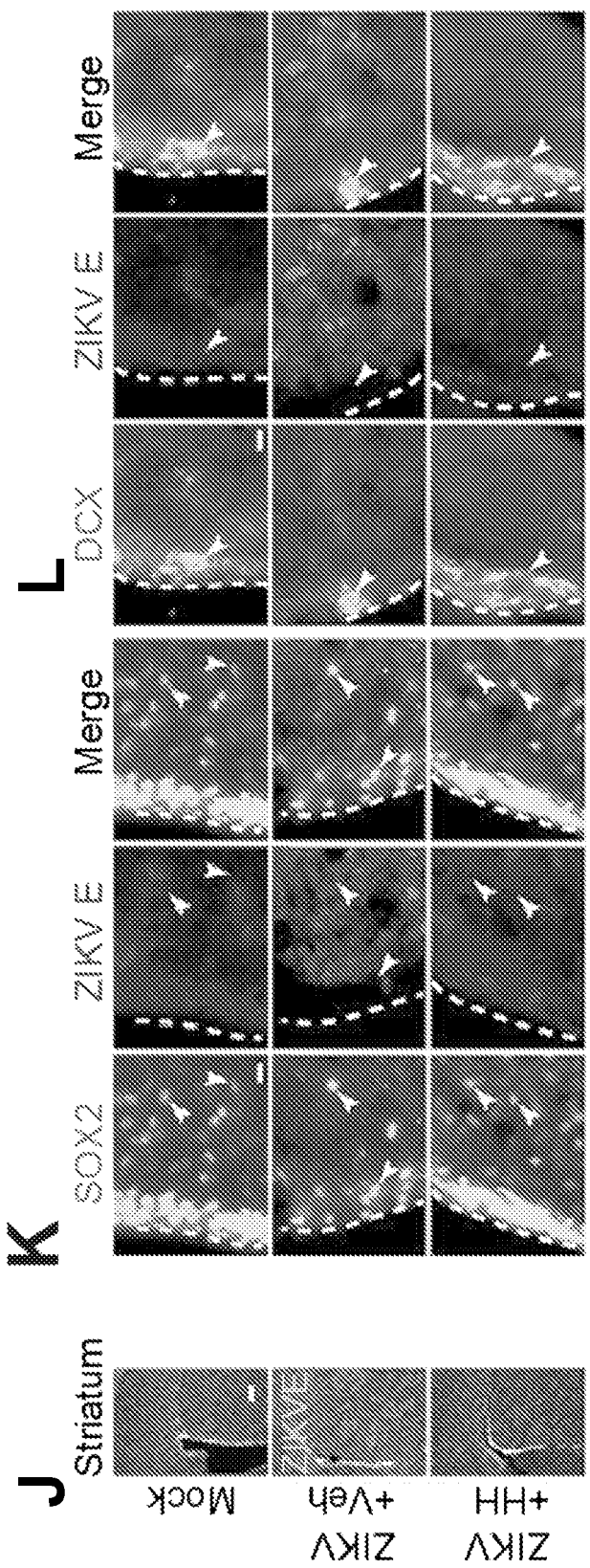
Figure 4:
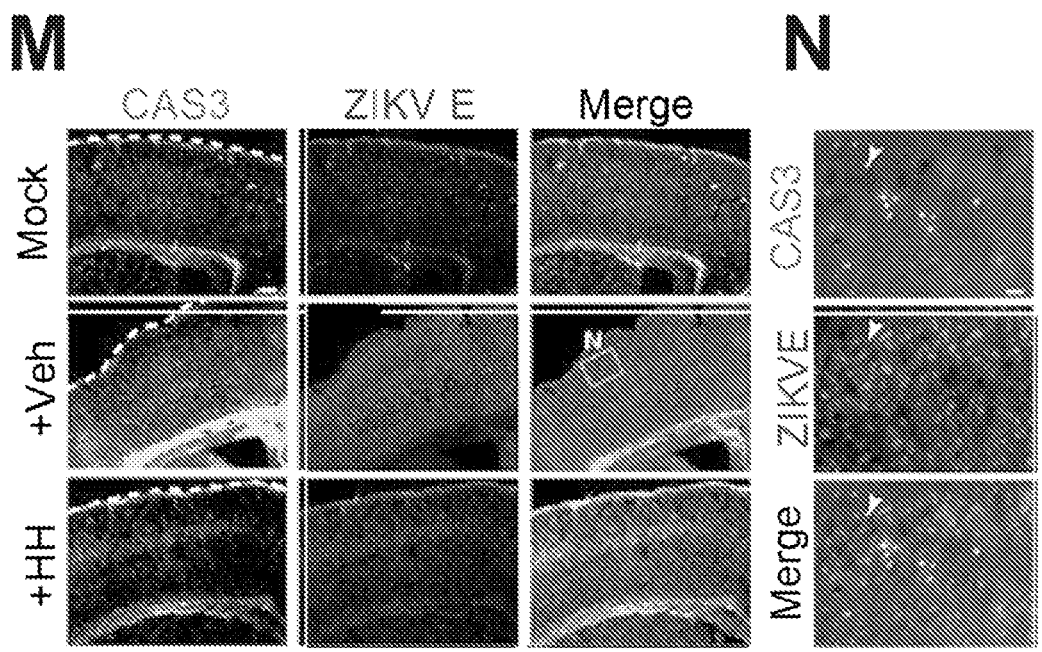
Figure 4:
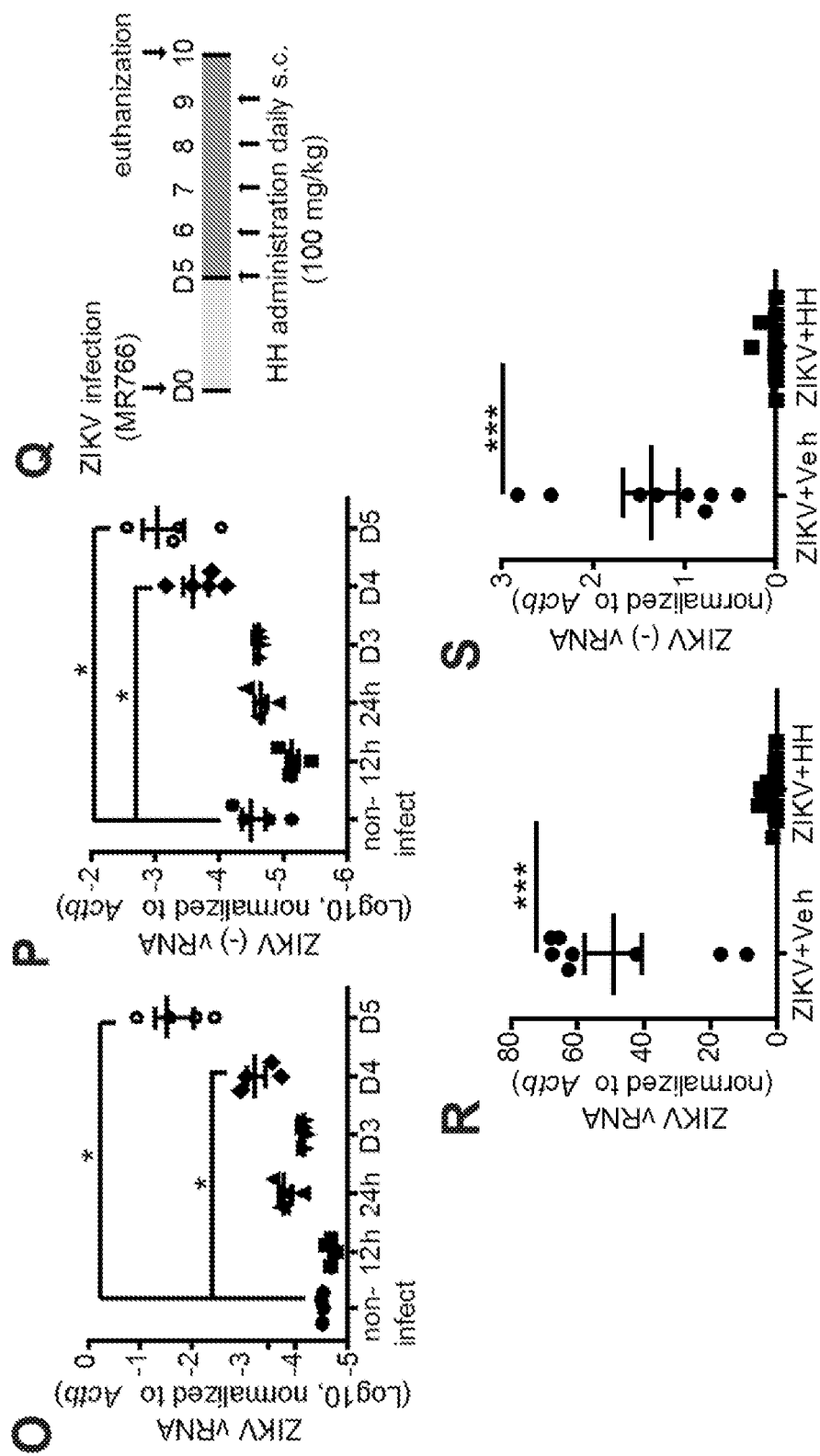
Figure 4:
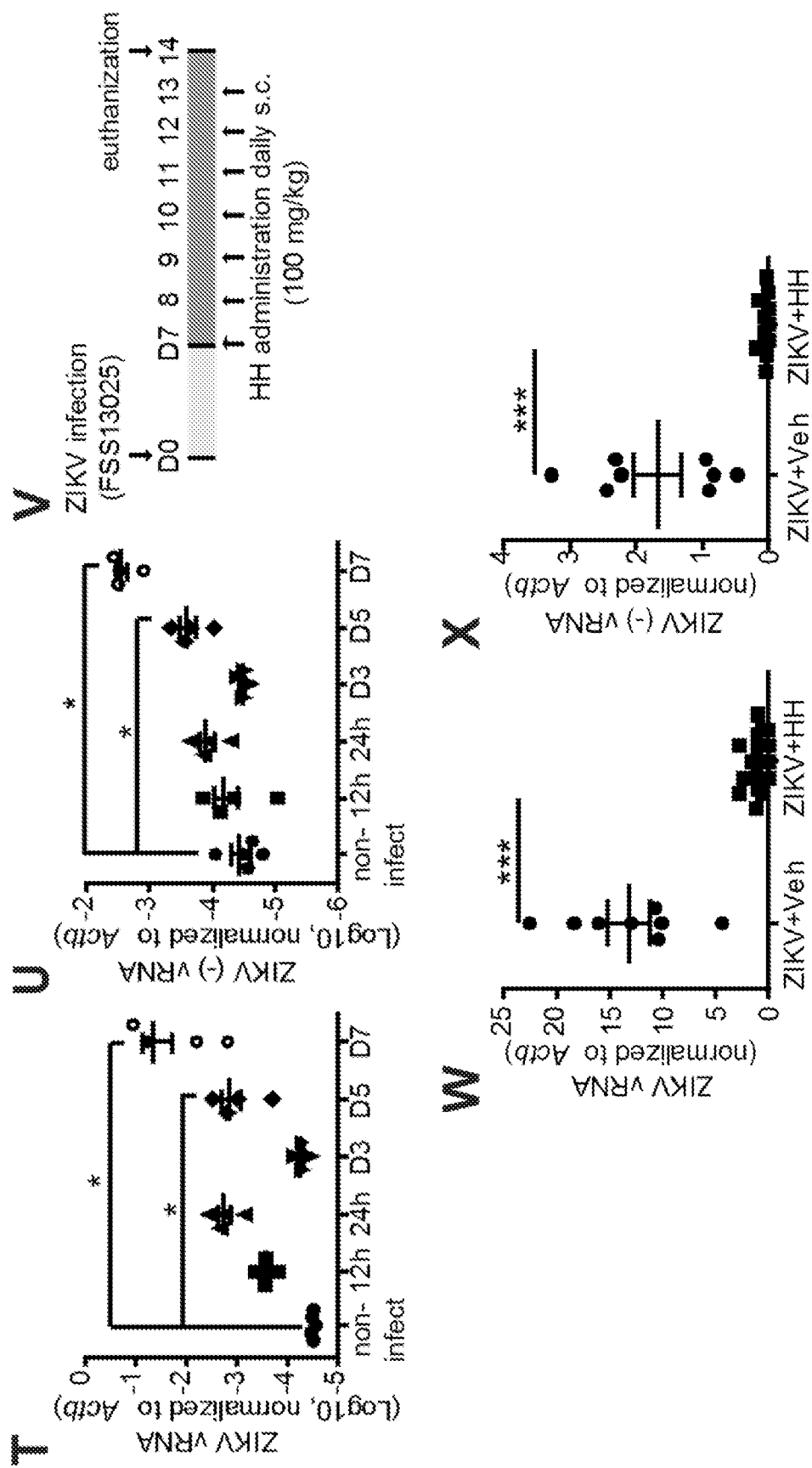

The mice were euthanized at day 7 post-infection. Total ZIKV vRNA was then quantified in multiple organs of ZIKV-infected mice treated with vehicle, including liver, spleen, kidney and brain (FIG. 4B). The levels of total ZIKV vRNA in liver, spleen and kidney was low (FIG. 4B). However, strong ZIKV infection was detected in the brains of many of the infected mice (FIG. 4B). Strikingly, HH treatment suppressed ZIKV vRNA in brain to a significantly lower level (FIG. 4C). AQ treatment achieved similar effects by suppressing brain infection (FIG. 8B).

We next determined the brain structures and cell types infected by ZIKV in this in vivo model system, and asked whether HH inhibits infection in each of these areas. Immunohistochemical analysis revealed that ZIKV broadly infects forebrain structures, with strong infiltration of the adult cortex (FIG. 4D). Interestingly, ZIKV is found in many post-mitotic TUJ1$^+$ cortical neurons (FIG. 4E), but in far fewer, if any, GFAP$^+$ cortical astrocytes (FIG. 4F). HH fully inhibits infection of adult cortex (FIG. 4D-F). ZIKV also strongly infiltrates hippocampal structures, including the cornu ammonis (CA1 and CA3) regions, suggesting infection of post-mitotic neurons (FIG. 4G). In addition, high magnification images reveal that ZIKV can infect SOX2$^+$ neural progenitors (FIG. 4H) and DCX$^+$ immature neurons (FIG. 4I). HH completely inhibits infection of the adult hippocampus, including immature cells (FIG. 4G-I). Finally, ZIKV strongly infiltrates the striatum (FIG. 4J). Interestingly, ZIVK appears to localize outside the neurogenic subventricular zone (SVZ). High magnification imaging reveals few ZIKV-infected SOX2$^+$ neural progenitors (FIG. 4K) or DCX$^+$ immature neurons (FIG. 4L). HH fully inhibits infection of the adult striatum (FIG. 4J-L).

Given the strong infiltration of adult brain structures by ZIKV, we analyzed whether ZIKV exerts detrimental cellular effects in the adult nervous system. Immunostaining for CAS3 reveals that ZIKV infection increases the number of apoptotic cells in the cortex (FIG. 4M). ZIKV induces apoptosis in both infected and non-infected cells (FIG. 4N). Treatment of mice with HH rescues cellular apoptosis associated with ZIKV infection in the cortex (FIG. 4M). Like HH, AQ treatment was also able to inhibit ZIKV infection from all cell-types in the adult (FIG. 8C-K) and to rescue ZIKV-induced cellular apoptosis (FIG. 8L).

To evaluate the therapeutic potential of HH, we first monitored the kinetics of ZIKV infection (MR766 strain) in the adult mouse brain. SCID-beige mice were inoculated with ZIKV by intraperitoneal injection. The mice were euthanized at 12 h, 24 h, 3 days, 4 days and 5 days post-infection and the mouse brains were analyzed for vRNA by qRT-PCR. Both total and replicating (−) strand vRNA levels in the brains of ZIKV-infected mice at day 4 post-infection were significantly higher than those in the brains of mice before infection (FIGS. 4O and 4P) and the vRNA levels kept increasing to day 5. At day 5, which is 24 h after detection of replicating ZIKV vRNA in mouse brain, the ZIKV-infected mice were randomly separated into two groups and treated with vehicle or HH compound (100 mg/kg/day subcutaneously), respectively, for 5 days (FIG. 4Q). The total and replicating (−) strand vRNA levels in brains were quantified by qRT-PCR. HH treatment significantly decreased both total and replicating (−) vRNA levels (FIGS. 4R and 4S). To determine the effect of HH on the Asian ZIKV strain, we first monitored the kinetics of the ZIKV infection (FSS13025 strain) in mouse brain. Both total and replicating (−) strand vRNA levels in the brains of ZIKV-infected mice at day 5 post-infection are significantly higher than those in the brains of mice before infection and vRNA levels kept increasing to day 7 (FIGS. 4T and 4U). At day 7, which is 48 h after detection of replicating ZIKV vRNA in mouse brain, the ZIKV-infected mice were treated with vehicle or HH compound (100 mg/kg/day subcutaneously), respectively, for 7 days (FIG. 4V). Consistent with the data on the MR766 stain, HH treatment significantly decreased the levels of total and replication (−) strand vRNA of ZIKV (FSS13025 strain) in mouse brain after 7 days treatment (FIGS. 4W and 4X). Together, these data demonstrate that in immuno-compromised adult hosts, ZIKV has the ability to achieve disseminated infection outside of progenitor zones, where it typically resides. Furthermore, HH has broad anti-ZIKV activity in both adult progenitor and neuronal cells.

Discussion. We successfully carried out a high content chemical screen using an FDA-approved drug library to identify two drug candidates that have anti-ZIKV activity in hNPCs. Two drug candidates, HH and AQ, can eliminate ZIKV from hNPCs previously infected with ZIKV. In doing so, HH rescues microcephaly-related defects in human fetal forebrain-like organoid cultures, with little or no evidence of cellular toxicity. Finally, HH exhibits anti-ZIKV activity in vivo in the adult mouse brain. We show that HH has strong in vivo activity, inhibiting virus production and spread in ZIKV-infected immuno-compromised SCID mice.

ZIKV infection in the adult brain was previously shown to be localized to progenitors and immature neurons of the adult neurogenic zones (Li et al., Cell Stem Cell 109 593-98, 2016b). Our study confirms that ZIKV infects adult neural progenitors and immature neurons, but extends these findings by showing that ZIKV can also achieve disseminated infection in mature neurons. Our observation may have been facilitated by using a severe combined immunodeficiency (SCID) mouse model, while Li et al. used an interferon regulatory factor (IRF) deficient mouse model. This suggests that adaptive immunity might play an important role in preventing disseminated ZIKV infection.

In addition to HH, we identified another FDA approved drug, Amodiaquine dihydrochloride dihydrate (AQ), also called Amodiaquine, as an anti-ZIKV compound. The WHO recommended AQ as an optional treatment of uncomplicated malaria (Olliaro and Mussano, Cochrane Database Syst Rev 2, 2003). AQ has activity against another flavivirus, Dengue virus, by inhibition of Dengue virus type 2 replication and infectivity (Boonyasuppayakom et al., Antiviral Research 106, 125-34, 2014). A recent report showed that the treatment of AQ-artesunate on patients with confirmed Ebola virus disease significantly lowers risk of death compared to the control group (Gignoux et al., NEJM 374, 23-32, 2016). We found that AQ effectively inhibits ZIKV infection in NPCs in vitro and in the mouse model. However, AQ exhibited high cytotoxicity in brain organoid cultures, which raises safety concerns for using this drug in pregnancy. It has been reported that AQ is a potent inhibitor of histamine-N-methyltransferase (Horton et al., J Mol Bop 353, 334-44, 2005).

Methods

Human cortical neural progenitor cell (hNPC) culture and cortical neuron differentiation. hNPCs were derived and validated as previously described (Topol et al., J Vis Exp, e52495, 2015). Cells were maintained on growth factor reduced Matrigel (BD Biosciences) coated plates in NPC media, including Dulbecco's Modified Eagle Medium/Ham's F12 Nutrient Mixture (ThermoFisher Scientific), 1×N2 (ThermoFisher Scientific), 1×B27 minus RA (ThermoFisher Scientific) and 20 ng/ml recombinant human basic FGF (Peprotech), and split at 1:3 ratio every week with Accutase (Millipore).

To induce cortical neuronal differentiation, NPCs were dissociated with Accutase and plated at $2.0 \times 10^5$ cells per $cm^{-2}$ in NPC media on growth factor reduced Matrigel-coated plates. After overnight culture, media was changed to neural differentiation medium, including DMEM/F12, 1×N2, 1×B27 minus RA, 20 ng/ml BDNF (Peprotech), 20 ng/ml GDNF (Peprotech), 20 ng/ml NT-3 (Peprotech), 1 mM dibutyryl-cyclic AMP (Sigma), 200 nM ascorbic acid (Sigma) and 1 µg/ml laminin (ThermoFisher Scientific). NPC-derived neurons were differentiated for 1~2 months.

Generation and culture of human forebrain organoids. To induce forebrain organoid differentiation, H9 hESC line (WA-09, WiCell) hPSCs were dissociated to single cells using EDTA, and 9000 cells were reaggregated using low-adhesion V-bottom 96 well plates (Wako) in Essential8 Medium (Fisher Scientific) with 10 µM Y-27632 (Tocris Biosciences). After 24 h (day 0), medium was changed to Essential6 (Fischer Scientific) supplemented with 10 µM SB431542 (Tocris Biosciences), 500 nM LDN193189 (Stem Cell Technologies), and 2 µM XAV939 (Tocris Biosciences) until day 4. From day 4 to day 18, XAV939 was removed. Medium was changed every other day. From Day 18, organoids were maintained in organoid differentiation medium (50% DMEM F-12 (Fisher Scientific), 50% mL Neurobasal (Fisher Scientific), 0.5×N2 supplement (Stem Cell Technologies), 0.025% insulin (Sigma), 5 mM L-Glutamine (1×, Fischer Scientific), 0.7 mM MEM-NEAA (1×, Fischer Scientific), 50 U/mL Penicillin-Streptomycin (1×, Fischer Scientific), 55 µM 2-mercaptoethanol (1×, Fischer Scientific), 1×B27 supplement without Vitamin A (Fischer Scientific).

ZIKV infection of hNPCs and forebrain organoids. Vero cell line was maintained in EMEM medium (Gibco) plus 10% heat-inactivated FBS with penicillin/streptomycin at 37° C. MR766 strain and PRVABC59 strain of ZIKV were obtained commercially (ZeptoMetrix) and then titrated by plaque assay in Vero cells. FSS13025 strain was propagated using Vero cells as described previously (Li et al., Cell Stem Cell 109 593-98, 2016b).

hNPCs were plated on 96-well plates at $8.5 \times 10^4/cm^2$. After overnight incubation, hNPCs were infected with ZIKV (MR766 strain, MOI=0.125) for 2 h, and changed to virus-free medium. The cells were maintained in NPC medium with daily medium change. Three days later, the supernatant and cells were collected and used for assays. hESC-derived forebrain organoids were infected with ZIKV MR766 ($5 \times 10^5$ PFU/ml) for 24 h. After removal of virus containing medium, forebrain organoids were maintained in forebrain organoid medium for an additional 3 or 17 days and then used for assays.

To monitor ZIKV dynamics in hNPCs, hNPCs were infected with ZIKV (MR766 strain, MOI=0.125, FSS13025 strain MOI=0.1) for 2 h, and changed to virus-free medium. The cells were maintained in NPC medium with daily medium change. The cells were lysed at the different time points and analyzed using qRT-PCR.

High-content Screen. hNPCs were dissociated and plated on Matrigel-coated 384-well plates for the chemical screen. After overnight incubation, the cells were treated with compounds from an FDA-approved drug library for 1 h with final concentration at 10 µM. DMSO was used as a negative control. ZIKV MR766 was added at MOI=0.125. After 2 hour infection, the supernatant was replaced with fresh medium and compounds from the same chemical library were added to the same wells. After an additional 3 days incubation, cells were fixed, stained with antibodies against ZIKV envelop protein (ZIKV E) and proliferation marker Ki67, and analyzed with the ImageXpress$^{MICRO}$ Automated High-Content Analysis System. A two dimensional analysis was performed to pick the primary hit compounds (FIG. 5A). X-axis represents the fold change of total cell number, which was calculated by dividing the total cell number of the chemical treated well by the average of total cell number of DMSO treated wells. Y-axis represents the fold change of the percentage of ZIKV infection, which was calculated by dividing the percentage of ZIKV infection of the chemical treated well by the average of the percentage of ZIKV infection of DMSO treated wells. The compounds in which the fold change of total cell number >1 and the fold change of the percentage of ZIKV infection <20% were further evaluated.

Generation of inhibitory curves. hNPCs were plated on 96-well plates with Accutase digestion at $8.5 \times 10^4/cm^2$ density and incubated overnight. For generating inhibitory curves of compound for inhibiting ZIKV infection, cells were first treated with DMSO or different doses of hit compounds for 1 h before ZIKV infection. The cells were then infected with ZIKV MR766 at a MOI=0.125. After 2 h of infection, the virus-containing medium was replaced by fresh virus-free medium and compounds were added again to the same wells. For generating inhibitory curves of compound for eliminating ZIKV, compounds were instead added after ZIKV infection. After 3 days incubation, the cells were fixed and stained for ZIKV envelope protein (ZIKV E) and DAPI was used to stain cell nuclei. Plates were analyzed with the ImageXpress$^{MICRO}$ Automated High-Content Analysis System. $IC_{50}$ was calculated using MasterPlex Reader Fit 2010.

RNA-seq analysis. hNPCs at 72 h post-inoculation were collected for RNA-seq analysis, including mock-infected hNPCs treated with DMSO, mock-infected hNPCs treated with 25 μM HH, mock-infected hNPCs treated with 15 μM AQ, ZIKV (MR766 strain, MOI=0.125) infected hNPCs treated with DMSO, ZIKV-infected hNPCs treated with 25 μM HH, and ZIKV-infected hNPCs treated with 15 μM AQ. The RNA from hNPCs in each condition was extracted with Absolutely RNA Nanoprep kit (Agilent Technologies, 400753). The RNA quality was validated with a bioanalyzer (Agilent). The cDNA libraries were synthesized using the TruSeq RNA Sample Preparation kit (Illumina) and sequenced in single-read with the HiSeq4000 sequencer (Illumina) at Weill Cornell Genomics Resources Core Facility. The reads were aligned to the human hg19 reference genome with Tophat2. Gene expression data were analyzed with Cufflinks (Trapnell et al., Nature Biotech 28, 511-15, 2010). To generate heat maps displaying the differential gene expression patterns of different samples, The expression values (RPKM) were normalized per gene over all samples, to be specific, for each gene we calculated the mean and standard deviation (stdev) of expression over all samples, and linearly transformed the expression value using the formula (RPKM-mean)/stdev. The heat maps were then generated by Heatmap.2 in the R plots package. Gene ontology pathway analysis was performed using the DAVID function annotation tool.

The GEO accession number is GEO89334.

Immunocytochemistry and immunohistochemistry analysis. Cells were fixed with 4% paraformaldehyde for 20 min at room temperature (RT) and blocked in a solution of $Mg^{2+}$ and $Ca^{2+}$ free PBS containing 5% horse serum and 0.3% Triton-X for 1 h at room temperature and followed by incubation with primary antibody at 4° C. overnight. The following primary antibodies and dilutions have been used in this study: mouse anti-Flavivirus group antigen antibody (ZIKV E) (1:2000; Millipore, clone D1-4G2-4-15), mouse anti-Ki67 (1:200, DAKO, MIB-1), rabbit anti-Ki67 (1:500, Thermofisher, SP-6), rabbit anti-cleaved caspase-3 (1:1000, Cell Signaling Technology, Asp15), goat anti-SOX2 (1:100, Santa Cruz, sc-17320), rabbit anti-SOX2 (1:200, Biolegend, N-term), mouse anti-NESTIN (1:1000, Neuromics, MO15012), rabbit anti-TUJ1 antibody (1:500, Covance, MRB-435P), and chicken anti-MAP2 (1:1000, Abcam, Ab5392). The secondary antibodies include donkey anti-mouse, goat, rabbit or chicken secondary antibodies conjugated with Alexa-Fluor-488, Alexa-Fluor-594 or Alexa-Fluor-647 fluorophore (1:500, Life Technologies). Nuclei were counterstained by DAPI.

The immunohistochemical analysis of mouse tissues was performed on cryosections. In brief, the tissues were fixed overnight with 4% PFA at 4° C., embedded in OCT, and then sectioned at 30 μm for immunostaining. The primary and secondary antibodies were used as described above.

RNA Extraction and qRT-PCR. Total RNA of cultured cells and organs was extracted with RNeasy plus mini kit (Qiagen). vRNA from cell culture supernatant or mouse serum was extracted with QIAampe viral RNA mini kit (Qiagen). Reverse transcription was carried out with High Capacity cDNA Reverse Transcription kit (Thermo Fisher) or SuperScript III First-Strand Synthesis System (Theromo Fisher). qRT-PCR reactions were performed with the Light-Cycler 480 SYBR Green I Master Mix (Roche). ZIKV vRNA levels were calculated using a standard curve generated using serial 10-fold dilutions of ZIKV vRNA. Primer sets used in qPCR were as follow:

```
ZIKV-vRNA-forward:
CAAGGAGTGGGAAGCGGAG;

ZIKV-vRNA-reverse:
CCATGTGATGTCACCTGCTCT;

ZIKV-(-) RNA-forward:
AGATGACTGCGTTGTGAAGC

ZIKV-(-) RNA-reverse:
GAGCAGAACGGGACTTCTTC

Human ACTB-forward:
ACCTTCTACAATGAGCTGCG

Human ACTB-reverse:
CCTGGATAGCAACGTACATGG

Mouse Actb-forward:
ACCTTCTACAATGAGCTGCG

Mouse Actb-reverse:
CTGGATGGCTACGTACATGG
```

Adult mouse infection and in vivo drug testing. 6-8 week old female SCID-Beige mice were infected with ZIKV ($2.5 \times 10^5$ PFU in 0.5 ml culture fluid) through intraperitoneal injection. For pre-infection treatment, drug candidates were administrated to mice 12 h before ZIKV inoculation and followed by treatment once per day. HH was administrated subcutaneously at the dose of 100 mg/kg body weight. AQ was administrated with intraperitoneal injection at the dose of 40 mg/kg body weight. PBS was used as the vehicle control.

For ZIKV kinetics analysis, 6-8 weeks old female SCID-beige mice were inoculated with ($1 \times 10^6$ PFU for MR766 strain or $3 \times 10^6$ PFU for FSS13025 strain in 0.5 ml culture fluid) through intraperitoneal injection. The mice were euthanized at the indicated time points and analyzed with qRT-PCR to validate the ZIKV level in vivo. 24-48 h after the detection of total and replicating (-) strand ZIKV vRNA in mouse brain, HH was administrated subcutaneously at the dose of 100 mg/kg body weight per day for 5 days (MR766 strain) or 7 days (FSS13025 strain). Mice were then euthanized and brains were collected and analyzed using qRT-PCR.

Statistical Analysis. N=3 independent biological replicates were used if not otherwise specifically indicated. n.s. indicates non-significant difference. For in vitro experiments, p values were calculated by unpaired two-tailed Student's t-test if not otherwise specifically indicated. For in vivo experiments, p values were calculated by one-way repeated measures ANOVA or two-way repeated measures ANOVA with a Bonferroni test for multiple comparisons. $*p<0.05$, $p<0.01$ and $*p<0.001$.

Example 2

This example describes synthesis and use of compounds of the present disclosure.

Figure 9:
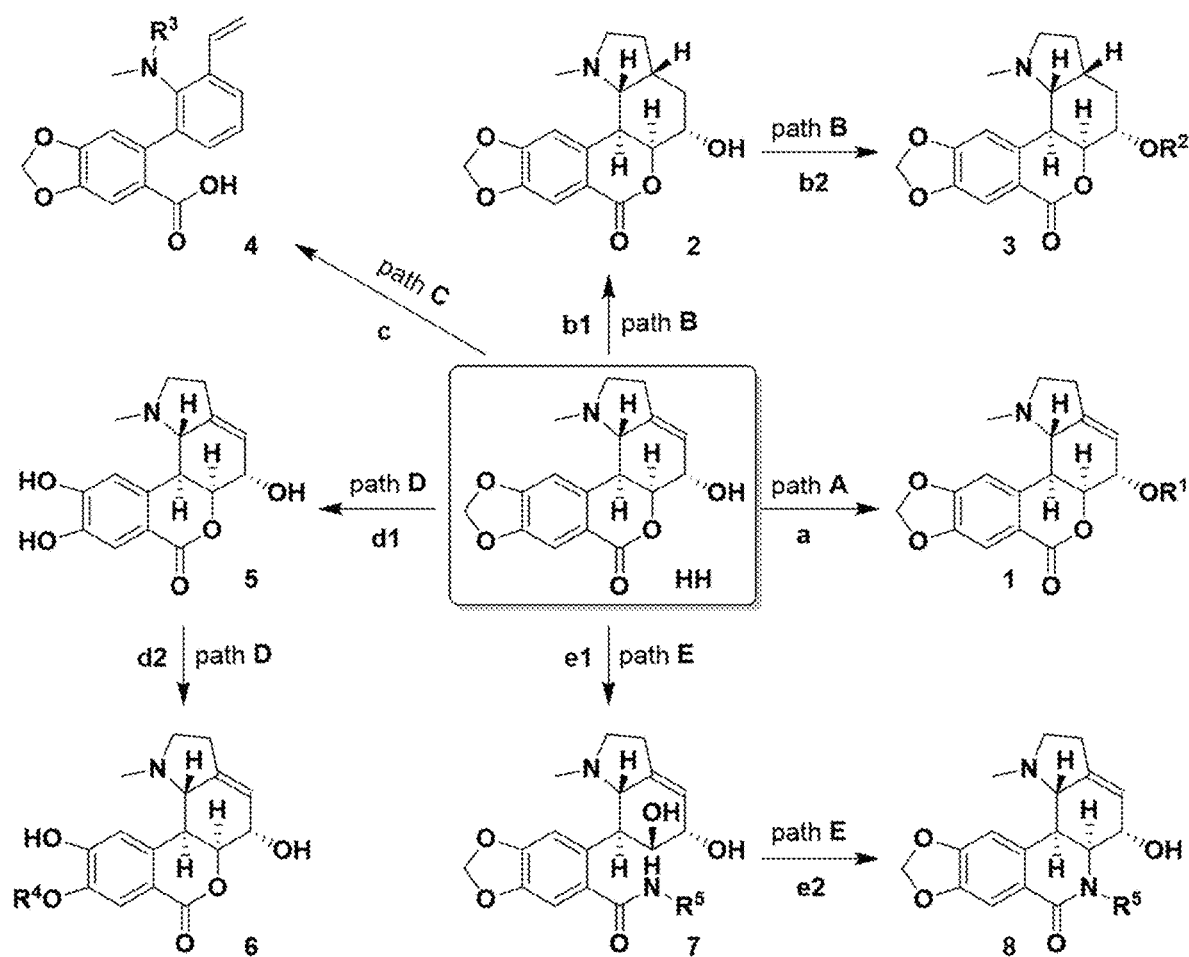
FIG. 9 shows modifications of HH. The five major functional groups, hydroxyl, alkene, tertiary amine, acetal, and lactone, as shown in paths A-E to generate compounds 1-8. Reagents and conditions: (a) NaH, $R_1X$; (b1) Hz, Pd/C; (b2) NaH, $R^2X$; (c) $R^3X$; t-BuOK/t-BuOH; (d1) $BBr_3$; (d2) $K_2CO_3$, $R^4X$; (e1) $R^5NH_2$; (e2) $[Cp*IrCl_2]_2$, NaOAc.

HH contains five major functional groups (FIG. 9): hydroxyl, alkene, tertiary amine, acetal, and lactone groups. The groups can be modified individually and/or in combinations. The hydroxyl group can be modified as the corresponding ether or ester 1 (path A). In path B, the alkene is hydrogenated under the catalysis of Pd/C as the corresponding saturated form 2. The hydroxyl group in 2 is then modified to generate 3. To modify the tertiary amine group, a Hoffman elimination reaction is used to produce 4 (path C). The acetal group can be removed by boron tribromide ($BBr_3$) in path D to form 5, which can be further derivatized to provide 6. In path E, the lactone group is converted first to amide 7 and subsequently to lactam 8.

We have validated the synthetic routes as illustrated in paths A, B, and D by synthesizing HH analogs 1a, 1b, 2, and 5 (FIG. 2A). Briefly, HH was treated with sodium hydride (NaH) and methyl iodide ($CH_3I$) to generate 1a in 68% yield. Compound 1b was formed when pyridine was used as the base and acetic anhydride as the electrophile. Hydrogenation of HH in the presence of Pd/C and $H_2$ produced compound 2 while reaction of HH with $BBr_3$ generated the catechol 5.

All the four HH analogs were tested in the assay as described in FIG. 1A. The inhibitory profiles for each analog is shown in table 2. Compound 1a was inactive at the concentration tested, while 1b had comparable activity as HH, suggesting the importance of a free hydroxyl or a polar group at this position. The hydrogenated product 2 did not show detectable activity possibly because the conformational change due to the loss of the rigid double bond in HH. Compound 5 showed similar inhibitory profile as HH, and its catechol unit opens up many opportunities for further modifications. These results demonstrated that different HH analogs have significant activity and can be used for treatment/prevention of ZIKV.

Figure 10:
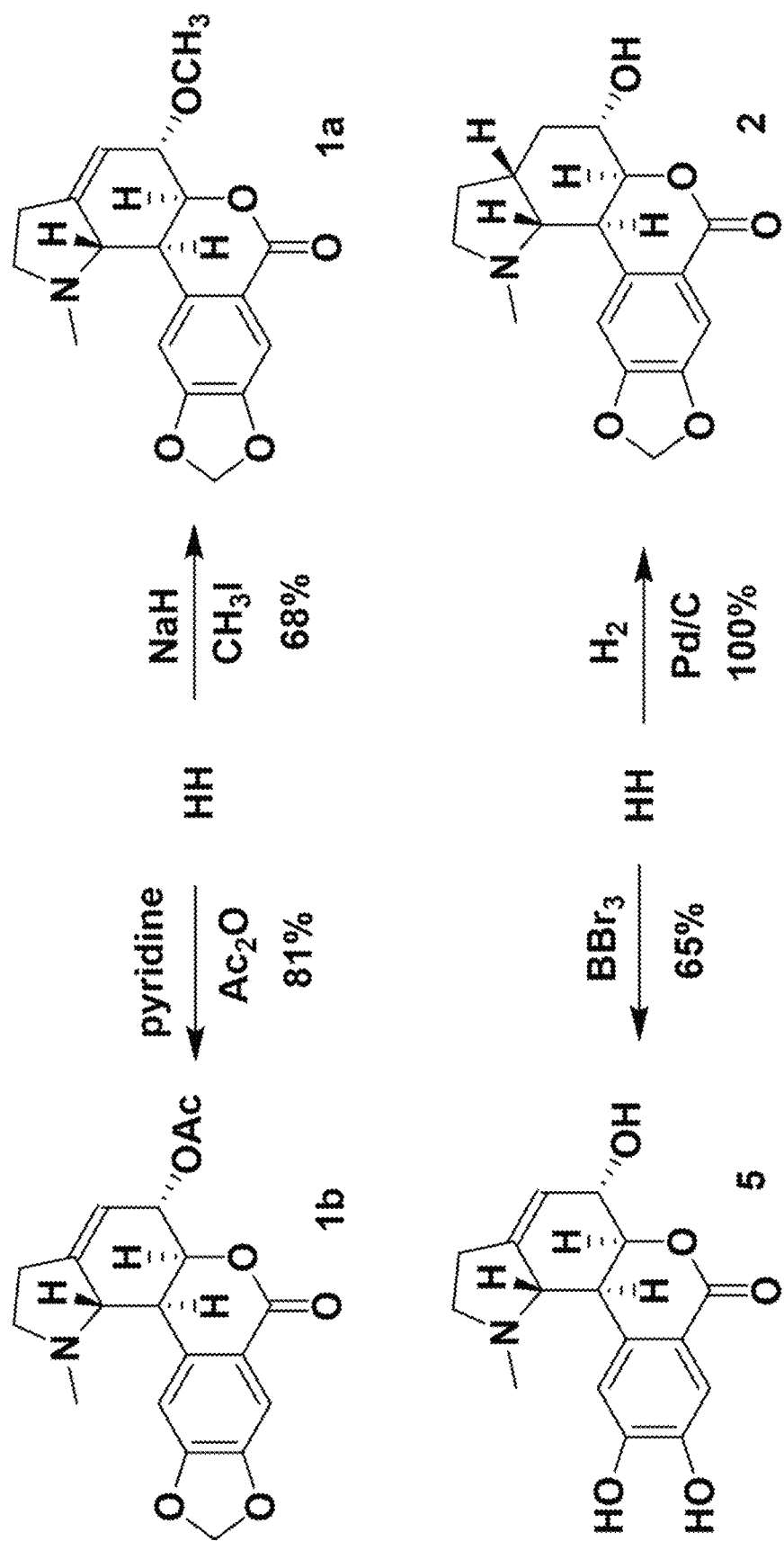
FIG. 10 shows synthesis of compounds 1a, 1b, 2.
Figure 11:
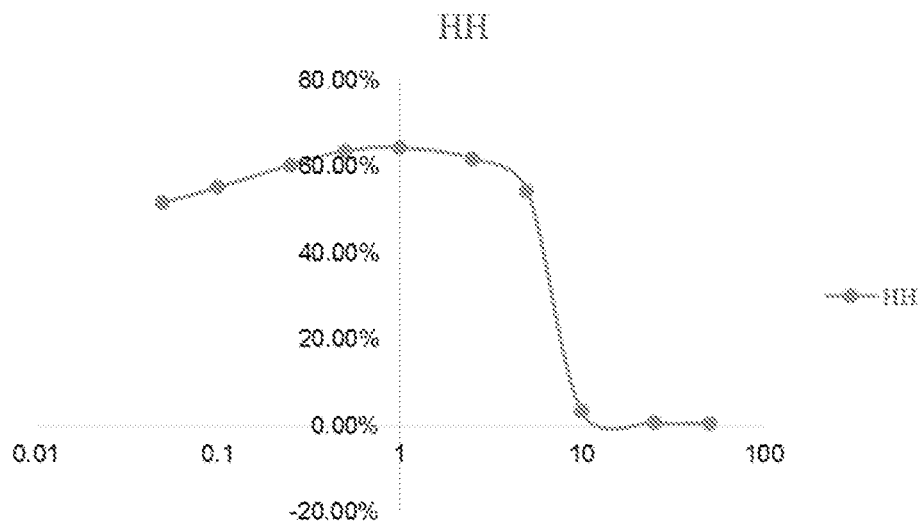
FIG. 11 (A-H) shows $IC_{50}$ data for compounds of the present disclosure.
Figure 11:
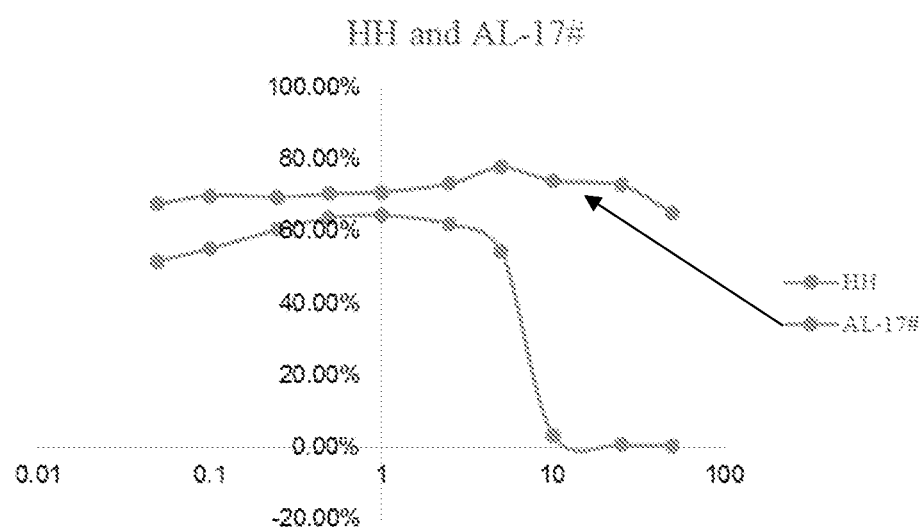
Figure 11:
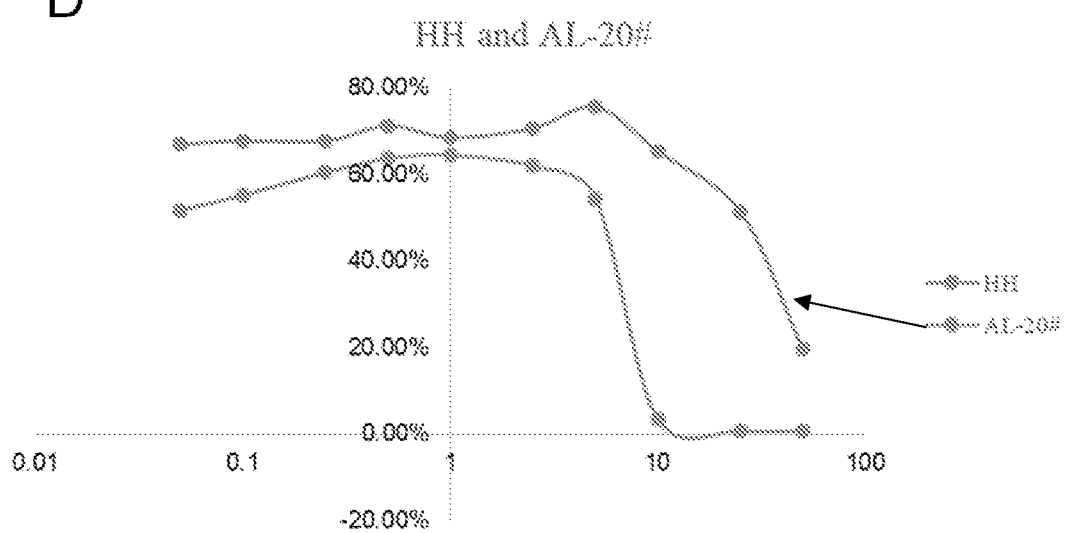
Figure 11:
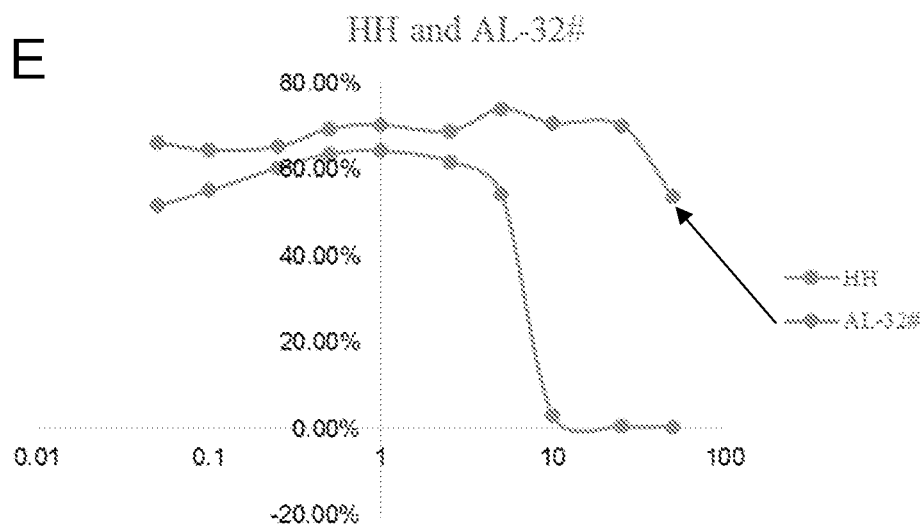
Figure 11:
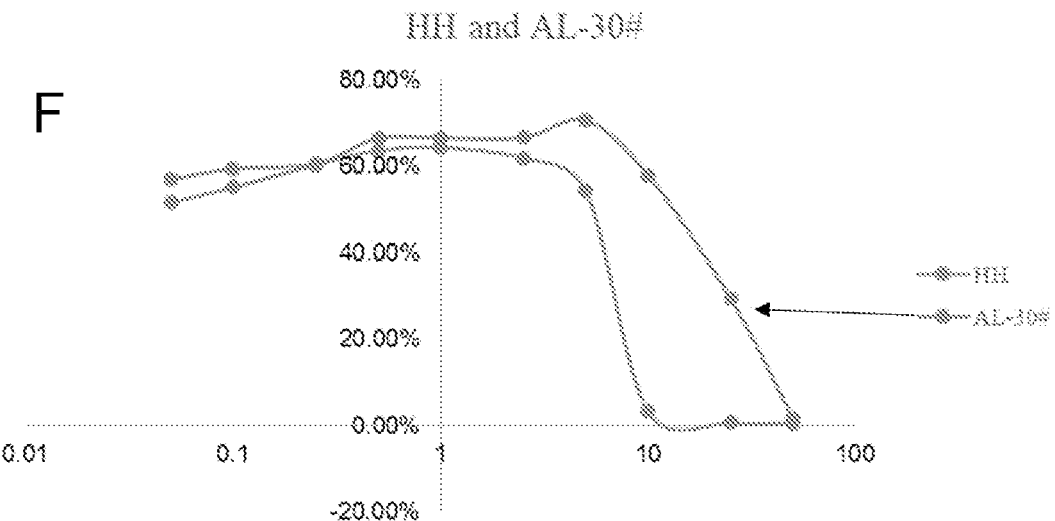
Figure 11:
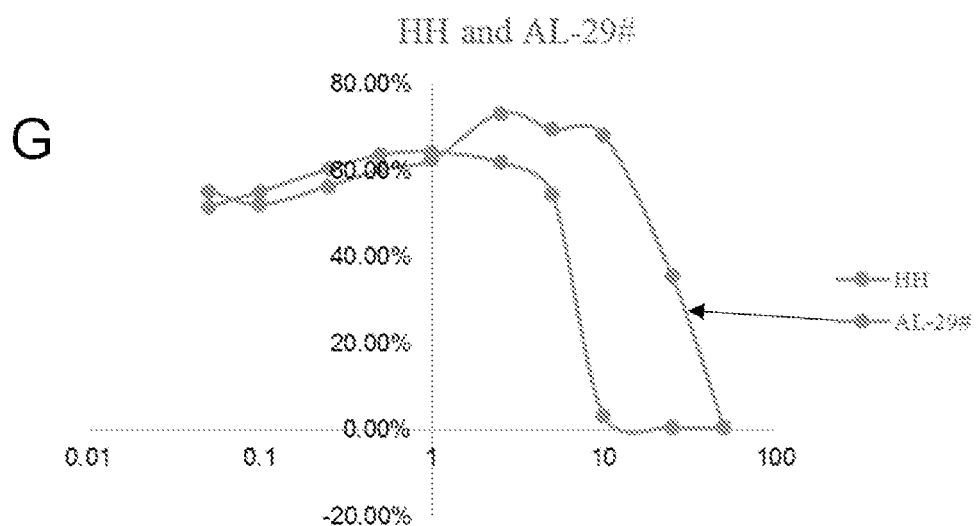
Figure 11:
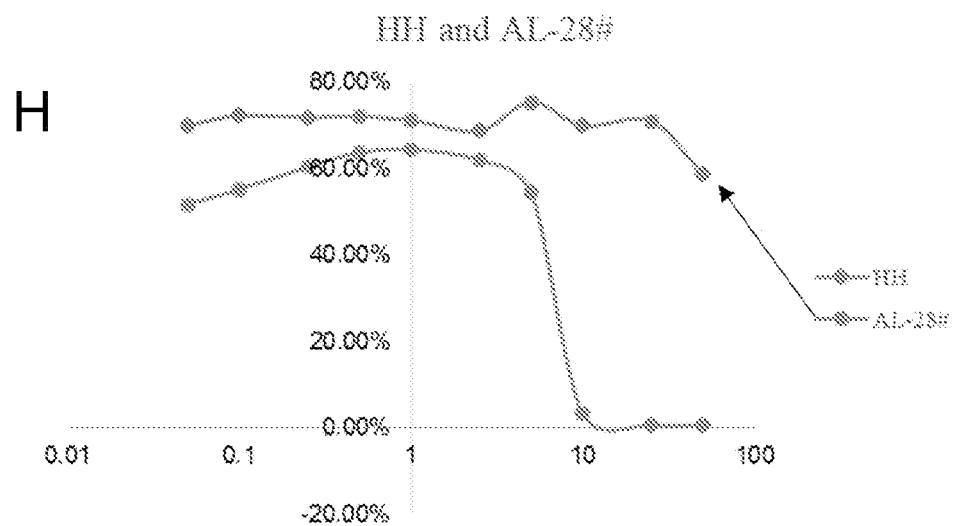

Table 2 shows $IC_{50}$ of the compounds shown in FIG. 10.

TABLE 2

| Compound | $IC_{50}$ |
|---|---|
| 1a | No Activity |
| 1b | 2.4 μM |
| 2 | No Activity |
| 5 | 6.8 μM |

Example 3

This example describes efficacy of compounds of the present disclosure.

FIGS. 11A-H show $IC_{50}$ data for compounds of the present disclosure.

Although the present disclosure has been described with respect to one or more particular embodiments and/or examples, it will be understood that other embodiments and/or examples of the present disclosure may be made without departing from the scope of the present disclosure.

---

The invention claimed is:

1. A compound having the following structure:

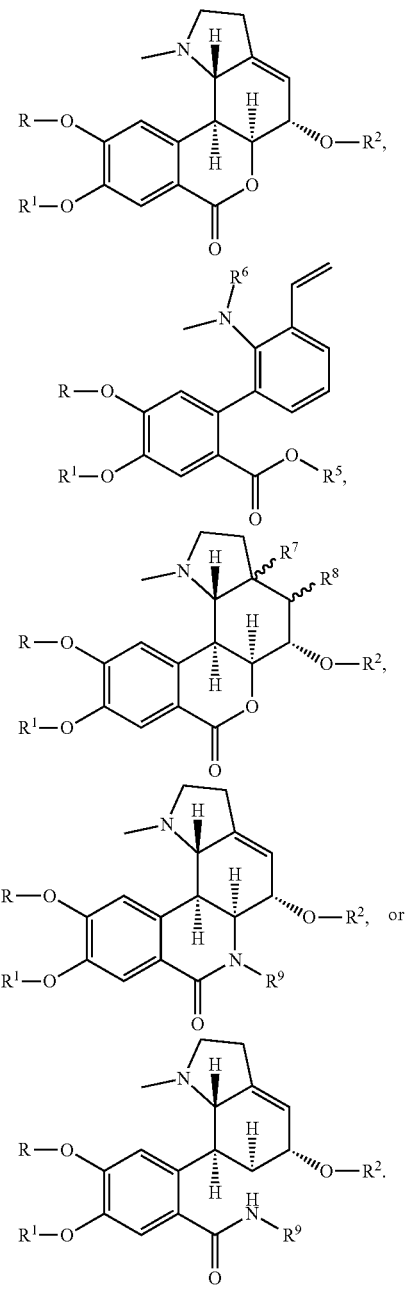

wherein R and $R^1$ are independently selected from H; $C_1$ to $C_8$ acyl aliphatic groups; $C_1$ to $C_8$ carbamide aliphatic groups; $C_1$ to $C_8$ amide aliphatic groups; $C_1$ to $C_8$ aliphatic groups; $C_1$ to $C_8$ acyl aliphatic aryl groups, wherein $C_1$ to $C_8$ is the length of the aliphatic portion of the acyl aliphatic aryl group; $C_1$ to $C_8$ carbamide aliphatic aryl groups, wherein $C_1$ to $C_8$ is the length of the aliphatic portion of the carbamide aliphatic aryl group; and $C_1$ to $C_8$ amide aliphatic aryl groups, wherein $C_1$ to $C_8$ is the length of the aliphatic portion of the amide aliphatic aryl group; or R and $R^1$ taken together form

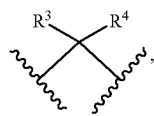

wherein $R^3$ and $R^4$ are independently selected from H and $C_1$ to $C_8$ aliphatic groups;

wherein $R^1$ is selected from H; $C_1$ to $C_8$ acyl aliphatic groups; $C_1$ to $C_8$ carbamide aliphatic groups; $C_1$ to $C_8$ amide aliphatic groups; $C_1$ to $C_8$ acyl aromatic groups; $C_1$ to $C_8$ carbamide aryl groups; and $C_1$ to $C_8$ amide aryl groups,

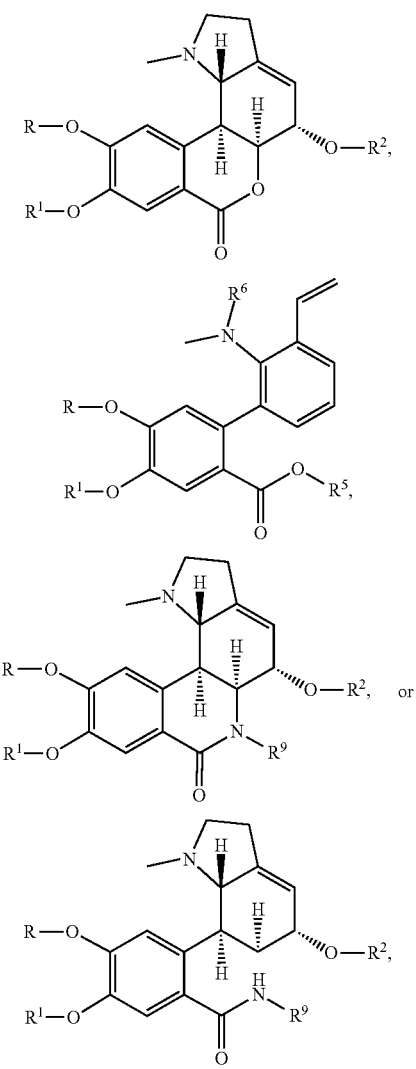

or R² has the following structure:

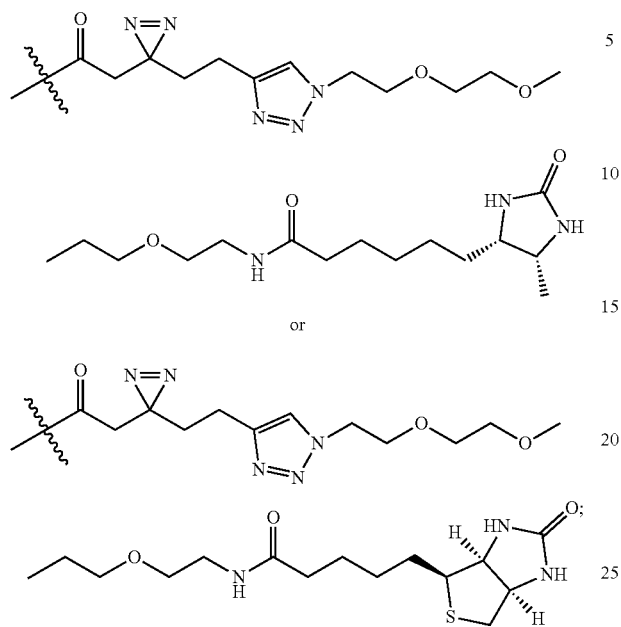

wherein R⁵ is selected from H and $C_1$ to $C_8$ aliphatic groups, or R⁵ has the following structure:

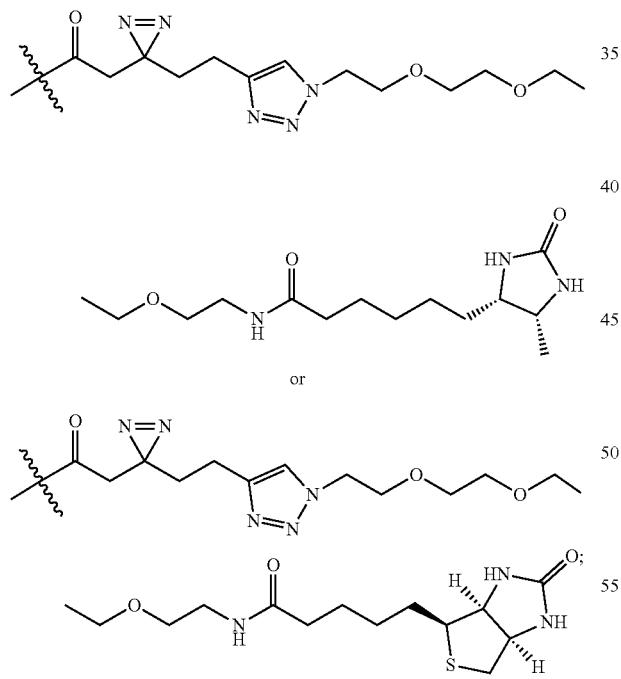

wherein R⁶ is selected from H and $C_1$ to $C_8$ aliphatic groups;
wherein R⁷ is H, wherein the stereochemistry is R or S;
wherein R⁸ is H, wherein the stereochemistry is R or S; and
wherein R⁹ is a $C_1$ to $C_8$ aliphatic group, with the proviso that when the compound does not have the following structure:

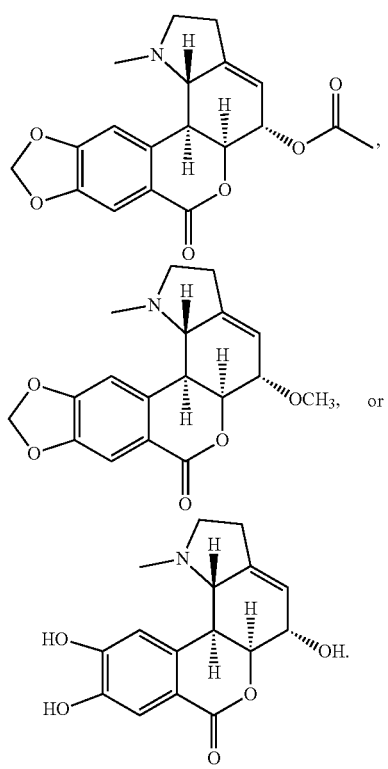

and the proviso that when the compound has the following structure:

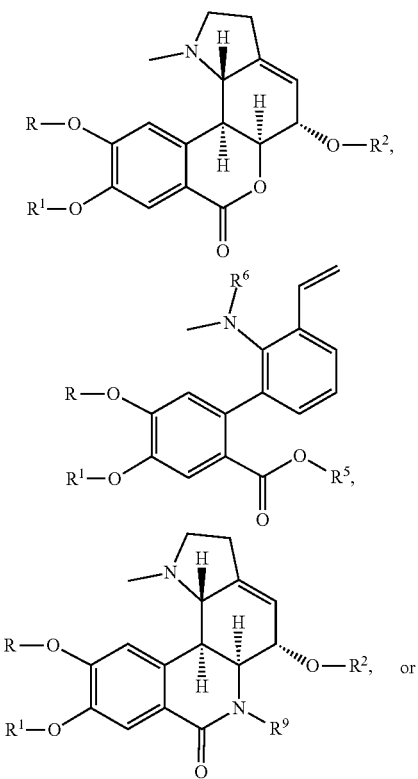

-continued
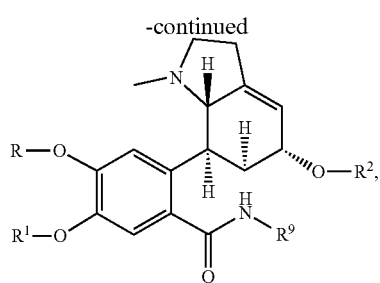
that when $R^2$ is H that R and $R^1$ are not taken together to form
2. The compound of claim 1, wherein $R^2$ is acetyl or trifluoromethyl acetyl.
3. The compound of claim 1, wherein the compound has the following structure:
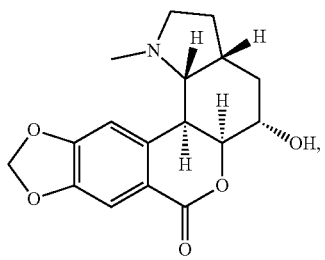
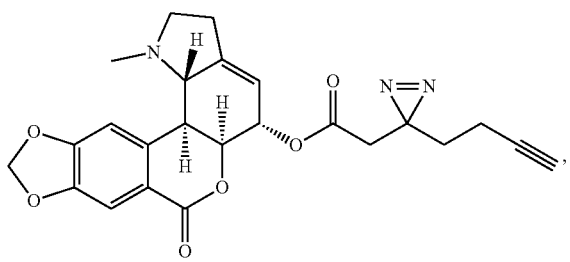
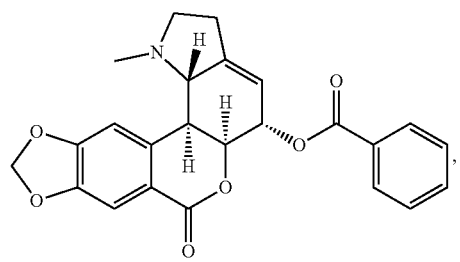
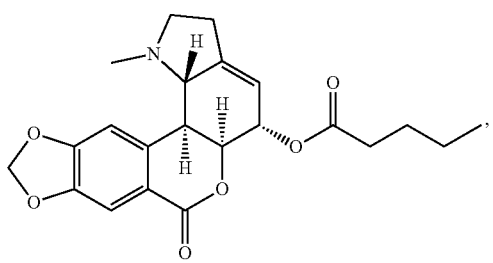
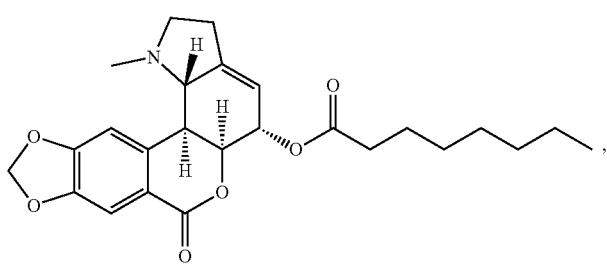
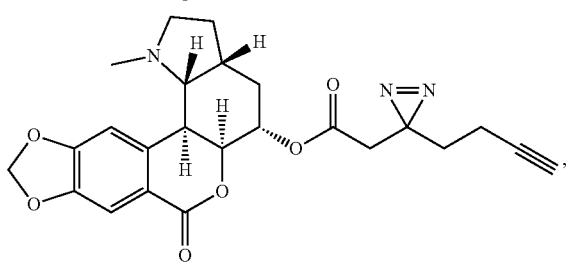
or
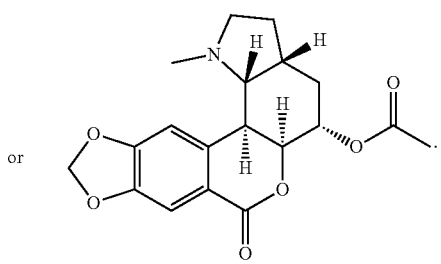
AL-32

4. The compound of claim 1, wherein the compound is:

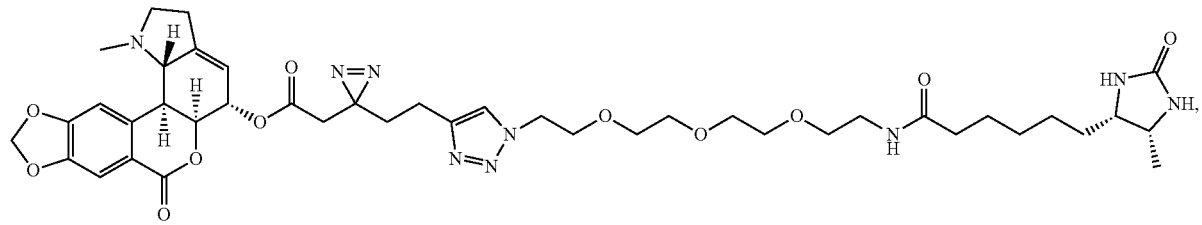

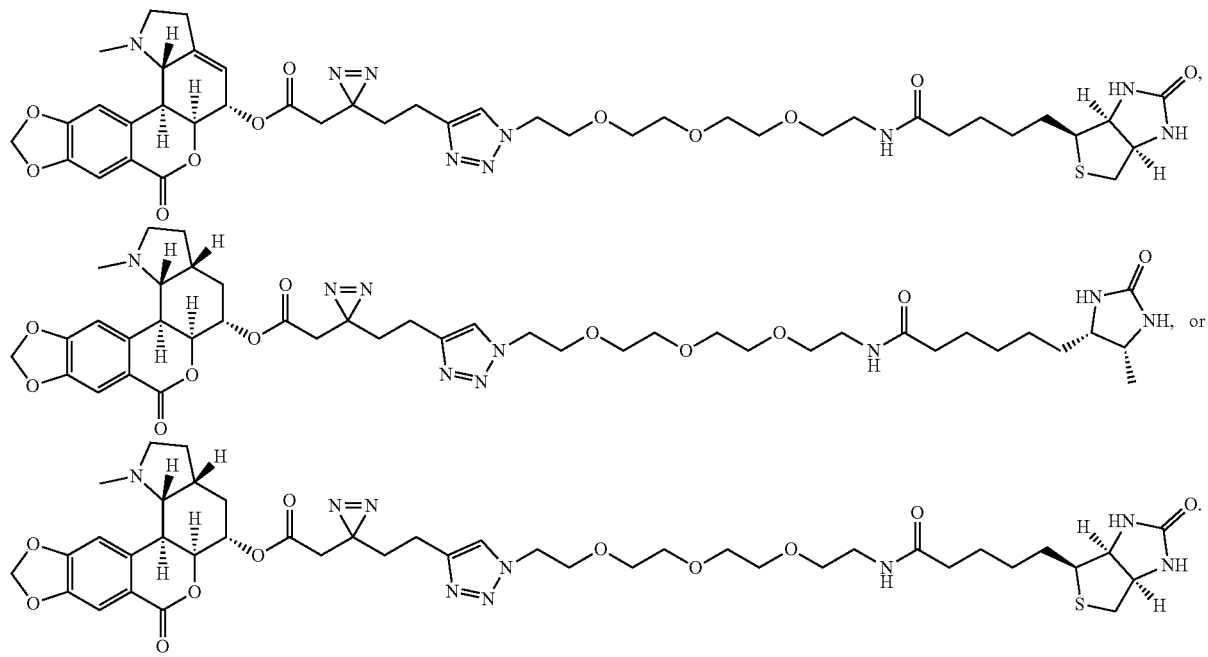

5. A composition comprising one or more compound of claim 1 or a combination thereof and at least one pharmaceutically acceptable carrier or excipient.

6. A method for inhibiting and/or treating Zika virus infection, comprising administering to a subject in need of inhibition and/or treatment a composition comprising one or more compound of claim 1.

7. The method of claim 6, wherein $R^2$ is acetyl or trifluoromethyl acetyl.

8. The method of claim 6, wherein the compound or composition comprising a compound has the following structure:

-continued

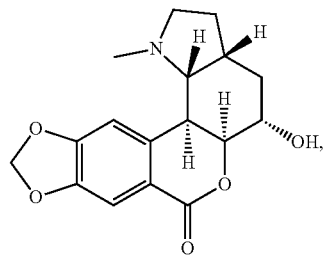

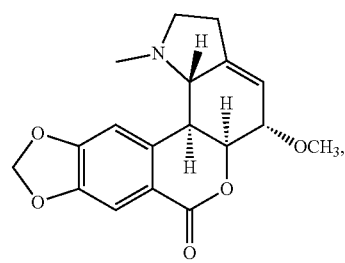

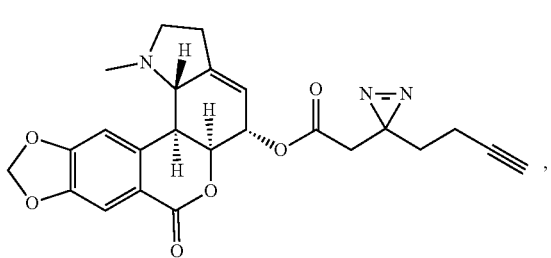

57
-continued
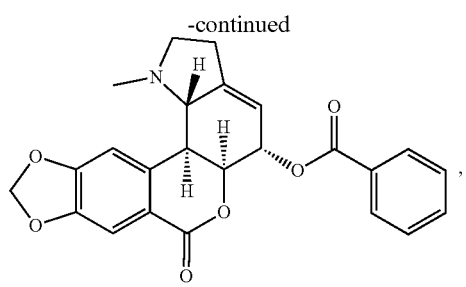
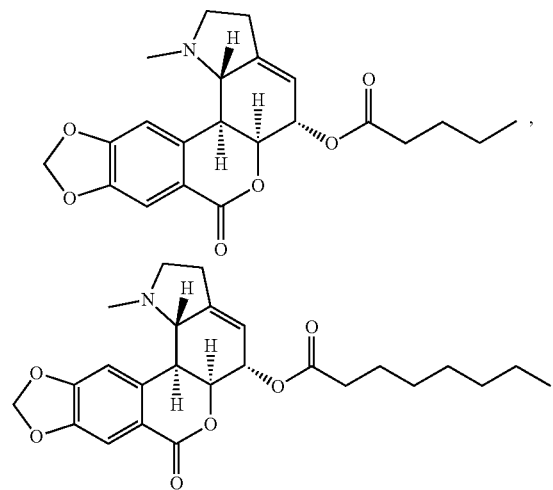
58
-continued
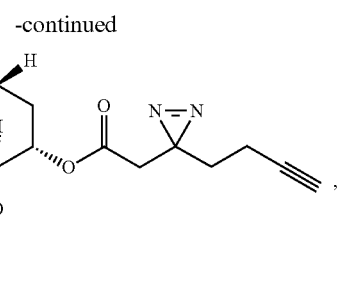
or
9. The method of claim 6, wherein the compound or composition comprising a compound has the following structure:
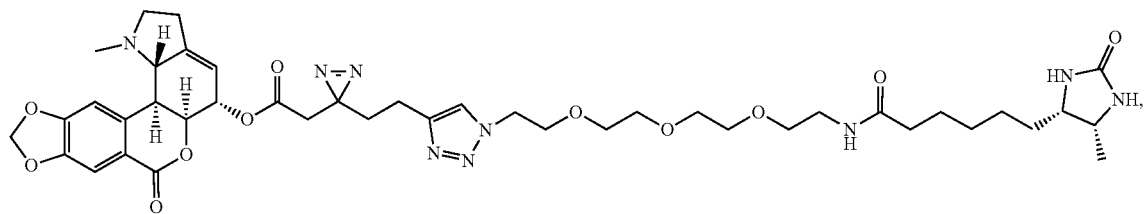
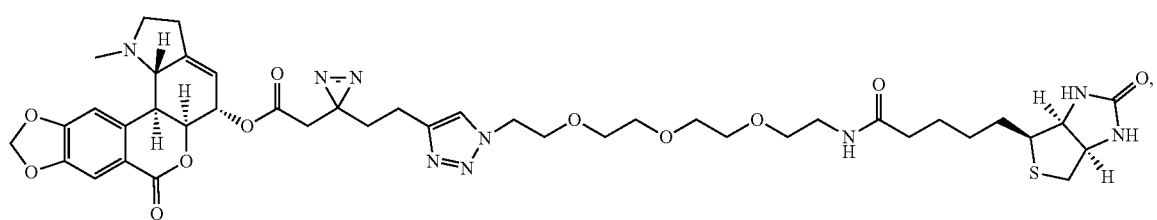

-continued
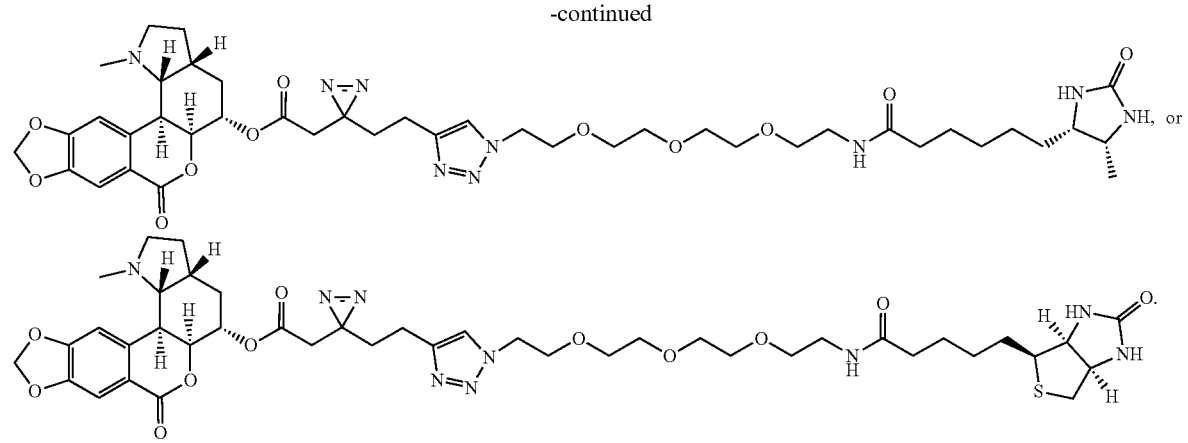
* * * * *

SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
caaggagtgg gaagcggag                    19

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ccatgtgatg tcacctgctc t                 21

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
agatgactgc gttgtgaagc                   20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gagcagaacg ggacttcttc                   20

-continued

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
accttctaca atgagctgcg                                             20

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
cctggatagc aacgtacatg g                                           21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
accttctaca atgagctgcg                                             20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ctggatggct acgtacatgg                                             20